US012697316B2

(12) United States Patent
Factor et al.

(10) Patent No.: US 12,697,316 B2
(45) Date of Patent: Aug. 4, 2026

(54) COMBINATION THERAPY WITH ACETYL-LEUCINE AND MIGLUSTAT

(71) Applicant: INTRABIO LTD., London (GB)

(72) Inventors: Mallory Factor, Mayfair (GB); Michael Strupp, Munich (DE)

(73) Assignee: INTRABIO LTD., London (GB)

( * ) Notice: Subject to any disclaimer, the term of this patent is extended or adjusted under 35 U.S.C. 154(b) by 994 days.

(21) Appl. No.: 17/623,313

(22) PCT Filed: Jun. 26, 2020

(86) PCT No.: PCT/IB2020/056096
§ 371 (c)(1),
(2) Date: Dec. 28, 2021

(87) PCT Pub. No.: WO2020/261230
PCT Pub. Date: Dec. 30, 2020

(65) Prior Publication Data
US 2022/0362189 A1 Nov. 17, 2022

Related U.S. Application Data

(60) Provisional application No. 62/931,003, filed on Nov. 5, 2019, provisional application No. 62/868,383, filed on Jun. 28, 2019.

(51) Int. Cl.

| | |
|---|---|
| *A61K 31/198* | (2006.01) |
| *A61K 9/00* | (2006.01) |
| *A61K 31/197* | (2006.01) |
| *A61K 31/445* | (2006.01) |
| *A61P 3/00* | (2006.01) |
| *A61P 25/28* | (2006.01) |

(52) U.S. Cl.
CPC .......... *A61K 31/197* (2013.01); *A61K 9/0053* (2013.01); *A61K 31/445* (2013.01); *A61P 3/00* (2018.01)

(58) Field of Classification Search
CPC .. A61K 31/197; A61K 9/0053; A61K 31/445; A61K 31/198; A61P 3/00; A61P 25/28
See application file for complete search history.

(56) References Cited

U.S. PATENT DOCUMENTS

| | | | |
|---|---|---|---|
| 8,202,525 | B2 | 6/2012 | Crain et al. |
| 9,283,181 | B2 | 3/2016 | Calias et al. |
| 10,905,670 | B2 | 2/2021 | Factor et al. |
| 10,950,670 | B2 | 3/2021 | Luo |
| 11,083,718 | B2 | 8/2021 | Strupp |
| 11,400,067 | B2 | 8/2022 | Strupp |
| 11,471,434 | B2 | 10/2022 | Strupp et al. |
| 11,660,279 | B2 | 5/2023 | Factor et al. |
| 11,793,782 | B2 | 10/2023 | Factor |
| 11,998,518 | B2 | 6/2024 | Factor et al. |

| | | | |
|---|---|---|---|
| 12,144,792 | B2 | 11/2024 | Strupp |
| 12,145,899 | B2 | 11/2024 | Mann |
| 12,329,733 | B2 | 6/2025 | Factor et al. |
| 2002/0095135 | A1 | 7/2002 | Meeker et al. |
| 2004/0127501 | A1 | 7/2004 | Chen et al. |
| 2006/0063827 | A1 | 3/2006 | Yu et al. |
| 2006/0128717 | A1 | 6/2006 | Sun et al. |
| 2006/0235022 | A1 | 10/2006 | Sun |
| 2006/0235055 | A1 | 10/2006 | Kyle et al. |
| 2006/0241117 | A1 | 10/2006 | Sun |
| 2007/0027159 | A1 | 2/2007 | Kyle et al. |
| 2007/0032500 | A1 | 2/2007 | Sun et al. |
| 2007/0276041 | A1 | 11/2007 | Oonuki et al. |
| 2008/0214649 | A1 | 9/2008 | Yu et al. |
| 2009/0318555 | A1 | 12/2009 | Fabre et al. |
| 2013/0123239 | A1 | 5/2013 | Kurose |
| 2013/0142888 | A1 | 6/2013 | Rekik |
| 2013/0317036 | A1 | 11/2013 | Rekik |
| 2014/0080885 | A1 | 3/2014 | Pennypacker et al. |
| 2014/0350056 | A1 | 11/2014 | Yu |
| 2019/0046486 | A1 | 2/2019 | De Rienzo et al. |
| 2019/0083438 | A1 | 3/2019 | Factor et al. |
| 2019/0201359 | A1 | 7/2019 | Strupp |
| 2020/0179320 | A1 | 6/2020 | Strupp |
| 2020/0253905 | A1 | 8/2020 | Strupp et al. |
| 2020/0338034 | A1 | 10/2020 | Factor |
| 2021/0106548 | A1 | 4/2021 | Factor et al. |
| 2021/0196659 | A1 | 7/2021 | Factor |
| 2021/0361632 | A1 | 11/2021 | Strupp |
| 2022/0024858 | A1 | 1/2022 | Mann |

(Continued)

FOREIGN PATENT DOCUMENTS

| | | |
|---|---|---|
| CN | 103079550 A | 5/2013 |
| CN | 103814046 A | 5/2014 |

(Continued)

OTHER PUBLICATIONS

Bremova et al, "Acetyl-DL-leucine in Niemann-Pick type C A case series," Amer J Neurol. 85:1368-1375 (2015) (Year: 2015).*
Cortina-Borja et al, "Annual severity increment score as a tool for stratifying patients with Niemann-Pick disease type C and for recruitment to clinical trials," Orphanet J Rare Dis 13:143 (2018) (Year: 2018).*
Zavesca product (Miglustat Europa Health documents, accessed Apr. 16, 2025 at URL ec.europa.eu/health/documents/community-register/2010/2010060278532/anx_78532_en.pdf, pp. 1-25 (Jun. 2010) (Year: 2010).*
Platt et al, "Lysosomal storage diseases," Nature Reviews Disease Primers 4:27 (2018) (Year: 2018).*
Vanier, "Niemann-Pick disease type C," Orphanet Journal of Rare Diseases 5:16 (2010)) (Year: 2010).*
Barclay, L.L., et al., "The String Test: an Early Behavioral Change in Thiamine Deficiency," Pharmacology, Biochemistry, and Behavior 14(2):153-157, Elsevier, United States (Feb. 1981).

(Continued)

*Primary Examiner* — Julie Ha
*Assistant Examiner* — Kristina M Hellman
(74) *Attorney, Agent, or Firm* — Sterne, Kessler, Goldstein & Fox P.L.L.C.

(57) ABSTRACT

The present disclosure provides methods of treating lysosomal storage disorders (LSDs) in a subject in need thereof by administering a combination of acetyl-leucine and miglustat to the subject, wherein subject is naive to treatment with miglustat.

21 Claims, 24 Drawing Sheets

(56) References Cited

U.S. PATENT DOCUMENTS

| | | | |
|---|---|---|---|
| 2022/0142959 A1 | 5/2022 | Factor et al. | |
| 2022/0331278 A1 | 10/2022 | Strupp | |
| 2023/0051742 A1 | 2/2023 | Strupp | |
| 2023/0201150 A1 | 6/2023 | Strupp | |
| 2023/0210799 A1 | 7/2023 | Strupp | |
| 2023/0346732 A1 | 11/2023 | Factor et al. | |
| 2024/0189267 A1 | 6/2024 | Strupp | |
| 2024/0197663 A1 | 6/2024 | Strupp | |
| 2024/0208895 A1 | 6/2024 | Churchill | |
| 2025/0129011 A1 | 4/2025 | Mann | |

FOREIGN PATENT DOCUMENTS

| | | | | |
|---|---|---|---|---|
| EP | 0226304 A1 | 6/1987 | | |
| EP | 0288447 A1 | 10/1988 | | |
| FR | 2905600 A1 | 3/2008 | | |
| JP | 2009269856 A | 11/2009 | | |
| JP | 2014503596 A | 2/2014 | | |
| JP | 2016513084 A | 5/2016 | | |
| RU | 2012151575 A | 7/2014 | | |
| RU | 2680413 C1 | 2/2019 | | |
| WO | WO-9526325 A2 | 10/1995 | | |
| WO | WO-9621464 A1 | 7/1996 | | |
| WO | WO-2006036634 A2 | 4/2006 | | |
| WO | WO-2006097527 A1 | 9/2006 | | |
| WO | WO-2006101940 A2 | 9/2006 | | |
| WO | WO-2008032222 A2 | 3/2008 | | |
| WO | WO-2008101693 A2 | 8/2008 | | |
| WO | WO-2008101693 A3 | 11/2008 | | |
| WO | WO-2009079790 A1 | 7/2009 | | |
| WO | WO-2011097148 A2 | 8/2011 | | |
| WO | WO-2011151685 A1 | 12/2011 | | |
| WO | WO-2012064892 A1 | 5/2012 | | |
| WO | WO-2013095275 A1 | 6/2013 | | |
| WO | WO-2013182652 A1 | 12/2013 | | |
| WO | WO-2014122184 A1 | 8/2014 | | |
| WO | WO-2017182802 A1 * | 10/2017 | .......... | A61K 31/198 |
| WO | WO-2018007864 A1 | 1/2018 | | |
| WO | WO-2018029657 A1 | 2/2018 | | |
| WO | WO-2018029658 A1 | 2/2018 | | |
| WO | WO-2018178670 A1 | 10/2018 | | |
| WO | WO-2018229738 A1 | 12/2018 | | |
| WO | WO-2019078915 A1 | 4/2019 | | |
| WO | WO-2019079536 A1 | 4/2019 | | |
| WO | WO-2019159110 A1 | 8/2019 | | |
| WO | WO-2020052620 A1 | 3/2020 | | |
| WO | WO-2020115715 A1 | 6/2020 | | |
| WO | WO-2020178721 A1 | 9/2020 | | |
| WO | WO-2020261230 A1 | 12/2020 | | |
| WO | WO-2021048431 A1 | 3/2021 | | |
| WO | WO-2021144720 A1 | 7/2021 | | |
| WO | WO-2021234642 A1 | 11/2021 | | |
| WO | WO-2022264037 A1 | 12/2022 | | |
| WO | WO-2023196841 A2 | 10/2023 | | |
| WO | WO-2025175092 A1 | 8/2025 | | |
| WO | WO-2025264957 A2 | 12/2025 | | |

OTHER PUBLICATIONS

Boland, B., et al., "Macroautophagy is Not Directly Involved in the Metabolism of Amyloid Precursor Protein," The Journal of Biological Chemistry 285(48):37415-37426, American Society for Biochemistry and Molecular Biology, United States (Nov. 2010).

Bremova, T., et al., "Acetyl-dl-leucine in Niemann-pick Type C: A Case Series," Neurology 85(16):1368-1375, Lippincott Williams & Wilkins, United States (Oct. 2015).

Bremova-Ertl, A., et al., "EPR1131 Acetyl-Leucine Slows Disease Progression in Lysosomal Storage Disorders," European Journal of Neurology 27(1):181, Wiley-Blackwell, United Kingdom (May 2020).

Champion, H., et al., "Dietary Modifications in Patients Receiving Miglustat," Journal of Inherited Metabolic Disease 33 (Suppl 3):S379-83, Wiley, United States (Dec. 2010).

Cheng, K.K., et al., "Highly Stabilized Curcumin Nanoparticles Tested in an in Vitro Blood-brain Barrier Model and in Alzheimer's Disease Tg2576 Mice," American Association of Pharmaceutical Scientists Journal(AAPSJ) 15(2):324-336, American Association of Pharmaceutical Scientists, United States (Apr. 2013).

Chida, J., et al., "An Efficient Extraction Method for Quantitation of Adenosine Triphosphate in Mammalian Tissues and Cells," Analytica Chimica Acta 727:8-12, Elsevier, Netherlands (May 2012).

Cortina-Borja, M., et al., "Annual Severity Increment Score as a Tool for Stratifying Patients with Niemann-Pick disease type C and for Recruitment to Clinical Trials, " Orphanet Journal of Rare Diseases 13(1):143, BioMed Central, United Kingdom (Aug. 2018).

Günther, L., et al., "N-Acetyl-L-Leucine Accelerates Vestibular Compensation after Unilateral Labyrinthectomy by Action in the Cerebellum and Thalamus," PLoS One 10(3):e0120891, Public Library of Science, United States (Mar. 2015).

Hammond, N., et al., "The Complexity of a Monogenic Neurodegenerative Disease: More Than Two Decades of Therapeutic Driven Research Into Niemann-pick Type C Disease," Biochimica et Biophysica Acta—Molecular and Cell Biology of Lipids 1864(8):1109-1123, Elsevier, Netherlands (Aug. 2019).

Hanson, L.R. and Frey II, W.H., "Intranasal Delivery Bypasses the Blood-brain Barrier to Target Therapeutic Agents to the Central Nervous System and Treat Neurodegenerative Disease," BMC neuroscience 9(Suppl 3):S5, BioMed Central, United Kingdom (Dec. 2008).

Harris, R.A., et al., "Overview of the Molecular and Biochemical Basis of Branched-chain Amino Acid Catabolism" The Journal of Nutrition 135(6 Suppl):1527S-1530S, Elsevier, United States (Jun. 2005).

Harris, R.A., et al., "Physiological Covalent Regulation of Rat Liver Branched-chain Alpha-ketoacid Dehydrogenase," Archives of Biochemistry and Biophysics 243(2):542-555, Academic Press, United States (Dec. 1985).

Héron, B., et al., "Miglustat therapy in the French cohort of paediatric patients with Niemann-Pick disease type C," Orphanet Journal of Rare Diseases 7:36, pp. 1-14, BioMed Central, United Kingdom (Jun. 2012).

International Search Report and Written Opinion for International Application No. PCT/IB2020/056096, European Patent Office, Netherlands, mailed on Sep. 29, 2020, 11 pages.

Jeyakumar, M., et al., "Delayed Symptom Onset and Increased Life Expectancy in Sandhoff Disease Mice Treated With N-butyldeoxynojirimycin," Proceedings of the National Academy of Sciences of the United States of America 96(11):6388-6393, National Academy of Sciences, United States (May 1999).

Jha, M.K., et al., "Pyruvate Dehydrogenase Kinases in the Nervous System: Their Principal Functions in Neuronal-glial Metabolic Interaction and Neuro-metabolic Disorders," Current Neuropharmacology 10(4):393-403, Bentham Science Publishers, United Arab Emirates (Dec. 2012).

Kabanov, A. V. and Batrakova, E.V., "New Technologies for Drug Delivery Across the Blood Brain Barrier," Current pharmaceutical design 10(12):1355-1363, Bentham Science Publishers, United Arab Emirates (2004).

Kato, M., et al., "Structural Basis for Inactivation of the Human Pyruvate Dehydrogenase Complex by Phosphorylation: Role of Disordered Phosphorylation Loops," Structure 16(12): 1849-1859, Cell Press, United States (Dec. 2008).

Kennedy, B.E., et al., "Pre-symptomatic Activation of Antioxidant Responses and Alterations in Glucose and Pyruvate Metabolism in Niemann-pick Type C1-deficient Murine Brain, " PLoS One 8(12):e82685, pp. 1-18, Public Library of Science, United States (Dec. 2013).

Kennedy, B.E., et al., "Presymptomatic Alterations in Amino Acid Metabolism and DNA Methylation in the Cerebellum of a Murine Model of Niemann-pick Type C Disease, " The American Journal of Pathology 186(6):1582-1597, Elsevier, United States (Jun. 2016).

Kimball, S.R., et al., "Leucine Regulates Translation of Specific mRNAs in L6 Myoblasts through mTOR-mediated Changes in Availability of eIF4E and Phosphorylation of Ribosomal Protein

(56) References Cited

OTHER PUBLICATIONS

S6," The Journal of Biological Chemistry 274(17):11647-11652, American Society for Biochemistry and Molecular Biology, United States (Apr. 1999).

Kirkegaard, T., et al., "Heat Shock Protein-based Therapy as a Potential Candidate for Treating the Sphingolipidoses," Science Translational Medicine 8(355):355ra118, American Association for the Advancement of Science, United States (Sep. 2016).

Klionsky, D.J., and Emr, S.D., "Autophagy as a Regulated Pathway of Cellular Degradation," Science 290(5497):1717-1721, American Association for the Advancement of Science, United States (Dec. 2000).

Lahde, A., et al., "Production of L-Leucine Nanoparticles Under Various Conditions Using an Aerosol Flow Reactor Method," Journal of Nanomaterials 2008:1-9, Hindawi Publishing Corporation, United Kingdom (Jun. 2008).

Liang, H., and Ward, W.F., "PGC-1alpha: A Key Regulator of Energy Metabolism," Advances in Physiology Education 30(4):145-151, American Physiological Society, United States (Dec. 2006).

Lloyd-Evans, E., and Platt, F.M., "Lipids on Trial: the Search for the Offending Metabolite in Niemann-Pick type C Disease," Traffic 11(4):419-428, John Wiley & Sons, United Kingdom (Apr. 2010).

Murphy, M.P., and Hartley, R.C., "Mitochondria as a Therapeutic Target for Common Pathologies," Nature Reviews Drug Discovery 17(12):865-886, Nature Pub. Group, United Kingdom (Dec. 2018).

Nagamori, S., et al., "Structure-activity Relations of Leucine Derivatives Reveal Critical Moieties for Cellular Uptake and Activation of mTORC1-mediated Signaling," Amino Acids 48(4):1045-1058, Springer-Verlag, Austria (Apr. 2016).

Neuzil, E., et al., "N-acetyl-DL-leucine, a Symptomatic Drug for Vertigo," Bulletin—societe De Pharmacie De Bordeaux 141(1-4):15-38, La Société, France (2002).

Neville, D.C., et al., "Analysis of Fluorescently Labeled Glycosphingolipid-derived Oligosaccharides Following Ceramide Glycanase Digestion and Anthranilic Acid Labeling," Analytical Biochemistry 331(2):275-282, Academic Press, United States (Aug. 2004).

Pankiv, S., et al., "P62/SQSTM1 Binds Directly to Atg8/LC3 to Facilitate Degradation of Ubiquitinated Protein Aggregates by Autophagy," The Journal of Biological Chemistry 282(33):24131-24145, American Society for Biochemistry and Molecular Biology, United States (Aug. 2007).

Patel, M.M. and Patel, B.M., "Crossing the Blood-Brain Barrier: Recent Advances in Drug Delivery to the Brain," CNS drugs 31(2):109-133, Springer International, New Zealand (Jan. 2017).

Patterson, M.C., et al., "Miglustat for treatment of Niemann-Pick C disease: a Randomised Controlled Study," The Lancet. Neurology 6(9):765-772, Lancet Pub. Group, United Kingdom (Sep. 2007).

Pentchev, P.G., et al., "A Lysosomal Storage Disorder in Mice Characterized by a Dual Deficiency of Sphingomyelinase and Glucocerebrosidase," Biochimica Et Biophysica Acta 619(3):669-679, Elsevier Pub. Co, Netherlands (Sep. 1980).

Pineda, M., et al., "Miglustat in Patients with Niemann-Pick Disease Type C (NP-C): a Multicenter Observational Retrospective Cohort Study," Molecular Genetics and Metabolism 98(3):243-249, Academic Press, United States (Nov. 2009).

Platt, F., and Strupp, M., "An Anecdotal Report by an Oxford Basic Neuroscientist: Effects of Acetyl-DL-leucine on Cognitive Function and Mobility in the Elderly," Journal of Neurology 263(6):1239-1240, Springer-Verlag, Germany (Jun. 2016).

Platt, F.M., "Emptying the Stores: Lysosomal Diseases and Therapeutic Strategies," Nature Reviews Drug Discovery 17(2):133-150, Nature Pub. Group, United Kingdom (Feb. 2018).

Platt, F.M., et al., "The Cell Biology of Disease: Lysosomal Storage Disorders: the Cellular Impact of Lysosomal Dysfunction," The Journal of Cell Biology 199(5):723-734, Rockefeller University Press, United States (Nov. 2012).

Pliss, L., et al., "Cerebral Developmental Abnormalities in a Mouse With Systemic Pyruvate Dehydrogenase Deficiency," PloS One 8(6):e67473, Public Library of Science, United States (Jun. 2013).

Priestman, D.A., et al., "N-butyldeoxynojirimycin Causes Weight Loss as a Result of Appetite Suppression in Lean and Obese Mice," Diabetes, Obesity and Metabolism 10(2):159-166, Wiley-Blackwell, United Kingdom (Feb. 2008).

Ruiz-Rodado, V., et al., "1h NMR-linked Metabolomics Analysis of Liver From a Mouse Model of NP-C1 Disease," Journal of Proteome Research 15(10):3511-3527, American Chemical Society, United States (Oct. 2016).

Sandhoff, L., and Harzer, K., "Gangliosides and Gangliosidoses: Principles of Molecular and Metabolic Pathogenesis," The Journal of Neuroscience 33(25):10195-10208, Society for Neuroscience, United States (Jun. 2013).

Sango, K., et al., "Mouse Models of Tay-sachs and Sandhoff Diseases Differ in Neurologic Phenotype and Ganglioside Metabolism," Nature Genetics 11(2):170-176, Nature Pub. Co, United States (Oct. 1995).

Son, S.M., et al., "Leucine Signals to mTORC1 Via Its Metabolite Acetyl-Coenzyme A," Cell Metabolism 29(1):192-201.e7, Cell Press, United States (Jan. 2019).

Stein, L.R., and Imai, S-I., "The Dynamic Regulation of NAD Metabolism in Mitochondria," Trends in Endocrinology and Metabolism 23(9):420-428, Elsevier Science Pub. Co, United States (Sep. 2012).

Strupp, M., et al., "Effects of Acetyl-dl-leucine in Patients with Cerebellar Ataxia: A Case Series," Journal of neurology, 260(10):2556-2561, Springer-Verlag, Germany (2013).

Te Vruchte, D., et al., "Relative Acidic Compartment vol. as a Lysosomal Storage Disorder-associated Biomarker," The Journal of Clinical Investigation 124(3):1320-1328, American Society for Clinical Investigation, United States (Mar. 2014).

Tighilet, B., et al., "Comparative Analysis of Pharmacological Treatments With N-acetyl-dl-leucine (Tanganil) and Its Two Isomers (N-acetyl-L-leucine and N-acetyl-D- leucine) on Vestibular Compensation: Behavioral Investigation in the Cat," European Journal of Pharmacology 769:342-349, Elsevier Science, Netherlands (Dec. 2015).

Vibert, N. and Vidal, P.P., "In Vitro Effects of Acetyl-dl-leucine(Tanganil) on Central Vestibular Neurons and Vestibulo-ocular Networks of the Guinea-pig, " The European Journal of Neuroscience 13(4):735-748, Wiley-Blackwell, France (Feb. 2001).

Williams, I.M., et al., "Improved Neuroprotection Using Miglustat, Curcumin and Ibuprofen as a Triple Combination Therapy in Niemann-pick Disease Type C1 Mice," Neurobiology of Disease 67:9-17, Academic Press, United States (Jul. 2014).

Yanagisawa, H., et al., "L-leucine and SPNS1 Coordinately Ameliorate Dysfunction of Autophagy in Mouse and Human Niemann-Pick type C disease," Scientific Reports 7(1):15944, Nature Publishing Group, United Kingdom (Nov. 2017).

Yanjanin, N.M., et al., "Linear Clinical Progression, Independent of Age of Onset, in Niemann-pick Disease, Type C," American Journal of Medical Genetics Neuropsychiatric Genetics 153B(1):132-140, Wiley-Blackwell, United States (Jan. 2010).

Yudkoff, M., "Brain Metabolism of Branched-chain Amino Acids," Glia 21(1):92-98, Wiley-Liss, United States (Sep. 1997).

Schniepp, R., et al., "Acetyl-DL-leucine improves gait variability in patients with cerebellar ataxia—a case series," Cerebellum Ataxias 3:8, BioMed Central, United Kingdom (Apr. 2016).

Wiederschain, G.Y., "The Metabolic and Molecular Bases of Inherited Disease," Biochemistry (Moscow) 67(5):611-612, Pleiades Publishing, Ltd., Russia (May 2002).

Abdulkhaleq, L.A., et al., "The Crucial roles of Inflammatory Mediators in Inflammation: A Review," Veterinary World 11(5):627-635, Veterinary World, India (May 2018).

Abel, L.A., et al., "Saccades in Adult Niemann-pick Disease Type C Reflect Frontal, Brainstem, and Biochemical Deficits," Neurology 72(12):1083-1086, Lippincott Williams & Wilkins, United States (Mar. 2009).

Aerts, J.M.F.G., et al., "Biomarkers in the Diagnosis of Lysosomal Storage Disorders: Proteins, Lipids, and Inhibodies," Journal of Inherited Metabolic Disease 34(3):605-619, Wiley, United States (Jun. 2011).

Akita, H., et al., "Creation of a Thermostable NADP?—dependent D-amino Acid Dehydrogenase from Ureibacillus Thermosphaericus

(56)         References Cited

OTHER PUBLICATIONS

Strain Al Meso-diaminopimelate Dehydrogenase by Site-directed Mutagenesis," Biotechnology Letters 34(9):1693-1699, Kluwer Academic Publishers, Netherlands (Sep. 2012).

Akita, H., et al., "Spectrophotometric Assay of D-isoleucine Using an Artificially Created D-amino Acid Dehydrogenase," Biotechnology Letters 36(11):2245-2248, Kluwer Academic Publishers, Netherlands (Nov. 2014).

Almanov, G.A., et al., "Structure of Free Radicals in Irradiated Acetyl-L-leucine Single Crystals at 77 K," Journal of Structural Chemistry 29(2):216-220, Plenum Publishing Corporation, United States (Mar.-Apr. 1988).

Almanov, G.A., et al., "Structure of Free Radicals in Irradiated Acetyl-L-leucine Single Crystals," Khimia Vysokikh Energii 20(5):430-435, Nauka, Union of Soviet Socialist Republics (Sep.-Oct. 1986).

Amor, S., et al., "Inflammation in Neurodegenerative Diseases—an Update," Immunology 142(2):151-166, Blackwell Scientific Publications, United Kingdom (Jun. 2014).

Angelini, C., et al., "Major Intra-familial Phenotypic Heterogeneity and Incomplete Penetrance Due to a CACNA1A Pathogenic Variant," European Journal of Medical Genetics 62(6):103530, Elsevier, Netherlands (Jun. 2019).

Antonenko, L.M., "The Second Congress International Academy of Dizziness," Neurological Journal 20(4):51-53, Federal State Autonomous Institution "National Medical Research Center for Children's Health" of the Ministry of Health of the Russian Federation, Russia (Dec. 2015).

Arbuthnott, K., and Frank, J., "Trail Making Test, Part B as a Measure of Executive Control: Validation Using a Set-switching Paradigm," Journal of Clinical and Experimental Neuropsychology 22(4):518-528, Routledge, United Kingdom (Aug. 2000).

Ashizawa, T., and Xia, G., "Ataxia," Continuum (Minneap Minn) 22(4 Movement Disorders):1208-1226, Wolters Kluwer, Netherlands (Aug. 2016).

August, R.A., et al., "Stereospecific Synthesis of (2S,4R)-[5,5,5-2H3]-leucine," Tetrahedron Letters 33:4617-4620, Elsevier, Netherlands (Aug. 1992).

Baci, D., et al., "Acetyl-L-Carnitine Downregulates Invasion (CXCR4/CXCL12, MMP-9) and Angiogenesis (VEGF, CXCL8) Pathways in Prostate Cancer Cells: Rationale for Prevention and Interception Strategies," Journal of Experimental & Clinical Cancer Research 38(1):464, pp. 1-17, BioMed Central, United Kingdom (Nov. 2019).

Battisti, C., et al., "Adult Onset Niemann-pick Type C Disease: A Clinical, Neuroimaging and Molecular Genetic Study," Movement Disorders 18(11):1405-1409, Wiley-Liss, United States (Nov. 2003).

Beaudin, M., et al., "Systematic Review of Autosomal Recessive Ataxias and Proposal for a Classification," Cerebellum and Ataxias 4:3, BioMed Central, United Kingdom (Feb. 2017).

Beck, A.T., et al., "An Inventory for Measuring Depression," Archives of General Psychiatry 4:561-571, American Medical Assn, United States (Jun. 1961).

Becker-Bense, S., et al., "P37. Effects of Acetyl-dl-leucine on the Cerebral Activation Pattern in Cerebellar Ataxia (FDG-PET Study)," Clinical Neurophysiology 126(8):e115, Elsevier, (Aug. 2015), 1 page.

Belarbi, K., et al., "TNF-a Protein Synthesis Inhibitor Restores Neuronal Function and Reverses Cognitive Deficits Induced by Chronic Neuroinflammation," Journal of Neuroinflammation 9:23, pp. 1-13, BioMed Central, United Kingdom (Jan. 2012).

Belikov, V.G., Pharmaceutical Chemistry: Manual, 4th edition, pp. 27-29, MEDpress-inform, Moscow, Russia (2007).

Benussi, A., et al., "Phenotypic Heterogeneity of Niemann-pick Disease Type C in Monozygotic Twins," Journal of Neurology 262(3):642-647, Springer-Verlag, Germany (Mar. 2015).

Beyer, L., et al., "Clinical Routine FDG-PET Imaging of Suspected Progressive Supranuclear Palsy and Corticobasal Degeneration: A Gatekeeper for Subsequent Tau-PET Imaging?" Frontiers in Neurology 9:483, pp. 1-9, Frontiers Research Foundation, Switzerland (Jun. 2018).

Bingham, A.L., et al., "Over one Hundred Solvates of Sulfathiazole," Chemical Communications, pp. 603-604, The Royal Society of Chemistry, United Kingdom (2001).

Bird, T.D., "Hereditary Ataxia Overview," in GeneReviews® (Internet), Adam, M.P., Ardinger H.H,, Pagon, R.A., et al., eds., pp. 1993-2020, University of Washington, Seattle, United States, Oct. 1998 (Updated Jul. 2019).

Brandt, T., et al., "Plasticity of the Vestibular System: Central Compensation and Sensory Substitution for Vestibular Deficits," Advances in Neurology 73:297-309, Lippincott Williams & Wilkins, United States (1997).

Bremova, T., et al., "Vestibular Function in Patients With Niemann-pick Type C Disease," Journal of Neurology 263(11):2260-2270, Springer-Verlag, Germany (Nov. 2016).

Bremova-Ertl, T., et al., "Clinical, Ocular Motor, and Imaging Profile of Niemann-pick Type C Heterozygosity," Neurology 94(16):e1702-e1715, Lippincott Williams & Wilkins, United States (Apr. 2020).

Bremova-Ertl, T., et al., "Oculomotor and Vestibular Findings in Gaucher Disease Type 3 and Their Correlation with Neurological Findings," Frontiers in Neurology 8:711, pp. 1-19, Frontiers Research Foundation, Switzerland (Jan. 2018).

Brendel, M., et al., "[18F]-THK5351 Pet Correlates with Topology and Symptom Severity in Progressive Supranuclear Palsy," Frontiers in Aging Neuroscience 9:440, pp. 1-12, Frontiers Research Foundation, Switzerland (Jan. 2018).

Caira, M.R., et al., "Preparation and Crystal Characterization of a Polymorph, a Monohydrate, and an Ethyl Acetate Solvate of the Antifungal Fluconazole," Journal of Pharmaceutical Sciences 93(3):601-611, Elsevier, United States (Mar. 2004).

Cardellicchio, C., et al., "Synthesis of a-amino Acid Derivatives by Copper(I)-catalyzed Conjugate Addition of Grignard Reagents to Methyl Acetamidoacrylate," Tetrahedron Letters 26(36):4387-4390, Pergamon Press Ltd, United Kingdom (May 1985).

Chakrabarti, S., et al., "Upregulation of Suppressor of Cytokine Signaling 3 in Microglia by Cinnamic Acid," Current Alzheimer Research 15(10):894-904, Bentham Science Publishers, United Arab Emirates (2018).

Chatterjee, B., et al., "Selective a-Deuteration of Amines and Amino Acids Using $D_2O$," Organic Letters 18(22):5892-5895, American Chemical Society, United States (Nov. 2016).

Chen, W-W., et al., "Role of Neuroinflammation in Neurodegenerative Diseases (Review)," Molecular Medicine Reports 13(4):3391-3396, D. A. Spandidos, Greece (Apr. 2016).

Cherry, J.D., et al., "Neuroinflammation and M2 Microglia: the Good, the Bad, and the Inflamed," Journal of Neuroinflammation 11:98, pp. 1-15, BioMed Central, United Kingdom (Jun. 2014).

Choi, K.D., and Choi, J.H., "Episodic Ataxias: Clinical and Genetic Features," Journal of Movement Disorders 9(3):129-135, Korean Movement Disorder Society, Korea (Sep. 2016).

Coccia, M., et al., "IL-1ß Mediates Chronic Intestinal Inflammation by Promoting the Accumulation of IL-17A Secreting Innate Lymphoid Cells and CD4(+) Th17 Cells," The Journal of Experimental Medicine 209(9):1595-609, Rockefeller University Press, United States (Aug. 2012).

Cupidi, C., et al., "Role of Niemann-Pick Type C Disease Mutations in Dementia," Journal of Alzheimer's Disease 55(3):1249-1259, SAGE Publications, United States (2017).

Davies, S.G., et al., "Asymmetric Conjugate Reductions with Samarium Diiodide: Asymmetric Synthesis of (2S,3R)- and (2S,3S)-[2-2H,3-2H]-leucine-(S)-phenylalanine Dipeptides and (2S,3R)-[2-(2)H,3-2H]-phenylalanine Methyl Ester," Organic Biomolecular Chemistry 3(8):1435-1447, Royal Society of Chemistry, United Kingdom (Apr. 2005).

Debray, F-G., et al., "Disorders of Mitochondrial Function," Current Opinion in Pediatrics 20(4):471-482, Lippincott Williams and Wilkins, United States (Aug. 2008).

Denier, C., et al., "High prevalence of CACNA1A Truncations and Broader Clinical Spectrum in Episodic Ataxia Type 2," Neurology 52(9):1816-1821, Wolters Kluwer, Netherlands (Jun. 1999).

Dieringer, N., "'Vestibular Compensation': Neural Plasticity and Its Relations to Functional Recovery After Labyrinthine Lesions in

(56)                    References Cited

OTHER PUBLICATIONS

Frogs and Other Vertebrates," Progress in Neurobiology 46(2-3):97-129, Pergamon Press, United Kingdom (Jun. 1995).

Disabato, D.J., et al., "Neuroinflammation: the Devil Is in the Details," Journal of Neurochemistry 139 Suppl 2(Suppl 2):136-153, Wiley on behalf of the International Society for Neurochemistry, United Kingdom (Oct. 2016).

Douglass, A., et al., "Behavioral Variant Frontotemporal Dementia Performance on a Range of Saccadic Tasks," Journal of Alzheimer's Disease 65(1):231-242, SAGE Publications, United States (2018).

Dyck, L.E., et al., "Effects of Deuterium Substitution on the Catabolism of Beta-Phenylethylamine: an in Vivo Study," Journal of Neurochemistry 46(2):399-404, Wiley, United Kingdom (Feb. 1986).

Dyson, G., et al., "The Mechanism of Action of Medicinal Substances," in Chemistry of Synthetic Drugs, pp. 12-19, Mir Publishers, Moscow, Union of Soviet Socialist Republics (1964).

Ehrensperger, M.M., et al., "Early Detection of Alzheimer's Disease With a Total Score of the German CERAD," Journal of the International Neuropsychological Society 16(5):910-920, Cambridge University Press, United Kingdom (Sep. 2010).

English language translation of Office Action for Russian Patent Application No. 2021119633, dated May 22, 2023, Federal Service for Intellectual Property, Moscow, Russia, 6 pages.

Fang, J., et al., "Dose Staggering as a Strategy to Reduce Drug—drug Interactions Due to Reversible Enzyme Inhibition Between Orally Administered Drugs With High First Pass Effect: A Computer Simulation Study," Biopharmaceutics & Drug Disposition 21(7):249-59, Wiley, United Kingdom (Oct. 2000).

Feil, K., et al., "Update on the Pharmacotherapy of Cerebellar Ataxia and Nystagmus," Cerebellum 15(1):38-42, Springer Nature, Germany (Feb. 2016).

Final Office Action for U.S. Appl. No. 17/247,757, mailed on May 5, 2023, 17 pages.

Fletcher, M.D., et al., "Three Approaches to the Synthesis of L-leucine Selectively Labelled with Carbon-13 or Deuterium in Either Diastereotopic Methyl Group ," Journal of the Chemical Society 43-52, 10 Pages, Royal Society of Chemistry, United Kingdom (Jan. 2000).

Frank-Cannon, T.C., et al., "Does Neuroinflammation Fan the Flame in Neurodegenerative Diseases?" Molecular Neurodegeneration 4:47, pp. 1-13, BioMed Central, United Kingdom (Nov. 2009).

Frankola, K.A., et al., "Targeting TNF-a to Elucidate and Ameliorate Neuroinflammation in Neurodegenerative Diseases," CNS & Neurological Disorders Drug Targets 10(3):391-403, Bentham Science Publishers, United Arab Emirates (May 2011), 25 pages.

Gandini, J., et al., "The Neurological Update: Therapies for Cerebellar Ataxias in 2020," Journal of Neurology 267(4):1211-1220, Springer Nature, Germany (Apr. 2020).

Giese, A.K., et al., "A Novel, Highly Sensitive and Specific Biomarker for Niemann-pick Type C1 Disease," Orphanet Journal of Rare Diseases 10:78, 8 Pages, BioMed Central, United Kingdom (Jun. 2015).

Ginger, M.L., et al., "The Biosynthetic Incorporation of the Intact Leucine Skeleton Into Sterol by the Trypanosomatid Leishmania Mexicana," The Journal of Biological Chemistry 276(15):11674-11682, Elsevier Inc, United States (Apr. 2001).

Gray, A.J., et al., "Olfactory Identification is Impaired in Clinic-based Patients With Vascular Dementia and Senile Dementia of Alzheimer Type," International Journal of Geriatric Psychiatry 16(5):513-517, John Wiley, United Kingdom (May 2001).

Greer, W.L., et al., "Mutations in NPC1 Highlight a Conserved NPC1-specific Cysteine-rich Domain," American Journal of Human Genetics 65(5):1252-1260, Cell Press, United States (Nov. 1999).

Griggs, R.C., et al., "Hereditary Paroxysmal Ataxia: Response to Acetazolamide," Neurology 28(12):1259-1264, Wolters Kluwer, Netherlands (Dec. 1978).

Gu, Y., et al., "Role of TNF in Mast Cell Neuroinflammation and Pain," Journal of Biological Regulators and Homeostatic Agents 29(4):787-791, Biolife, Italy (Oct.-Dec. 2015).

Guterman, E.L., et al., "Pearls & Oy-sters: Episodic Ataxia Type 2: Case Report and Review of the Literature," Neurology 86(23):e239-e241, Wolters Kluwer, Netherlands (Jun. 2016).

Habbas, S., et al., "Neuroinflammatory TNFa Impairs Memory via Astrocyte Signaling," Cell 163(7):1730-1741, Cell Press, United States (Dec. 2015).

Harzer, K., et al., "Niemann-pick Disease Type C: New Aspects in a Long Published Family—Partial Manifestations in Heterozygotes," JIMD Reports 12:25-29, Wiley, United States (2014).

Havla, J., et al., "Retinal Axonal Degeneration in Niemann-pick Type C Disease," Journal of Neurology 267(7):2070-2082, Springer-Verlag, Germany (Jul. 2020).

Heitz, C., et al., "Cognitive Impairment Profile in Adult Patients With Niemann Pick Type C Disease," Orphanet Journal of Rare Diseases 12(1):166, pp. 1-10, BioMed Central, United Kingdom (Oct. 2017).

Hill, R.K., et al., "Synthesis of (2S,4S)- and (2S,4R)-[5,5,5-$^2$H$_3$] Leucine from (R)-pulegone[1]," Canadian Journal of Chemistry 72(1):110-113 NRC Research Press, Canada (Jan. 1994).

Homer, R.J., et al., "The Use of Cystathionine Gamma-synthase in the Production of Alpha and Chiral Beta Deuterated Amino Acids," Analytical Biochemistry 215(2):211-215, Elsevier, United States (Dec. 1993).

Hong, H., et al., "Pathophysiological Role of Neuroinflammation in Neurodegenerative Diseases and Psychiatric Disorders," International Neurourology Journal 20(Suppl 1):S2-S7, Korean Continence Society, Korea (May 2016).

Hoyles, K., and Sharma, J.C., "Olfactory Loss as a Supporting Feature in the Diagnosis of Parkinson's Disease: A Pragmatic Approach," Journal of Neurology 260(12):2951-2958, Springer-Verlag, Germany (Dec. 2013).

Huang, H., et al., "Effects of Acetylleucine on the Recovery of Motor Balance and Discharge Activity of Neurons in the Medial Vestibular Nucleus in Rats after Labyrinthine Injury," Collection of Abstracts of the 21st National Congress and Academic Conference of the Chinese Physiological Society, Abstract 243, p. 66, Chinese Physiological Society, China (Oct. 2002).

Huang, J-Y., et al., "Neuroimaging Findings in a Brain with Niemann-pick Type C Disease," Journal of the Formosan Medical Association 110(8):537-542, Formosan Medical Association, Elsevier, Singapore (Aug. 2011).

Hummel, T., et al., "'Sniffin' Sticks': Olfactory Performance Assessed by the Combined Testing of Odor Identification, Odor Discrimination and Olfactory Threshold," Chemical Senses 22(1):39-52, Oxford University Press, United Kingdom (Feb. 1997).

Ilg, W., "Consensus Paper: Management of Degenerative Cerebellar Disorders," Cerebellum 13(2):248-268, Springer Nature, Germany (Apr. 2014).

Imbrici, P., et al., "Late-onset Episodic Ataxia Type 2 Due to an In-frame Insertion in CACNA1A," Neurology 65(6):944-946, Wolters Kluwer, Netherlands (Sep. 2005).

Inacio, A.R., et al., "Endogenous IFN-ß Signaling Exerts Anti-inflammatory Actions in Experimentally Induced Focal Cerebral Ischemia," Journal of Neuroinflammation 12:211, pp. 1-18, BioMed Central, United Kingdom (Nov. 2015).

International Search Report and Written Opinion for Application No. PCT/IB2019/060525, mailed on Feb. 3, 2020, 14 pages.

International Search Report and Written Opinion for Application No. PCT/IB2021/050236, mailed on Apr. 12, 2021, 10 pages.

International Search Report and Written Opinion for Application No. PCT/IB2021/054399, mailed on Aug. 18, 2021, 9 pages.

International Search Report and Written Opinion of International Application No. PCT/IB2020/051767, mailed on Jul. 30, 2020, 19 pages.

Isaacs, D.A., et al., "Case report of novel CACNA1A Gene Mutation Causing Episodic Ataxia Type 2," SAGE Open Medical Case Reports 5:1-3, SAGE Publications, United States (May 2017).

Jen, J., et al., "Clinical Spectrum of Episodic Ataxia Type 2," Neurology 62(1):17-22, Wolters Kluwer, Netherlands (Jan. 2004).

Jen, J.C., and Wan, J., "Episodic Ataxias," Handbook of Clinical Neurology 155:205-215, Elsevier, Netherlands (2018).

(56) References Cited

OTHER PUBLICATIONS

Jen, J.C., et al., "Primary Episodic Ataxias: Diagnosis, Pathogenesis and Treatment," Brain 130(Pt 10):2484-2493, Oxford University Press, United Kingdom (Oct. 2007).

Jeyakumar, M., et al., "Central Nervous System Inflammation is a Hallmark of Pathogenesis in Mouse Models of GM1 and GM2 Gangliosidosis," Brain 126(Pt 4):974-987, Oxford University Press, United Kingdom (Apr. 2003).

Johnen, A., et al., "Distinguishing Neurocognitive Deficits in Adult Patients With NP-C From Early Onset Alzheimer's Dementia," Orphanet Journal of Rare Diseases, 13(1):91, BioMed Central, United Kingdom (Jun. 2018).

Josephs, K.A., et al., "Heterozygous Niemann-Pick Disease type C Presenting with Tremor," Neurology 63(11):2189-2190, Lippincott Williams & Wilkins, United States (Dec. 2004).

Kalla, R., and Strupp, M., "Aminopyridines and Acetyl-DL-leucine: New Therapies in Cerebellar Disorders," Current Neuropharmacology 17(1):7-13, Bentham Science Publishers, United Arab Emirates (Jan. 2019).

Karve, I.P., et al., "Ablation of Type-1 IFN Signaling in Hematopoietic Cells Confers Protection Following Traumatic Brain Injury," eNeuro 3(1):ENEURO.0128-15, Society for Neuroscience, United States (Feb. 2016).

Kelly, N.M., et al., "Chemo-enzymatic Synthesis of Isotopically Labelled L-valine, L-isoleucine and Allo-isoleucine," Tetrahedron Letters 37(9):1517-1520, Elsevier, United Kingdom (Feb. 1996).

Kelly, N.M., et al., "Methods for the Synthesis of L-Leucine Selectively Labelled with Carbon-13 or Deuterium in either Diastereotopic Methyl Group," Tetrahedron Letters 36:8315-8318, Elsevier, United Kingdom (Nov. 1995).

Kelly, N.M., et al., "Syntheses of Amino Acids Incorporating Stable Isotopes," Nat Prod Rep 14:205-219, Royal Society of Chemistry, United Kingdom (Jan. 1997).

Khelimsky, A.M., et al., *Clinic Picture, Diagnosis and Treatment of Cranio-Brain Injuries*, pp. 22-24 (2003), 8 pages.

Kim, J.M., et al., "Episodic Ataxia Type 2 due to a Deletion Mutation in the CACNA1A Gene in a Korean Family," Journal of Clinical Neurology 2(4):268-271, Korean Neurological Association, Korea (Dec. 2006).

Kinney, C.R., and Adams, R., "Dideuteriovaline and Dideuterioleucine," Journal of the American Chemical Society 59(5):897-898, American Chemical Society, United States (May 1937).

Kipfer, S., and Strupp, M., "The Clinical Spectrum of Autosomal-Dominant Episodic Ataxias," Movement Disorder Clinical Practice 1(4):285-290, Wiley, United States (Jul. 2014).

Kluenemann, H.H., et al., "Parkinsonism Syndrome in Heterozygotes for Niemann-Pick C1," Journal of the Neurological Sciences, 335(1-2): 219-220, Elsevier, Netherlands (Dec. 2013).

Kresojevic, N., et al., "Mutations in Niemann Pick Type C Gene Are Risk Factor for Alzheimer's Disease," Medical Hypotheses 83:559-562, Elsevier, United States (Nov. 2014).

Kumar, A., and Chungani, H.T., "Niemann-Pick Disease Type C: Unique 2-Deoxy-2,[18F] Fluoro-D-Glucose PET Abnormality," Pediatric Neurology, 44(1): 57-60, Elsevier, Netherlands (Jan. 2011).

Kummerer, K., "Pharmaceuticals in the Environment," Annual Review of Environment and Resources 35:57-75, Annual Reviews, United States (Aug. 2010).

Lappalainen, U., et al., "Interleukin-1beta Causes Pulmonary Inflammation, Emphysema, and Airway Remodeling in the Adult Murine Lung," American Journal of Respiratory Cell and Molecular Biology 32(4):311-318, American Thoracic Society, United States (Apr. 2005).

Lee, J.H., et al., "Anti-inflammatory and Anti-genotoxic Activity of Branched Chain Amino Acids (BCAA) in Lipopolysaccharide (LPS) Stimulated Raw 264.7 Macrophages," Food Science and Biotechnology 26(5):1371-1377, Korean Society of Food Science and Technology, Korea (Aug. 2017).

Liu, S.Q., et al., Leucine Alters Immunoglobulin a Secretion and Inflammatory Cytokine Expression Induced by Lipopolysaccharide via the Nuclear Factor-kb Pathway in Intestine of Chicken Embryos, Animal : an International Journal of Animal Bioscience 12(9):1903-1911, Elsevier, United Kingdom (Sep. 2018).

Lobato, J.B., et al., "Biomarkers in Lysosomal Storage Diseases," Diseases 4(4):40, 17 Pages, MDPI AG, Switzerland (Dec. 2016).

Luppa, M., et al., "Age-related predictors of institutionalization: results of the German study on ageing, cognition and dementia in primary care patients (AgeCoDe)," Social Psychiatry and Psychiatric Epidemiology 47(2):263-270, Springer International, Germany (Feb. 2012).

Maksemous, N., et al., "Next-generation Sequencing Identifies Novel CACNA1A Gene Mutations in Episodic Ataxia Type 2," Molecular Genetics and Genomic Medicine 4(2):211-222, Wiley, United States (Jan. 2016).

Mantuano, E., et al., "Identification of Novel and Recurrent CACNA1A Gene Mutations in Fifteen Patients with Episodic Ataxia Type 2," Journal of Neurological Sciences 291(1-2):30-36, Elsevier, Netherlands (Apr. 2010).

Miyanoiri, Y., et al., "Differential Isotope-labeling for Leu and Val Residues in a Protein by *E. coli* Cellular Expression Using Stereospecifically Methyl Labeled Amino Acids," Journal of Biomolecular NMR 57(3):237-249, Springer, Netherlands (Nov. 2013).

Moss, G.P., "Basic Terminology of Stereochemistry," Pure and Applied Chemistry 68(12):2193-2222, IUPAC, United Kingdom (1996).

Nakajima, N., et al., "Enzymatic Conversion of Racemic Methionine to the L-enantiomer," Journal of the Chemical Society 13:947-948, Royal Society of Chemistry, United Kingdom (1990).

Niyazov, D.M., et al., "Primary Mitochondrial Disease and Secondary Mitochondrial Dysfunction: Importance of Distinction for Diagnosis and Treatment," Molecular Syndromology 7(3):122-137, S. Karger, Switzerland (Jul. 2016).

Non-Final Office Action for U.S. Appl. No. 17/247,757, mailed on Oct. 4, 2023, 16 pages.

Non-Final Office Action for U.S. Appl. No. 17/247,757, mailed on Oct. 6, 2022, 14 pages.

Notice of Allowance for U.S. Appl. No. 17/247,757, mailed on Apr. 10, 2024, 13 pages.

Oba, M., et al., "Stereoselective Deuterium-labelling of Diastereotopic Methyl and Methylene Protons of L-leucine," Tetrahedron Letters 39:1595-1598, Elsevier, Netherlands (Mar. 1998).

Oba, M., et al., "Synthesis of (13)C/D Doubly Labeled L-leucines: Probes for Conformational Analysis of the Leucine Side-chain," The Journal of Organic Chemistry 66(17):5919-5922, American Chemical Society, United States (Aug. 2001).

Oba, M., et al., "Synthesis of L-threo- and L-erythro-[1-$^{13}$C, 2,3-$^2$H$_2$] Amino Acids: Novel Probes for Conformational Analysis of Peptide Side Chains" Journal of the Chemical Society 12:1603-1609, Royal Society of Chemistry, United Kingdom (1995).

Olichney, J.M., et al., "Anosmia is Very Common in the Lewy Body Variant of Alzheimer's Disease," Journal of Neurology, Neurosurgery, and Psychiatry 76(10): 1342-1347, BMJ Publishing Group, United Kingdom (Oct. 2005).

Ophoff, R.A., et al., "Familial Hemiplegic Migraine and Episodic Ataxia Type-2 Are Caused by Mutations in the Ca2+ Channel Gene CACNL1A4," Cell 87(3):543-552, Cell Press, United States (Nov. 1996).

Orasji, S.S.S., et al., "Olfactory Dysfunction in Behavioral Variant Frontotemporal Dementia," Clinical Neurology and Neurosurgery, 141:106-110, Elsevier, Netherlands (Feb. 2016).

Oxbridge Solutions Limited, "Acetylation of drugs," GPnotebook, published on Jan. 1, 2018, accessed at https://gpnotebook.com/pages/surgery/acetylation-of-drugs, accessed on Feb. 26, 2025, 2 Pages.

Patterson, M.C., et al., "Disease and Patient Characteristics in NP-C Patients: Findings From an International Disease Registry," Orphanet Journal of Rare Diseases, 8:12, 10 pages, BioMed Central, United Kingdom (Jan. 2013).

Patterson, M.C., et al., "Long-term Miglustat Therapy in Children With Niemann-Pick Disease Type C," Journal of Child Neurology, 25(3): 300-305, Sage Publications, United States (Mar. 2010).

(56) References Cited

OTHER PUBLICATIONS

Patterson, M.C., et al., "Recommendations for the Detection and Diagnosis of Niemann-Pick Disease Type C: An update," Neurology: Clinical Practice, 7: 499-511, Lippincott Williams and Wilkins, United States (Dec. 2017).

Patterson, M.C., et al., "Recommendations for the Diagnosis and Management of Niemann-Pick Disease Type C: An update," Molecular Genetics and Metabolism 106(3):330-344, Academic Press, United States (Jul. 2012).

Pelz, J.O., et al., "Failure to Confirm Benefit of Acetyl-dl-leucine in Degenerative Cerebellar Ataxia: A Case Series," Journal of Neurology, 262(5):1373-1375, Springer- Verlag, Germany (2015).

Penkava, J., et al., "A Novel Pathogenic CACNA1A Variant Causing Episodic Ataxia Type 2 (EA2) Spectrum Phenotype in Four Family Members and a Novel Combined Therapy," Journal of Neurology 267(Suppl 1):181-184, Springer Nature, Germany (Dec. 2020).

Postuma, R.B., and Berg, D., et al., "Advances in Markers of Prodromal Parkinson Disease," Nature Reviews Neurology, 12(11): 622-634, Nature Publishing Group, United Kingdom (Oct. 2016).

Pretegiani, E., and Optican, M.L., "Eye Movements in Parkinson's Disease and Inherited Parkinsonian Syndromes," Frontiers in Neurology 8:592, Frontiers Research Foundation, Switzerland (Nov. 2017).

Probert, F., et al., "NMR Analysis Reveals Significant Differences in the Plasma Metabolic Profiles of Niemann Pick C1 Patients, Heterozygous Carriers, and Healthy Controls," Scientific Reports 7(1):6320, Nature Publishing Group, United Kingdom (Jul. 2017).

Pubchem, "Acetylleucine," CID 1995, accessed at https://pubchem. ncbi.nlm.nih.gov/compound/1995#section= 2D-Structure, 3 pages.

Ray, K.K., "Interleukin-1 Revisited: Further Insights Into Its Role in Atherosclerosis and as a Potential Therapeutic Target for Treatment," Journal of the American College of Cardiology 63(17):1735-1738, Elsevier Biomedical, United States (May 2014).

Ren, K., and Torres, R., "Role of Interleukin-1beta during Pain and Inflammation," Brain Research Reviews 60(1):57-64, Elsevier B.V., Netherlands (2009).

Reunert, J., et al., "Niemann-Pick Type C-2 Disease: Identification by Analysis of Plasma Cholestane-3ß, 5a, 6ß-Triol and Further Insight into the Clinical Phenotype," JIMD Reports 23:17-26, Wiley, United States (Mar. 2015).

Riant, F., et al., "Ataxies Episodiques Genetiques [Hereditary Episodic Ataxia]," Revue Neurologique 167(5):401-407, Elsevier, Netherlands (May 2011).

Richards, S., et al., "Standards and Guidelines for the Interpretation of Sequence Variants: a Joint Consensus Recommendation of the American College of Medical Genetics and Genomics and the Association for Molecular Pathology," Genetics in Medicine 17(5):405-424, Elsevier, Netherlands (May 2015).

Rose, J.E., et al., "Stereospecific Synthesis of a-Deuteriated a-Amino Acids: Regiospecific Deuteriation of Chiral 3-Isopropyl-2,5-Dimethoxy-3,6-Dihydropyrazines," Journal of the Chemical Society 2:157-165, Royal Society of Chemistry, United Kingdom (1995).

Royall, D.R., et al., "CLOX: an Executive Clock Drawing Task," Journal of Neurology, Neurosurgery, and Psychiatry 64(5): 588-594, BMJ Publishing Group, United Kingdom (May 1998).

Rozenbaum, H., "How to Evaluate the Risk-benefit Ratio of the Low-dose Hormone Replacement Therapy?" The Journal of Steroid Biochemistry and Molecular Biology 102(1-5):256-260, Pergamon, United Kingdom (Dec. 2006).

Sanchez-Cubillo, I., et al., "Construct Validity of the Trail Making Test: Role of Task-switching, Working Memory, Inhibition/ interference Control, and Visuomotor Abilities," Journal of the International Neuropsychological Society, 15(3): 438-450, Cambridge University Press, United Kingdom (May 2009).

Sarkar, C., et al., "Impaired Autophagy Flux is Associated With Neuronal Cell Death After Traumatic Brain Injury," Autophagy 10(12):2208-2222, Taylor & Francis, United States (2014).

Sarkar, C., et al., "N-acetyl-L-leucine Treatment Attenuates Neuronal Cell Death and Suppresses Neuroinflammation After Traumatic Brain Injury in Mice," bioRxiv, pp. 1-20, accessed at https://www. biorxiv.org/content/10.1101/759894v1.full.pdf, accessed on Sep. 8, 2019.

Sarkar, C., et al., "PLA2G4A/cPLA2-Mediated Lysosomal Membrane Damage Leads to Inhibition of Autophagy and Neurodegeneration After Brain Trauma," Autophagy 16(3):466-485, Taylor & Francis, United States (Mar. 2020).

Scaglione, C., et al., "REM Sleep behaviour Disorder in Parkinson's Disease: A Questionnaire-based Study," Neurological Sciences: Official Journal of the Italian Neurological Society and of the Italian Society of Clinical Neurophysiology 25(6):316-321, Springer-Verlag Italia, Italy (Feb. 2005).

Schneider, E., et al., "EyeSeeCam: An Eye Movement-Driven Head Camera for the Examination of Natural Visual Exploration," Annals of the New York Academy of Sciences 1164:461-467, New York Academy of Sciences, United States (May 2009).

Schneider, S., "Do Heterozygous Mutations of Niemann-Pick Type C Predispose to Late-onset Neurodegeneration: A Review of the Literature," Journal of Neurology 268(6):2055-2064, Springer-Verlag, Germany (Jun. 2021).

Sevin, M., et al., "The Adult Form of Niemann-Pick Disease Type C," Brain: A Journal of Neurology 130: 120-133, Oxford University Press, United Kingdom (Jan. 2007).

Shah, S.A., et al., "Enantiomeric Conversion of Racemic Amino Acid Mixtures via an Oxidase-Aminotransferase Coupled System," Tetrahedron Letters 35:29-32, Elsevier, United Kingdom (Jan. 1994).

Shao, L., and Hewitt, M.C., "The Kinetic Isotope Effect in the Search for Deuterated Drugs," Drug News & Perspectives 23(6)398-404, Thomson Reuters, United States (Jul.-Aug. 2010).

Shibanuma, M., et al., "Inhibition by N-acetyl-L-cysteine of Interleukin-6 mRNA Induction and Activation of NF Kappa B by Tumor Necrosis Factor Alpha in a Mouse Fibroblastic Cell Line, Balb/3T3," FEBS Letters 353(1):62-66, John Wiley & Sons Ltd, United Kingdom (Oct. 1994).

Sidransky, E., et al., "Multicenter Analysis of Glucocerebrosidase Mutations in Parkinson's Disease," The New England Journal of Medicine 361(17):1651-1661, Massachusetts Medical Society, United States (Oct. 2009).

Simonaro, C.M., "Lysosomes, Lysosomal Storage Diseases, and Inflammation," Journal of Inborn Errors of Metabolism & Screening 4:1-8, Latin American Society of Inborn Errors of Metabolism and Newborn Screening, Uruguay (2016).

Sintas, C., et al., "Mutation Spectrum in the CACNA1A Gene in 49 Patients with Episodic Ataxia," Scientific Reports 7(1):2514, Springer Nature, Germany (May 2017).

Stiasny-Kolster, K., et al., "The REM Sleep Behavior Disorder Screening Questionnaire—A New Diagnostic Instrument," Movement Disorders 22(16):2386-2393, Wiley-Liss, United States (Dec. 2007).

Strupp, M., et al., "A Randomized Trial of 4-Aminopyridine in Ea2 and Related Familial Episodic Ataxias," Neurology 77(3):269-275, Wolters Kluwer, United States (Jul. 2011).

Strupp, M., et al., "Fampridine and Acetazolamide for the Treatment of Episodic Ataxia Type 2 Eat2treat): a Randomised, Double-blind, Placebo-controlled, Three-period Crossover Trial (2331)," Neurology 94(15_supplement): Abstract 2331, Wolters Kluwer, United States (Apr. 2020).

Strupp, M., et al., "Treatment of Episodic Ataxia Type 2 with the Potassium Channel Blocker Aminopyridine," Neurology 62(9):1623-1625, Wolters Kluwer, United States (May 2004).

The Definition of "Disease Prevention", accessed from Free Dictionary Web, Retrieved from Internet URL: https://web.archive.org/ web/20150910204016/https://medical-dictionary.thefreedictionary. com/Prevention+(medical), 2 Pages (Sep. 2018).

Timmins, G.S., "Deuterated Drugs: Where Are We Now?" Expert Opinion on Therapeutic Patents 24(10):1067-1075, Taylor & Francis, United Kingdom (Oct. 2014).

Tuttolomondo, A., et al., "Studies of Selective TNF Inhibitors in the Treatment of Brain Injury from Stroke and Trauma: a Review of the Evidence to Date," Drug Design, Development and Therapy 8:2221-2238, Dove Press Limited, New Zealand (Nov. 2014).

(56)           References Cited

OTHER PUBLICATIONS

Upson, D.A., and Hruby, V.J., "A General Method for the Preparation of Alpha-labeled Amino Acids," The Journal of Organic Chemistry 42(13):2329-2330, American Chemical Society, United States (Jun. 1977).

Van Tonder, E.C., et al., "Preparation and Physicochemical Characterization of 5 Niclosamide Solvates and 1 Hemisolvate," AAPS PharmSciTech 5(1):E12, pp. 1-10, Springer, United States (Feb. 2004).

Written Opinion of International Preliminary Examining Authority of International Application No. PCT/IB2021/050236, European Patent Office, Netherlands, mailed on Dec. 17, 2021, 7 pages.

Xu, H., and Ren, D., "Lysosomal Physiology," Annual Review of Physiology 77:57-80, Annual Reviews, United States (2015).

Yamauchi, N., and Endoh, S., "IMproved Isotopic Deuterium Labeling at the Diastereotopic Methyl Group of Leucine: a Synthetic Route to (4S)- and (4R)-[5-$^2$H$_1$] Leucine," Bioscience, Biotechnology, and Biochemistry 70(1):276-278, Oxford University Press, United Kingdom (Jan. 2006).

Yu, W., et al., "Neurodegeneration in Heterozygous Niemann-Pick type C1 (NPC1) Mouse: Implication of Heterozygous NPC1 Mutations Being a Risk for Tauopathy," The Journal of Biological Chemistry 280(29): 27296-27302, American Society for Biochemistry and Molecular Biology, United States (Jul. 2005).

Yuan, S.S., and Ajami, A.M., "Trideuteromethyl Labeled Leucine and Valine," Hua Xue—Chemistry 49(4):257-260, Zhonggguo Huaxuehui, Taiwan (Dec. 1991).

Zech, M., et al., "Niemann-Pick C Disease Gene Mutations and Age-Related Neurodegenerative Disorders," PLoS One, 8(12): e82879, Public Library of Science, United States (Dec. 2013).

Zwergal A., et al., "Sequential [(18)F]FDG µPET Whole-brain Imaging of Central Vestibular Compensation: A Model of Deafferentation-induced Brain Plasticity," Brain Structure and Function, 221(1):159-170, Springer-Verlag, Germany (2016).

PCT Application No., PCT/US2025/015918, inventors Billington, I.M., et al., filed on Feb. 14, 2025, 58 pages (Not yet Published).

PCT Application No., PCT/US2025/034430, inventors Factor, M., et al., filed on Jun. 20, 2025, 106 pages (Not yet Published).

Armstrong, C., "AAN/AHS Update Recommendations for Migraine Prevention in Adults," American Family Physician 87(8):584-585, American Academy of General Practice, United States (2013).

Bartleson, J.D. and Cutrer F. M., "Migraine Update Diagnosis and Treatment," Minnesota Medicine 93(5):36-41, Minnesota Medical Assn, United States (May 2010).

Buchfuhrer, M.J., "Strategies for the Treatment of Restless Legs Syndrome," Neurotherapeutics 9(4):776-790, Springer, United States (Oct. 2012).

Bose, P. and Goadsby, P.J., "The Migraine Postdrome," Current Opinion in Neurology 29(3):299-301, Lippincott Williams & Wilkins, United Kingdom (Jun. 2016).

Buzzi, M.G., et al., "Prodromes and the Early Phase of the Migraine Attack: Therapeutic Relevance," Functional neurology 20(4):179-183, CIC Edizioni Internazionali, Italy (Oct.-Dec. 2005).

Colman, I., et al., "Parenteral Dexamethasonefor Acute Severe Migraine Headache: Meta-analysis of Randomised Controlled Trials for Preventing Recurrence," BMJ (Clinical research ed.) 336(7657):1359-1361, British Medical Association, United Kingdom (Jun. 2008).

Derry, S., et al., "Diclofenac with or without an Antiemetic for Acute Migraine Headaches in Adults," The Cochrane Database of Systematic Reviews 2013(4): CD008783, Wiley, United Kingdom (Apr. 2013), 43 Pages.

Ferber-Viart, C., et al., "Effects of Acetyl-dl-leucine in Vestibular Patients: A Clinical Study Following Neurotomy and Labyrinthectomy," Audiology and Neuro-otology 14(1):17-25, Karger, Switzerland (2009).

Gilmore, B. and Michael, M., "Treatment of Acute Migraine Headache," American family physician, 83(3):271-280, American Academy of General Practice, United States (2011).

Headache Classification Subcommittee of the International Headache Society, The International Classification of Headache Disorders: 2nd edition, Cephalalgia 24(Suppl 1):150 pages, Sage, United Kingdom (2004).

Kelman, L., "The Postdrome of the Acute Migraine Attack," Cephalalgia: An International Journal of Headache 26(2):214-220, Blackwell Publishing Ltd, United Kingdom (Feb. 2006).

Kirthi, V., et al., "Aspirin with or without an Antiemetic for Acute Migraine Headaches in Adults," The Cochrane database of systematic reviews 2013(4):CD008041, Wiley, United Kingdom (2010).

Lempert, T., et al., "Vestibular Migraine: Diagnostic Criteria," Journal of Vestibular Research: Equilibrium & Orientation 22(4):167-172, SAGE Publications, United States (2012).

Ory, D.S., et al., "Intrathecal 2-hydroxypropyl-ß-cyclodextrin Decreases Neurological Disease Progression in Niemann-Pick Disease, Type C1: a Non-randomised, Open-label, Phase 1-2 Trial," Lancet 390(10104):1758-1768, Elsevier, United Kingdom (Oct. 2017).

Rabbie, R., et al., "Ibuprofen with or without an Antiemetic for Acute Migraine Headaches in Adults," The Cochrane database of systematic reviews 6:(10):CD008039, Wiley, United Kingdom (Oct. 2010).

Rae-Grant., [edited by] Lynn, J.D., et al., "The 5-Minute Neurology Consult, 2nd Edition," Lippincott Williams & Wilkins, Philadelphia, p. 26 (2004).

Rossi, P., et al., "Prodromes and Predictors of Migraine Attack," Functional Neurology 20(4):185-191, CIC Edizioni Internazionali, Italy (Oct.-Dec. 2005).

Ropper, A.H. and Samuels, M.A., "Adam's and Victor's Principles of Neurology," 9th Edition, Chapter 10, Mc Graw Hill Education, New York (2009).

Wheeler, S., and Sillence, D.J., "Niemann-Pick type C Disease: Cellular Pathology and Pharmacotherapy," Journal of Neurochemistry 153(6):674-692, Wiley on behalf of the International Society for Neurochemistry, United Kingdom (Jun. 2020).

Tepper, S.J. and Tepper D.E., "Breaking the Cycle of Medication Overuse Headache," Cleveland Clinic Journal of Medicine, 77(4):236-242, Cleveland Clinic Educational Foundation, United States (2010).

Domitrz, I., et al., "Changes in Serum Amino Acids in Migraine Patients without and with Aura and their Possible Usefulness in the Study of Migraine Pathogenesis," CNS and Neurological Disorders Drug Targets, 14(3):345-349, Bentham Science Publishers, United Arab Emirates (2015).

Salzman, B., et al., "Gait and Balance Disorders in Older Adults," American Family Physician 82(1):61-68, American Academy of General Practice, United States (Jul. 2010).

Jahn, K., et al., "Dizziness and Unstable Gait in Old Age: Etiology, Diagnosis and Treatment," German Medical Journal International 112(23):387-393, German Doctors Publishing House, Germany (Jun. 2015).

Abe, et al., "Medium-Chain Triglycerides in Combination with Leucine and Vitamin D Increase Muscle Strength and Function in Frail Elderly Adults in a Randomized Controlled Trial" The Journal of Nutrition 146(5):1017-1026, Elsevier, United States (May 2016).

Iwasaki, S., and Yamasobaet, T., "Dizziness and Imbalance in the Elderly: Age-related Decline in the Vestibular System," Aging and Disease 6(1):38-47, JKL International, United States (Feb. 2014).

Brueggemann, A., et al., "Effects of Acetyl-DL-Leucine on Ataxia and Downbeat-Nystagmus in Six Patients With Ataxia Telangiectasia," Journal of Child Neurology 37(1):20-27, Sage, United States (Jan. 2022).

Davis, O.B., et al., "NPC1-mTORC1 Signaling Couples Cholesterol Sensing to Organelle Homeostasis and Is a Targetable Pathway in Niemann-Pick Type C," Developmental Cell 56(3):260-276, Cell Press, United States (Feb. 2021).

Churchill, G.C., et al., "Acetylation Turns Leucine Into a Drug by Membrane Transporter Switching," Scientific Reports 11(1):15812, pp. 1-10, Nature Publishing Group, United Kingdom (Aug. 2021).

Auer, I.A., et al., "Paired Helical Filament Tau (PHFtau) in Niemann-pick Type C Disease is Similar to PHFtau in Alzheimer's Disease," Acta Neuropathologica 90(6):547-551, Springer Verlag, Germany (1995).

(56) References Cited

OTHER PUBLICATIONS

Nixon, R.A., "Niemann-Pick Type C Disease and Alzheimer's Disease: The APP-endosome Connection Fattens Up," The American Journal of Pathology 164(3):757-761, Elsevier, United States (Mar. 2004).

Castellano, B.M., et al., "Lysosomal Cholesterol Activates Mtorc1 via an Slc38a9-niemann-pick C1 Signaling Complex," Science 355(6331):1306-1311, American Association for the Advancement of Science, United States (Mar. 2017).

English Translation of Decision of Refusal issued in related Japanese Application No. 2021-164793, dated Apr. 25, 2023, 3 pages.

English Translation of Notice of Reason for Refusal issued in related Japanese Application No. 2021-164793, dated Sep. 29, 2022, 4 pages.

English Translation of Notice of Final Rejection issued in related Korean Application No. KR 10-2022-7021012, dated Apr. 3, 2023, 4 pages.

Communication from the European Patent Office issued in related EP Application No. 19174007.5, mailed Nov. 26, 2019, 5 pages.

English Translation of The Second Office Action issued in related Chinese Application No. CN 201780059708.6, dated Dec. 15, 2021, 4 pages.

English Translation of The First Office Action issued in related Chinese Application No. CN 201780059708.6, dated Jul. 29, 2021, 5 pages.

English Translation of Search Report issued by the Registered Search Organization in related Japanese Application No. JP 2019-507819, dated Apr. 2, 2021, 14 pages.

English Translation of Written Opinion issued in related Japanese Application No. JP 2019-507819, dated Aug. 11, 2021, 5 pages.

English Translation of Notice of Reasons for Refusal issued in related Application No. JP 2019-507819, dated Apr. 27, 2021, 4 pages.

Lukas, J., et al., "Enzyme Enhancers for the Treatment of Fabry and Pompe Disease," Molecular Therapy 23(3):456-464, Cell Press, United States (Mar. 2015).

Reagan-Shaw, S., et al., "Dose translation from animal to human studies revisited," FASEB journal 22(3):659-661, Federation of American Societies for Experimental Biology, United States (Mar. 2008).

Bremova, T., "Niemann-pick Type C: Effects of a Therapy With Acetyl-dl-leucine and Vestibular Function," Disseration for Graduate School Systemic Neurosciences Der Ludwig-maximilians-universitat Munchen. Presented Orally to the Public on Sep. 19, 2016 (2016), 93 Pages.

English Translation of Japanese Office Action in Counterpart Application No. 2019- 507811 dated Apr. 27, 2021, 4 pages.

English Translation of Search Report in Chinese Application No. 201780062740X, dated Aug. 14, 2021, 1 page.

Search Report in Russian Application No. 2019106493, dated Oct. 26, 2020 with English Translation.

Olesen, J., et al., "The International Classification of Headache Disorders, 3rd Edition (Beta Version)," Cephalalgia 33(9):629-808, Sage, United Kingdom (Jul. 2013).

English language Translation of Pertinent Portion of Office Action for Japanese Patent Application No. 2020-519196, dated Apr. 26, 2022, 5 pages.

Dos Santos, A.B., et al., "Treatment of Sleeping Disorders Should Be Considered in Clinical Management of Parkinson's Disease," Frontiers in Aging Neuroscience 6:273, Frontiers Research Foundation, Switzerland (Oct. 2014).

Murofushi, T., "Migraine Associated Vertigo," Equilibrium Research 70(3): 172-175, Japan Society for Equilibrium Research, Japan (2011).

Kurokawa, K., et al., "Migraine and Vertigo: Introduction to Migrainous Vertigo," Journal of Clinical and Experimental Medicine 255(7):757-761, Springer, Switzerland (2015).

Fernandez, M., et al., "Pharmacological agents for the prevention of vestibular migraine," The Cochrane Database of Systematic Reviews 2015(6):CD010600, Wiley, United Kingdom (Jun. 2015).

Velazquez-Perez, L., et al., "Lisuride Reduces Involuntary Periodic Leg Movements in Spinocerebellar Ataxia Type 2 Patients," Cerebellum (London, England) 11(4):1051-1056, Springer, United States (Dec. 2012).

Porter, V.R., et al., "Sleep, Cognition and Dementia," Current Psychiatry Reports 17(12):1-11, Current Science, United States (Oct. 2015).

Suzuki, K., et al., "Sleep Disturbances in Neurodegenerative Diseases," Nihon Naika Gakkai zasshi. The Journal of the Japanese Society of Internal Medicine 106(2):309-318, Nihon Naika Gakkai, Japan (Feb. 2017).

English Translation of Office Action for Japanese Patent Application No. 2020-521938, mailed on Apr. 1, 2022, 3 Pages.

Abe, S., et al., "Medium-Chain Triglycerides in Combination with Leucine and Vitamin D Benefit Cognition in Frail Elderly Adults: A Randomized Controlled Trial," Journal of Nutritional Science and Vitaminology 63(2):133-140, University of Tokyo Press, Japan (2017).

Dehay, B., et al., "Lysosomal Impairment in Parkinson's Disease," Movement Disorders 28(6):725-732, Wiley-Liss, United States (Jun. 2013).

Xu, J., et al., "Cholesterol Trafficking Is Required for mTOR Activation in Endothelial Cells," Proceedings of the National Academy of Sciences of the United States of America 107(10):4764-4769, National Academy of Sciences, United States (Mar. 2010).

Oldendorf, W.H., "Stereospecificity of Blood-brain Barrier Permeability to Amino Acids," The American Journal of Physiology 224(4):967-969, American Physiological Society, United States (Apr. 1973).

Shemesh, A., et al., "Suppression of mTORC1 Activation in Acid—Glucosidase-deficient Cells and Mice Is Ameliorated by Leucine Supplementation," American Journal of Physiology. Regulatory, Integrative and Comparative Physiology 307(10):R1251-R1259, American Physiological Society, United States (Nov. 2014).

Patterson, M., et al., "Niemann-Pick Disease Type C," in GeneReviews® [Internet], Adam, M.P., et al., eds., 2 pages, University of Washington, Seattle, United States (Dec. 10, 2020).

Stiasny-Kolster, K., et al., "Diagnostic value of the REM sleep behavior disorder screening questionnaire in Parkinson's disease," Sleep Medicine 16(1):186-189, Elsevier, Netherlands (Jan. 2015).

Haripriya, G.R., et al., "Incidence and Treatment Outcomes of Post Traumatic BPPV in Traumatic Brain Injury Patients," Indian J Otolaryngol Head Neck Surg 70(3):337-341, Springer, India (Apr. 2018).

Ananieva, E.A., et al., "Leucine Metabolism in T Cell Activation: mTOR Signaling and Beyond," Advances in Nutrition 7(4):798S-805S, American Society for Nutrition, United States (Jul. 2016).

Benard, P., et al., "Autoradiography in brain of Macaca fascicularis monkeys after injection of acetyl-DL-leucine [2-14C] (Tanganil)," Eur J Drug Metab Pharmacokinet 26(1-2):71-76, Springer Paris, France (Jan.-Jun. 2001).

Birnbaum, S.M., et al., "Specificity of amino acid acylases," J Biol Chem 194(1):455-470, Elsevier Inc., United States (Jan. 1952).

Bloch, K., and Rittenberg, D., "The metabolism of acetylamino acids," J Biol Chem 169(3):467-476, Elsevier Inc., United States (Aug. 1947).

Brandsch, M., et al., "The intestinal H+/peptide symporter PEPT1: structure-affinity relationships," Eur J Pharm Sci 21(1):53-60, Elsevier, Netherlands (Jan. 2004).

Broer, S., and Fairweather, S.J., "Amino Acid Transport Across the Mammalian Intestine," Compr Physiol 9(1):343-373, John Wiley and Sons Inc., United States (Jan. 1, 2019).

Camenisch, G., et al., "Review of theoretical passive drug absorption models: historical background, recent developments and limitations," Pharm Acta Helv 71(5):309-327, Elsevier, Netherlands (Nov. 1996).

Cheng, Y., and Prusoff, W.H., "Relationship between the inhibition constant (K1) and the concentration of inhibitor which causes 50 per cent inhibition (150) of an enzymatic reaction," Biochem Pharmacol 22(23):3099-3108, Elsevier Inc., United States (Dec. 1973).

Churchill, G.C., et al., "Unexpected differences in the pharmacokinetics of N-acetyl-DL-leucine enantiomers after oral dosing and their

(56) References Cited

OTHER PUBLICATIONS clinical relevance," PLoS One 15(2):e0229585, Public Library of Science, United States (Feb. 2020).

Del Amo, E.M., et al., "Pharmacokinetic role of L-type amino acid transporters LAT1 and LAT2," Eur J Pharm Sci 35(3):161-174, Elsevier, Netherlands (Oct. 2008).

Enerson, B.E., and Drewes, L.R., "Molecular features, regulation, and function of monocarboxylate transporters: implications for drug delivery," J Pharm Sci 92(8):1531-1544, John Wiley & Sons, United States (Aug. 2003).

Eriksson, T., et al., "Clinical pharmacology of thalidomide," Eur J Clin Pharmacol 57(5):365-376, Springer Verlag, Germany (Aug. 2001).

Fagan, T., "The Lactic Acid Shuttle- It May Change How We Image the Brian," Alzforum.org, Jul. 3, 2004, accessed at https://www.alzforum.org/news/research-news/lactic-acid-shuttle-it-may-change-how-we-image-brain, accessed on Jan. 30, 2024, 4 pages.

Fagerberg, L., et al., "Analysis of the human tissue-specific expression by genome-wide integration of transcriptomics and antibody-based proteomics," Mol Cell Proteomics 13(2):397-406, Elsevier BV, United States (Feb. 2014).

Feil, K., et al., "Effects of acetyl-DL-leucine on cerebellar ataxia (ALCAT trial): Study protocol for a multicenter, multinational, randomized, double-blind, placebo-controlled, crossover phase III trial," BMC Neurol 17(1):7, BioMed Central Ltd., United Kingdom (Jan. 2017).

Fields, T., et al., "A master protocol to investigate a novel therapy acetyl-L-leucine for three ultra-rare neurodegenerative diseases: Niemann-Pick type C, the GM2 gangliosidoses, and ataxia telangiectasia," Trials 22(1):84, BioMed Central, United Kingdom (Jan. 2021).

Gleeson, M.P., et al., "Probing the links between in vitro potency, ADMET and physicochemical parameters," Nat Rev Drug Discov 10(3):197-208, Nature Publishing Group, United Kingdom (Mar. 2011).

Gregori-Puigjane, E., et al., "Identifying mechanism-of-action targets for drugs and probes," Proc Natl Acad Sci USA 109(28):11178-11183, National Academy of Sciences, United States (Jul. 2012).

Halestrap, A.P., and Wilson, M.C., "The monocarboxylate transporter family—role and regulation," IUBMB Life 64(2):109-119, Wiley-Blackwell, United States (Feb. 2012).

Hashimoto, T., et al., "Lactate sensitive transcription factor network in L6 cells: activation of MCT1 and mitochondrial biogenesis," FASEB J 21(10):2602-2612, John Wiley & Sons, United States (Aug. 2007).

Im, H.A., et al., "N-acetyl-L-tyrosine as a tyrosine source during total parenteral nutrition in adult rats," Pediatr Res 19(6):514-518, Lippincott Williams and Wilkins Ltd., United States (Jun. 1985).

International Search Report and Written Opinion for International Application No. PCT/IB2022/055513, European Patent Office, Netherlands, mailed on Sep. 20, 2022, 14 pages.

International Transporter Consortium, et al., "Membrane transporters in drug development," Nat Rev Drug Discov 9(3):215-236, Nature Publishing Group, United Kingdom (Mar. 2010).

Izyumov, D.S., et al., "'Wages of fear': transient threefold decrease in intracellular ATP level imposes apoptosis," Biochim Biophys Acta 1658(1-2):141-147, Elsevier, Netherlands (Jul. 2004).

Jha, M.K., et al., "Metabolic Connection of Inflammatory Pain: Pivotal Role of a Pyruvate Dehydrogenase Kinase-Pyruvate Dehydrogenase-Lactic Acid Axis," J Neurosci 35(42):14353-14369, Society for Neuroscience, United States (Oct. 2015).

Kalogeropoulou, D., et al., "Leucine, when ingested with glucose, synergistically stimulates insulin secretion and lowers blood glucose," Metabolism 57(12):1747-1752, Elsevier, Netherlands (Dec. 2008).

Kanai, Y., et al., "Expression cloning and characterization of a transporter for large neutral amino acids activated by the heavy chain of 4F2 antigen (CD98)," J Biol Chem 273(37):23629-23632, Elsevier Inc., United States (Sep. 1998).

Kaya, E., et al., "Acetyl-leucine slows disease progression in lysosomal storage disorders," Brain Commun 3(1):fcaa148, Oxford University Press, United States (Dec. 2020).

Kaya, E., et al., "Beneficial Effects of Acetyl-DL-Leucine (ADLL) in a Mouse Model of Sandhoff Disease," J Clin Med 9(4):1050, MDPI AG, Switzerland (Apr. 2020).

Kennedy, B.E., et al., "Adaptations of energy metabolism associated with increased levels of mitochondrial cholesterol in Niemann-Pick type C1-deficient cells," J Biol Chem 289(23):16278-16289, Elsevier Inc., United States (Jun. 2014).

Keogh, J.P., "Membrane transporters in drug development," Adv Pharmacol 63:1-42, Academic Press Inc., United States (2012).

Koepsell, H. and Endou, H., "The SLC22 drug transporter family," Pflugers Arch 447(5):666-676, Springer Verlag, Germany (Feb. 2004).

Krehbiel, C.R., and Matthews, J.C., "Absorption of Amino Acids and Peptides" in Amino Acids in Animal Nutrition, D'Mello, J.P.F., ed., pp. 41-70, CABI Publishing, United Kingdom (2003).

Leeson, P.D., and Springthorpe, B., "The influence of drug-like concepts on decision-making in medicinal chemistry," Nat Rev Drug Discov 6(11):881-890, Nature Publishing Group, United Kingdom (Nov. 2007).

Lin, L., et al., "SLC transporters as therapeutic targets: emerging opportunities," Nat Rev Drug Discov 14(8):543-560, Nature Publishing Group, United Kingdom (Aug. 2015).

Lipinski, C.A., "Drug-like properties and the causes of poor solubility and poor permeability," J Pharmacol Toxicol Methods 44(1):235-249, Elsevier Inc., United States (Jul.-Aug. 2000).

Missner, A., and Pohl, P., "110 years of the Meyer-Overton rule: predicting membrane permeability of gases and other small compounds," Chemphyschem 10(9-10):1405-1414, Wiley-VCH Verlag, Germany (Jul. 2009).

Neuhauser, M., et al., "Utilization of N-acetyl-L-tyrosine and glycyl-L-tyrosine during long-term parenteral nutrition in the growing rat," Am J Clin Nutr 42(4):585-596, American Society for Nutrition, United States (Oct. 1985).

Neuhoff, S., et al., "pH-Dependent passive and active transport of acidic drugs across Caco-2 cell monolayers," Eur J Pharm Sci 25(2-3):211-220, Elsevier, Netherlands (Jun. 2005).

Newington, J.T., et al., "Reevaluating Metabolism in Alzheimer's Disease from the Perspective of the Astrocyte-Neuron Lactate Shuttle Model," J Neurodegener Dis 2013:234572, S. Karger AG, Switzerland (2013).

Nicklin, P., et al., "Bidirectional transport of amino acids regulates mTOR and autophagy," Cell 136(3):521-534, Cell Press, United States (Feb. 2009).

Nigam, S.K., et al., "The organic anion transporter (OAT) family: a systems biology perspective," Physiol Rev 95(1):83-123, American Psychological Society, United States (Jan. 2015).

Olah, J., et al., "Increased glucose metabolism and ATP level in brain tissue of Huntington's disease transgenic mice," FEBS J 275(19):4740-4755, Wiley-Blackwell Publishing Ltd., United States (Oct. 2008).

Patet, C., et al., "Cerebral Lactate Metabolism After Traumatic Brain Injury," Curr Neurol Neurosci Rep 16(4):31, Current Medicine Group, United States (Apr. 2016).

Pochini, L., et al., "Membrane transporters for the special amino acid glutamine: structure/function relationships and relevance to human health," Front Chem 2:61, Frontiers Media S.A., Switerland (Aug. 2014).

PubChem, "Cyclopentyl (2S)-2-(hexanoylamino)-4-methylpentatnoate," PubChem CID 143660433, accessed at https://pubchem.ncbi.nlm.nih.gov/compound/143660433, accessed on Jan. 30, 2024, 8 pages.

Puri, S., and Juvale, K., "Monocarboxylate transporter 1 and 4 inhibitors as potential therapeutics for treating solid tumours: A review with structure-activity relationship insights," Eur J Med Chem 199:112393, Elsevier Masson, France (Aug. 2020).

Rubio-Aliaga, I., and Daniel, H., "Peptide transporters and their roles in physiological processes and drug disposition," Xenobiotica 38(7-8):1022-1042, Informa Healthcare, United Kingdom (Jul. 2008).

(56) References Cited

OTHER PUBLICATIONS

Sala, N., et al., "Cerebral extracellular lactate increase is predominantly nonischemic in patients with severe traumatic brain injury," J Cereb Blood Flow Metab 33(11):1815-1822, SAGE Publications, United States (Nov. 2013).

Sawada, K., et al., "Recognition of L-amino acid ester compounds by rat peptide transporters PEPT1 and PEPT2," J Pharmacol Exp Ther 291(2):705-709, American Society for Pharmacology and Experimental Therapeutics, United States (Nov. 1999).

Scalise, M., et al., "The Human SLC7A5 (LAT1): The Intriguing Histidine/Large Neutral Amino Acid Transporter and Its Relevance to Human Health," Front Chem 6:243, Frontiers Media S.A., Switzerland (Jun. 2018).

Schoser, B., et al., "Treatment of restless legs syndrome with acetyl-DL-leucine—accidental findings and a small case series," Neurology 26(694):EPO2251, Lippincott Williams and Wilkins Ltd., United States (Mar. 2021).

Sheffner, A.L., et al., "Metabolic studies with acetylcysteine," Biochem Pharmacol 15(10):1523-1535, Elsevier Inc., United States (Oct. 1966).

Smith, Q.R., et al., "Kinetics of neutral amino acid transport across the blood-brain barrier," J Neurochem 49(5): 1651-1658, Wiley-Blackwell Publishing Ltd., United Kingdom (Nov. 1987).

Soares-Da-Silva, P., and Serrao, M.P., "High- and low-affinity transport of L-leucine and L-DOPA by the hetero amino acid exchangers LAT1 and LAT2 in LLC-PK1 renal cells," Am J Physiol Renal Physiol 287(2):F252-F261, American Physiological Society, United States (Aug. 2004).

Strupp, M., et al., "Prophylactic treatment of migraine with and without aura with acetyl-DL-leucine: a case series," J Neurol 266(2):525-529, Springer Science + Business Media, Germany (Feb. 2019).

Sugano, K., et al., "Coexistence of passive and carrier-mediated processes in drug transport," Nat Rev Drug Discov 9(8):597-614, Nature Publishing Group, United Kingdom (Aug. 2010).

Sun, S., et al., "Lactic Acid: No. Longer an Inert and End-Product of Glycolysis," Physiology (Bethesda) 32(6):453-463, American Physiological Society, United States (Nov. 2017).

Thompson, B.R., et al., "Pharmacokinetics of gemcitabine and its amino acid ester prodrug following intravenous and oral administrations in mice," Biochem Pharmacol 180:114127, Elsevier Inc., United States (Oct. 2020).

Van De Waterbeemd, H., et al., "Estimation of blood-brain barrier crossing of drugs using molecular size and shape, and H-bonding descriptors," J Drug Target 6(2):151-165, Informa Healthcare, United Kingdom (1998).

Vruchte, E., et al., "Effects of N-Acetyl-Leucine and its enantiomers in Niemann-Pick disease type C cells," BioRxiv.org, accessed at https://www.biorxiv.org/content/10.1101/82622v1, accessed on Jan. 30, 2024, 13 pages.

Walter, A., and Gutknecht, J., "Monocarboxylic acid permeation through lipid bilayer membranes," J Membr Biol 77(3):255-264, Springer New York, United States (1984).

Wang, G., et al., "Intestinal OCTN2- and MCT1-targeted drug delivery to improve oral bioavailability," Asian J Pharm Sci 15(2):158-173, Shenyang Pharmaceutical University, China (Mar. 2020).

Waring, M.J., "Defining optimum lipophilicity and molecular weight ranges for drug candidates-Molecular weight dependent lower logD limits based on permeability," Bioorg Med Chem Lett 19(10):2844-2851, Elsevier Ltd., United Kingdom (May 2009).

Patterson, M.C., et al., "Oral Miglustat in Niemann-Pick type C (NPC) Disease: 1-year Interim Analysis," 11th International Congress of Human Genetics—Brisbane, Australia (Aug. 6-10, 2006) Final Program and Abstract Book, Abstract 1513, p. 267, Human Genetics Society of Australasia, Australia (Aug. 2006).

Strupp, M., et al., "Episodic ataxia type 2," Neurotherapeutics 4(2):267-273, Elsevier, United States (Apr. 2007).

Las Heras, M., et al., "Understanding the phenotypic variability in Niemann-Pick disease type C (NPC): a need for precision medicine," NPJ Genome Medicine 8(1):21, Nature Publishing Group, United Kingdom (Aug. 2023).

Bremova-Ertl, T., et al., "Trial of N-Acetyl-l-Leucine in Niemann-Pick Disease Type C," New England Journal of Medicine 390(5):421-431, Massachusetts Medical Society, United States (Feb. 2024).

Fields, T., et al., "N-acetyl-L-leucine for Niemann-Pick type C: a multinational double-blind randomized placebo-controlled cross-over study," Trials 24(1):361, BioMed Central, United Kingdom (May 2023).

Mengel, E., et al., "Clinical disease progression and biomarkers in Niemann-Pick disease type C: a prospective cohort study," Orphanet Journal of Rare Diseases 15(1):328, BioMed Central, United Kingdom (Nov. 2020).

Schmitz-Hubsch, T., "Scale for the assessment and rating of ataxia: development of a new clinical scale," Neurology 66(11):1717-1720, Lippincott Williams & Wilkins, United States (Jun. 2006).

U.S. Food and Drug Administration, Aqneursa™ (levacetylleucine) for oral suspension Approval Label and Prescribing Information, IntraBio Ltd., revised Sep. 2024, 15 pages.

U.S. Food and Drug Administration, MIPLYFFA (arimoclomol) capsules, for oral use, Approval Label and Prescribing Information, Zevra Therapeutics, Inc., revised Oct. 2025, accessed at https://zevra.com/documents/MIPLYFFA-Prescribing-Information.pdf, accessed on Jan. 29, 2025, 16 pages.

Li, B., et al., "Identification and functional characterization of de novo variant in the SYNGAP1 gene causing intellectual disability," Frontiers in Genetics 14:1270175, pp. 1-7, Frontiers Research Foundation, Switzerland (Oct. 2023).

International Search Report and Written Opinion for International Application No. PCT/US2025/015918, Commissioner for Patents, United States, mailed on Apr. 2, 2025, 16 pages.

Sodhi, D.K., and Hagerman, R., "Fragile X Premutation: Medications, Therapy and Lifestyle Advice," Pharmacogenomics and Personalized Medicine 14:1689-1699, Dove Medical Press, New Zealand (Dec. 2021).

International Search Report and Written Opinion for International Application No. PCT/US2025/034430, European Patent Office, Netherlands, mailed on Jan. 30, 2026, 33 pages.

Palacios, N., et al., "Circulating plasma metabolites and cognitive function in a Puerto Rican cohort," Journal of Alzheimer's Disease 76(4):1267-1280, IOS Press, Netherlands (May 2020).

Colaco, A., et al., "Mechanistic convergence and shared therapeutics agents in Niemann-Pick disease," Journal of Inherited Metabolic Disease 43(3):574-585, Wiley, United States (Jan. 2020).

Sindelar, M., et al., "Untargeted metabolite profiling of cerebrospinal fluid uncovers biomarkers for severity of late infantile neuronal ceroid lipofuscinosis (CLN2, Batten disease)," Scientific Reports 8:15229, pp. 1-12, Nature Publishing Group, United Kingdom (Oct. 2018).

Amador, M., et al., "Targeted versus untargeted omics—the CAFSA story," Journal of Inherited Metabolic Disease 41(3):447-456, Wiley, United States (Feb. 2018).

Kalla, R., et al., "Update on the pharmacotherapy of cerebellar and central vestibular disorders," Journal of Neurology 263:S24-S29, Springer Science+Business Media, United States (Apr. 2016).

Williams, G., "A searchable cross-platform gene expression database reveals connections between drug treatments and disease," BMC Genomics 13:12, pp. 1-14, BioMed Central, United Kingdom (Jan. 2012).

Huhtiniemi, T., et al., "Structure-based design of pseudopeptidic inhibitors for SIRT1 and SIRT2," Journal of Medicinal Chemistry 54(19):6456-6468, American Chemical Society, United States (Oct. 2011).

Saberi-Karimian, M., et al., "The Effect of N-Acetyl-DL-Leucine on Neurological Symptoms in a Patient with Ataxia-Telangiectasia: a Case Study," Cerebellum 22(1):96-101, Springer, United States (Feb. 2023).

Pedroso, J.L., et al., "Acute cerebellar ataxia: differential diagnosis and clinical approach," Arquivos de Neuro-Psiquiatria 77(3):184-193, Brazilian Academy of Neurology, Brazil (Mar. 2019).

(56)           References Cited

OTHER PUBLICATIONS

Tomimitsu H., and Mizusawa H., "[Episodic ataxia type 2]," Clinical Calcium 11(11): 1456-1459, Abstract only, Iyaku (Medicine & Drug) Journal Co., Ltd, Japan (Nov. 2001).

* cited by examiner

| Median survival | Npc1-/- UT | Npc1-/- ADLL | Npc1-/- ADLL | Npc1-/- ALL | Npc1-/- ADL |
|---|---|---|---|---|---|
| | 87 | 91 (+4.5%) | | 95 (+9.1%) | 87.5 |

COMBINATION THERAPY WITH ACETYL-LEUCINE AND MIGLUSTAT

BACKGROUND OF THE INVENTION

Field of the Invention

The present disclosure provides a combination of acetyl-leucine and miglustat for treating lysosomal storage disorders (LSDs) in a subject, wherein the subject is naive to treatment with miglustat.

Background

Lysosomal storage disorders (LSDs) are a group of inherited metabolic diseases caused by defects in lysosomal homeostasis. LSDs encompass over 70 diseases, with a collective clinical frequency of 1:5000 live births. These diseases can be classified into two main groups: primary storage disorders resulting from a direct deficiency in degradation pathways (typically lysosomal enzyme deficiency disorders), and secondary storage disorders which are caused by malfunctioning downstream lysosomal proteins or processes that impact the lysosome (e.g., defects in trafficking pathways).

The pathology of LSDs affects many of the body's systems, but most commonly the nervous system. Progressive neurodegeneration resulting in physical disability and mental deterioration are common symptoms. Such disorders are generally severely progressive and unremitting. They tend to present in the first few years of life and the severe progression results in frequent hospitalization. If left untreated, patients often die in their mid-teens. Adult-onset patients have also been described.

Current therapeutic approaches to treat LSDs are limited. Miglustat is regarded as the first-line therapy for treating Niemann-Pick type C disease (NPC), Patterson et al., *Lancet Neurol* 6:765-772 (2007), but this drug causes unwanted weight loss and gastrointestinal disturbances in the treatment subjects. Champion et al., *J Inherit Metab Dis* 33 Suppl 3:S379-83 (2010). Acetyl-DL-leucine can also be used to treat NPC as a single agent, and has been administered as an add-on therapy in NPC subjects receiving miglustat as a first-line therapy. Bremova et al., *Neurology* 85:1368-1375 (2015); Cortina-Borj a et al., *Orphanet Journal of Rare Diseases* 13:143 (2018); WO 2018/029657. These add-on studies did not include NPC subjects naive to treatment with miglustat and were not designed to measure the combined therapeutic effects of acetyl-DL-leucine and miglustat. There is a need for improved treatments of LSDs with enhanced efficacy and an improved safety profile for first-line therapy.

BRIEF SUMMARY OF THE INVENTION

Applicant has unexpectedly discovered that acetyl-leucine synergizes with miglustat to treat NPC, e.g., slow disease progression. Also, without wishing to be bound by any particular theory, it is believed that the combination of acetyl-leucine and miglustat will lessen the toxicity, e.g., weight loss and/or appetite suppression, typically associated with the administration of miglustat.

In one aspect, the present disclosure provides acetyl-leucine in combination with miglustat for use in the treatment of a LSD in a subject, wherein the subject is naive to treatment with miglustat.

In another aspect, the present disclosure provides a method of treating a LSD in a subject in need thereof, the method comprising administering a combination of (i) a therapeutically effective amount of acetyl-leucine; and (ii) a therapeutically effective amount of miglustat, to the subject, wherein the subject is naive to treatment with miglustat.

In another aspect, the present disclosure provides the combination of acetyl-leucine and miglustat for first-first line therapy to treat a LSD.

In another aspect, the present disclosure provides a kit comprising acetyl-leucine and miglustat for treating a lysosomal storage disease in a subject.

It is to be understood that both the foregoing summary and the following detailed description are exemplary and explanatory only, and are not restrictive of the invention as claimed.

DETAILED DESCRIPTION OF DRAWINGS

Figure 9:
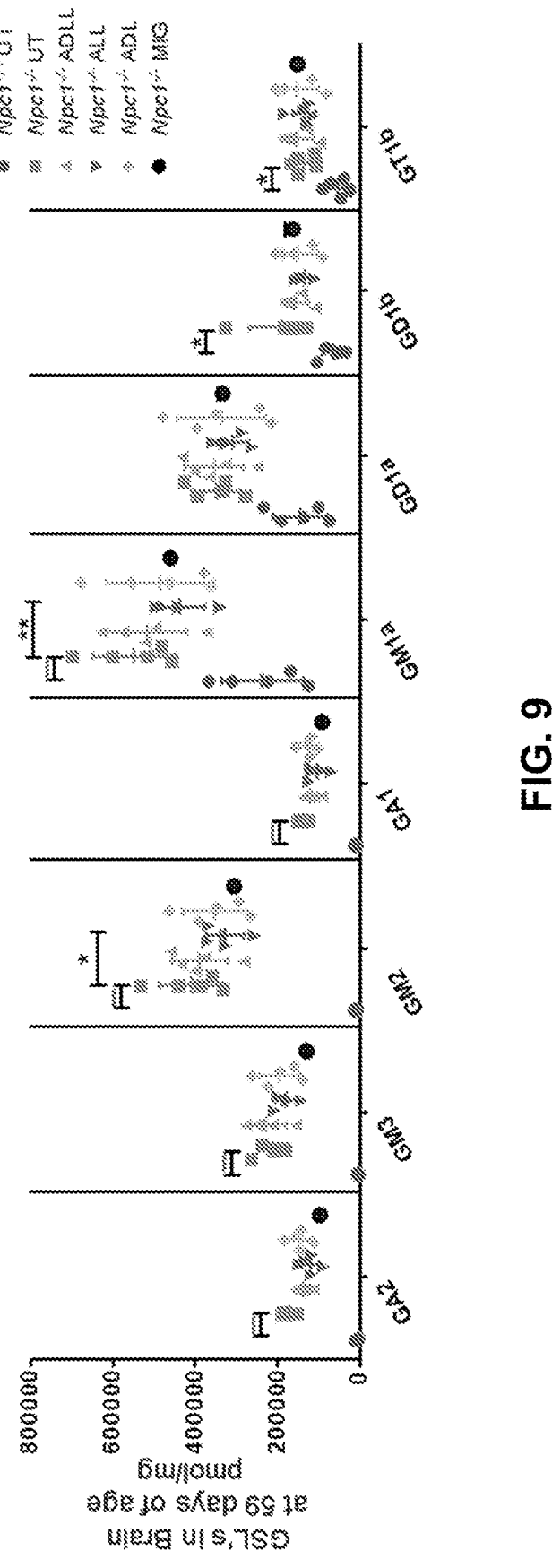

FIG. 9 is a column scatter graph showing the glycosphingolipid (GSL) profiles in brain (mean±SD, *p<0.024, p<0.0019, *p<0.0005, ****p<0.0001 (2-way ANOVA)) for untreated wild type (Npc1$^{+/+}$ UT) and NPC1 (Npc1$^{-/-}$ UT) mice, and ADLL (Npc1$^{-/-}$ ADLL), ALL (Npc1$^{-/-}$ ALL), ADL (Npc1$^{-/-}$ ADL), and miglustat (Npc1$^{-/-}$ MIG) treated NPC1 mice at 59 days of age. For all AL treatments n=5 animals per group, and for miglustat (positive control) n=2 or n=1.

Figures 10A, 10B:
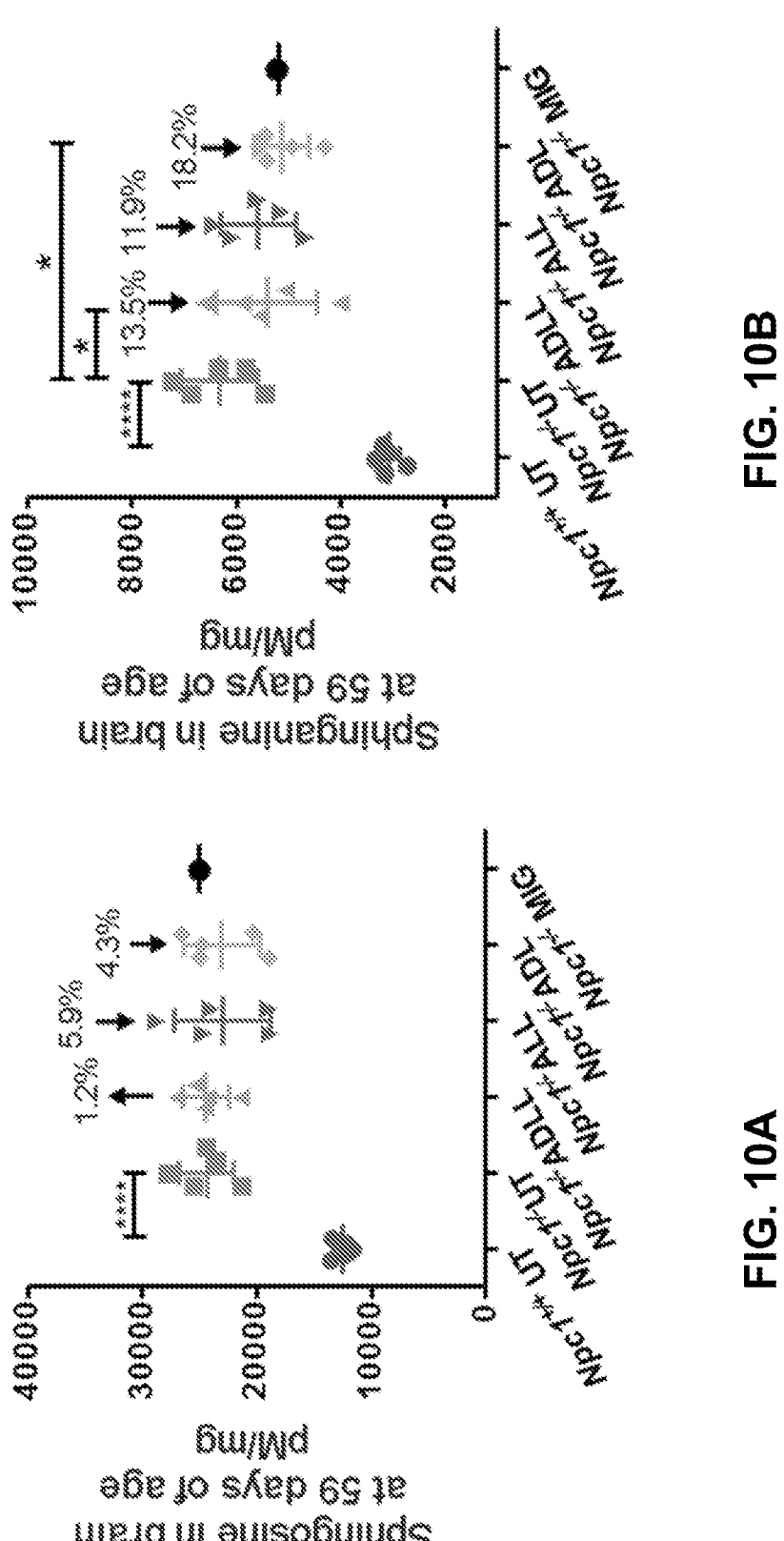

FIG. 10A is a column scatter graph showing the sphingosine levels in brain (mean±SD, ****p<0.0001 (One-way ANOVA)) for untreated wild type (Npc1$^{+/+}$ UT) and NPC1 (Npc1$^{-/-}$ UT) mice, and ADLL (Npc1$^{-/-}$ ADLL), ALL (Npc1$^{-/-}$ ALL), ADL (Npc1$^{-/-}$ ADL), and miglustat (Npc1$^{-/-}$ MIG) treated NPC1 mice at 59 days of age. For all AL treatments n=5 animals per group, and for miglustat (positive control) n=2 or n=1.

FIG. 10B is a column scatter graph showing the sphinganine levels in brain (mean±SD, *p<0.046, ****p<0.0001 (One-way ANOVA)) for untreated wild type (Npc1$^{+/+}$ UT) and NPC1 (Npc1$^{-/-}$ UT) mice, and ADLL (Npc1$^{-/-}$ ADLL), ALL (Npc1$^{-/-}$ ALL), ADL (Npc1$^{-/-}$ ADL), and miglustat (Npc MIG) treated NPC1 mice at 59 days of age. For all AL treatments n=5 animals per group, and for miglustat (positive control) n=2 or n=1.

Figure 11:
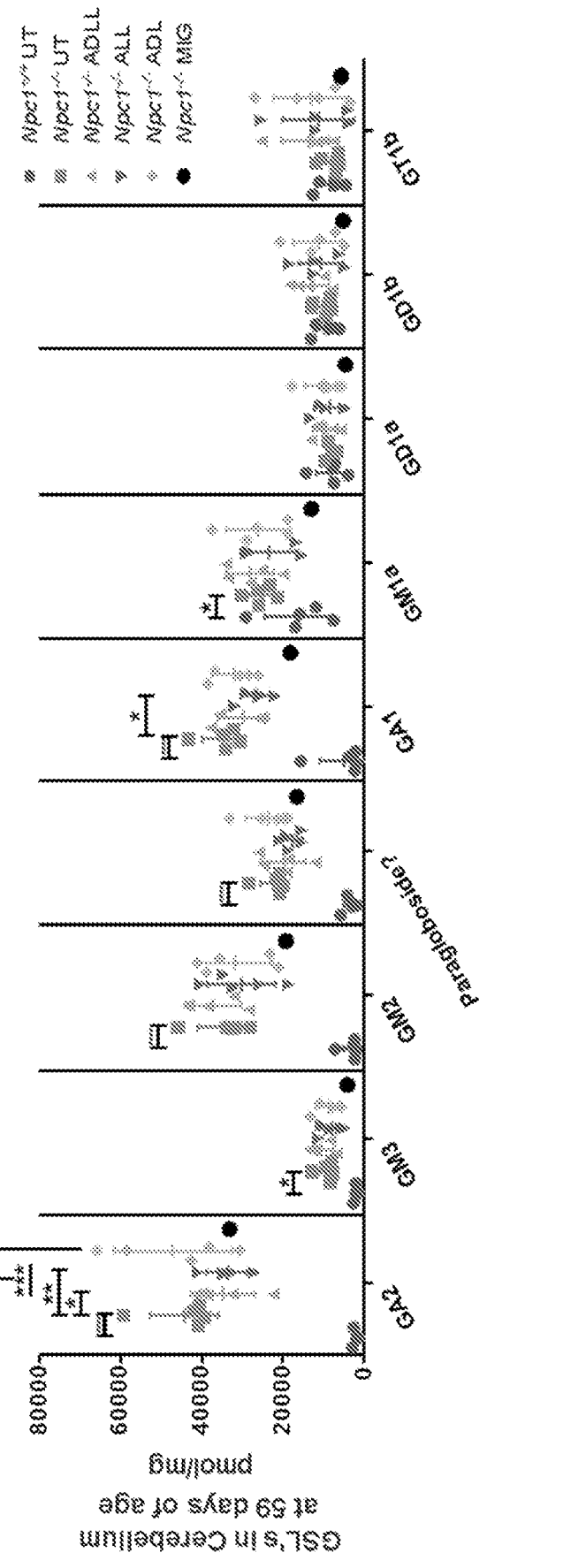

FIG. 11 is a column scatter graph showing the GSL profiles in the cerebellum (mean±SD, *p<0.026, p<0.005, *p<0.0009, ****p<0.0001 (2-way ANOVA)) for untreated wild type (Npc1$^{+/+}$ UT) and NPC1 (Npc1$^{-/-}$ UT) mice, and ADLL (Npc1$^{-/-}$ ADLL), ALL (Npc1$^{-/-}$ ALL), ADL (Npc1$^{-/-}$ ADL), and miglustat (Npc1$^{-/-}$ MIG) treated NPC1 mice at 59 days of age. For all AL treatments n=5 animals per group, and for miglustat (positive control) n=2 or n=1.

Figure 12B:
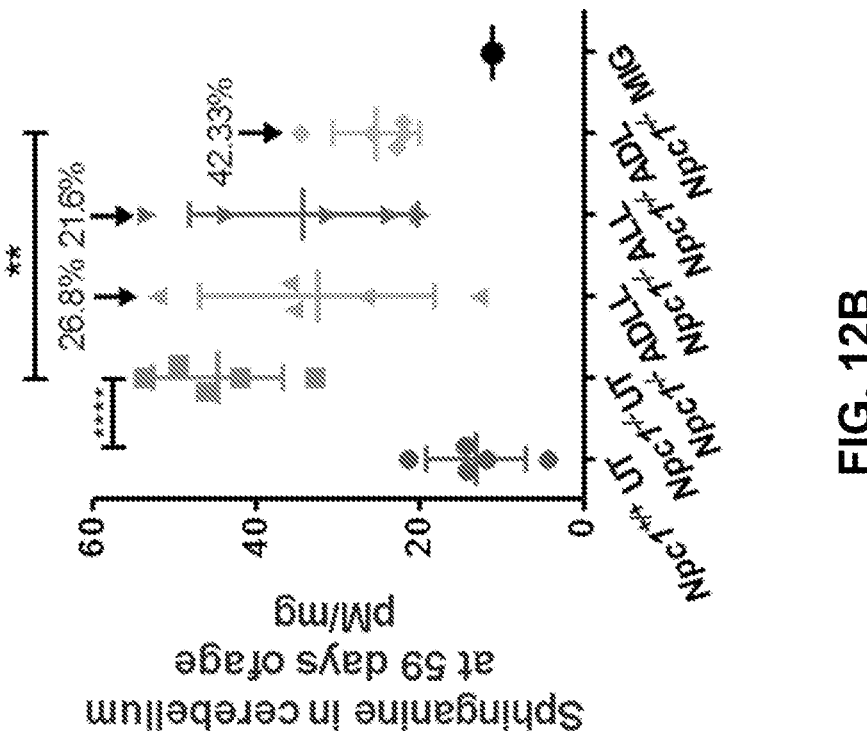
Figure 12A:
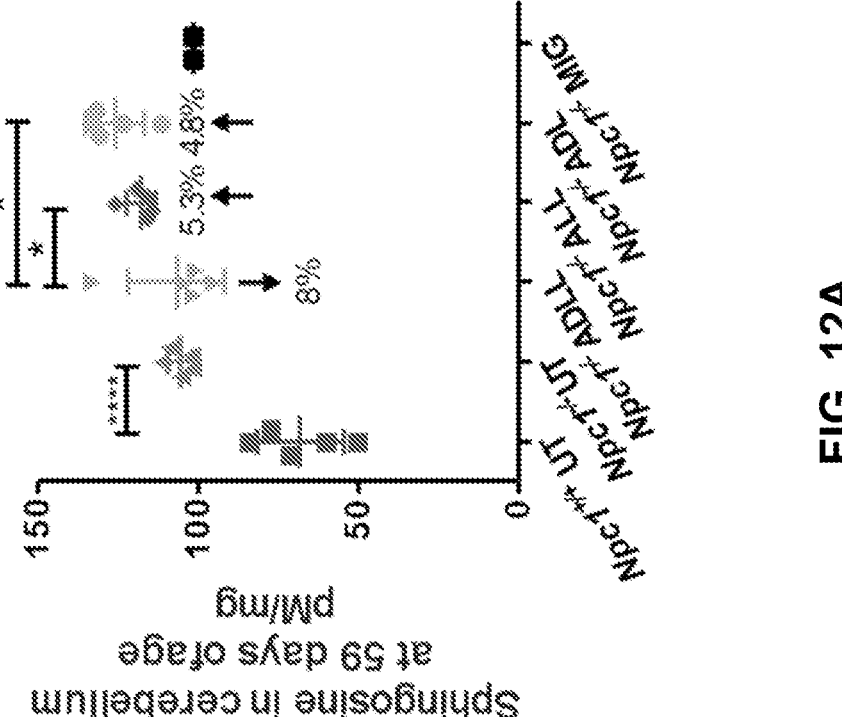

FIG. 12A is a column scatter graph showing the sphingosine levels in the cerebellum (mean±SD, *p<0.046 ****p<0.0001 (One-way ANOVA)) for untreated wild type (Npc1$^{+/+}$ UT) and NPC1 (Npc1$^{-/-}$ UT) mice, and ADLL (Npc1$^{-/-}$ ADLL), ALL (Npc1$^{-/-}$ ALL), ADL (Npc1$^{-/-}$ ADL), and miglustat (Npc1$^{-/-}$ MIG) treated NPC1 mice at 59 days of age. For all AL treatments n=5 animals per group, and for miglustat (positive control) n=2 or n=1.

FIG. 12B is a column scatter graph showing the sphinganine levels in brain without the cerebellum (mean±SD, p<0.075, **p<0.0001 (One-way ANOVA)) for untreated wild type (Npc1$^{+/+}$ UT) and NPC1 (Npc1$^{-/-}$ UT) mice, and ADLL (Npc1$^{-/-}$ ADLL), ALL (Npc1$^{-/-}$ ALL), ADL (Npc1$^{-/-}$ ADL), and miglustat (Npc1$^{-/-}$ MIG) treated NPC1 mice at 59 days of age. For all AL treatments n=5 animals per group, and for miglustat (positive control) n=2 or n=1.

Figure 13:
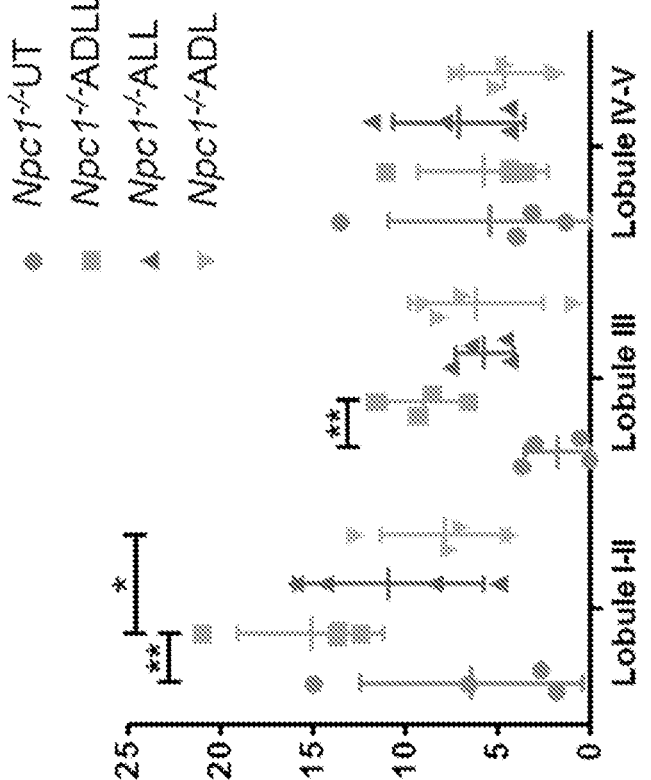

FIG. 13 is a column scatter graph showing the purkinje cell density (mean±SD, *p<0.011, **p<0.028 (One-way ANOVA)) for NPC1 untreated (Npc1$^{-/-}$ UT), and ADLL (Npc1$^{-/-}$ ADLL), ALL (Npc1$^{-/-}$ ALL), and ADL (Npc1$^{-/-}$ ADL) treated mice at 59 days of age. For all AL treatments n=5 animals per group.

Figure 14:
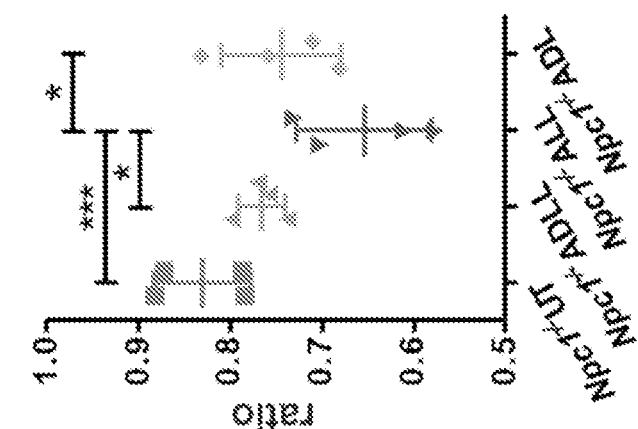

FIG. 14 is a column scatter graph showing the CD68 cell density (mean±SD, *p <0.046, ***p<0.0009 (One-way ANOVA)) for NPC1 untreated (Npc1$^{-/-}$ UT), and ADLL (Npc1$^{-/-}$ ADLL), ALL (Npc1$^{-/-}$ ALL), and ADL (Npc1$^{-/-}$ ADL) treated mice at 59 days of age. For all AL treatments n=5 animals per group.

Figures 15A, 15B:
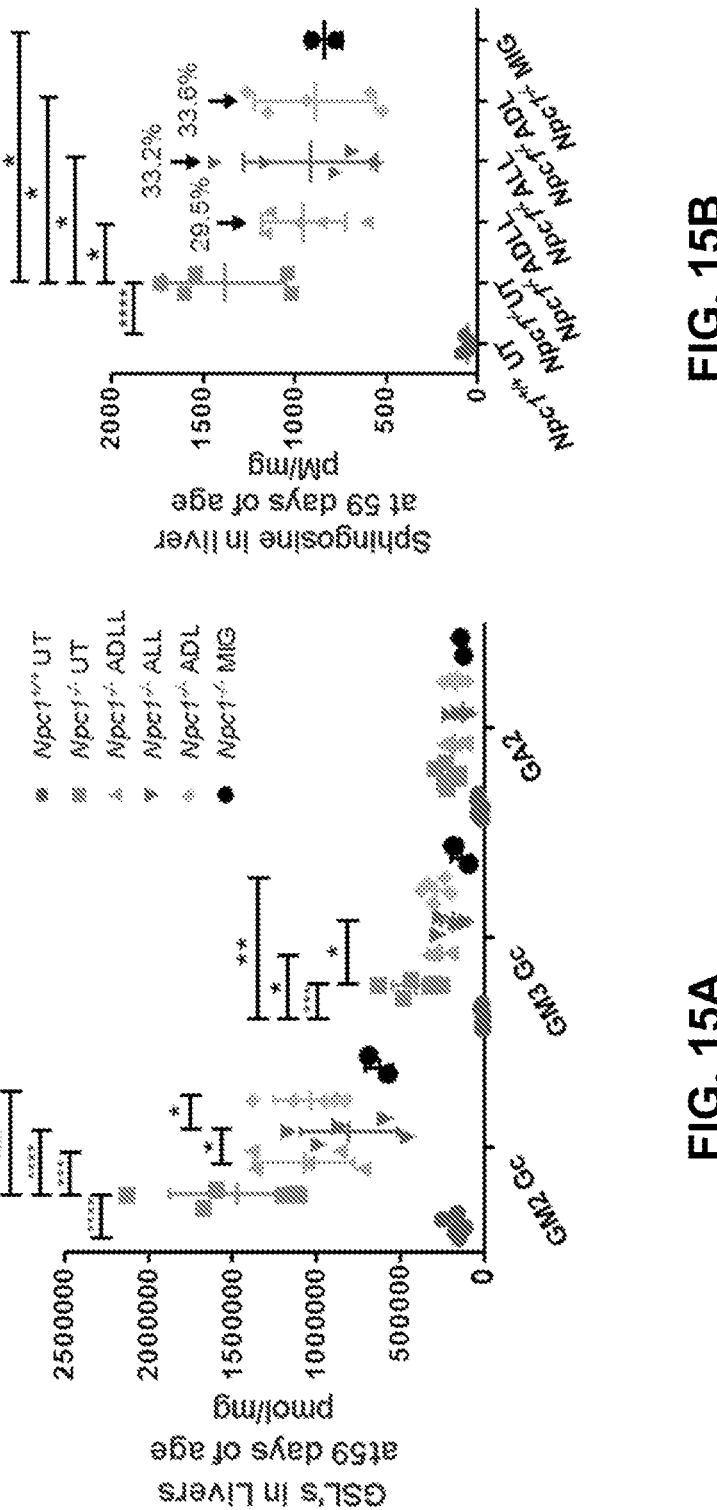

FIG. 15A is a column scatter graph showing the GSL profile in liver (mean±SD *p<0.038, *p<0.0002, **p<0.0001 (2-way ANOVA)) for untreated wild type (Npc1$^{+/+}$ UT) and NPC1 (Npc1$^{-/-}$ UT) mice, and ADLL (Npc1$^{-/-}$ ADLL), ALL (Npc1$^{-/-}$ ALL), ADL (Npc1$^{-/-}$ ADL), and miglustat (Npc1$^{-/-}$ MIG) treated NPC1 mice at 59 days of age. For all AL treatments n=5 animals per group, and for miglustat (positive control) n=2 or n=1.

FIG. 15B is a column scatter graph showing the sphingosine levels in liver (mean±SD. *p<0.0393, ****p<0.0001 (One-way ANOVA)) for untreated wild type (Npc1$^{+/+}$ UT) and NPC1 (Npc1$^{-/-}$ UT) mice, and ADLL (Npc1$^{-/-}$ ADLL), ALL (Npc1$^{-/-}$ ALL), ADL (Npc1$^{-/-}$ ADL), and miglustat (Npc1$^{-/-}$ MIG) treated NPC1 mice at 59 days of age. For all AL treatments n=5 animals per group, and for miglustat (positive control) n=2 or n=1.

Figure 15D:
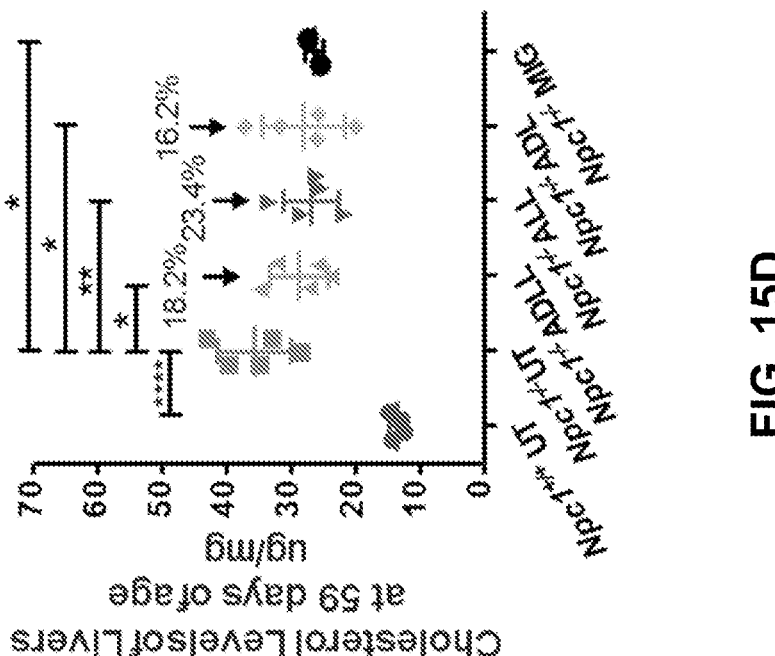
Figure 15C:
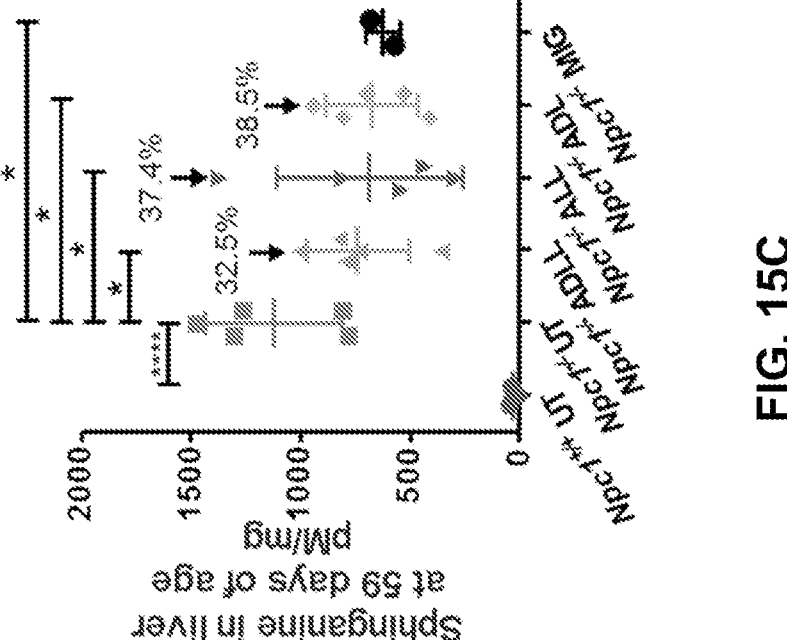

FIG. 15C is a column scatter graph showing the sphinganine levels in liver (mean±SD, *p<0.04, ****p<0.0001 (One-way ANOVA)) for untreated wild type (Npc1$^{+/+}$ UT) and NPC1 (Npc1$^{-/-}$ UT) mice, and ADLL (Npc1$^{-/-}$ ADLL), ALL (Npc1$^{-/-}$ ALL), ADL (Npc1$^{-/-}$ ADL), and miglustat (Npc MIG) treated NPC1 mice at 59 days of age. For all AL treatments n=5 animals per group, and for miglustat (positive control) n=2 or n=1.

FIG. 15D is a column scatter graph showing the liver cholesterol (mean±SD, *p <0.034, p=0.0091, **p<0.0001 (One-way ANOVA)) for untreated wild type (Npc1$^{+/+}$ UT) and NPC1 (Npc1$^{-/-}$ UT) mice, and ADLL (Npc1$^{-/-}$ ADLL), ALL (Npc1$^{-/-}$ ALL), ADL (Npc1$^{-/-}$ ADL), and miglustat (Npc1$^{-/-}$ MIG) treated NPC1 mice at 59 days of age. For all AL treatments n=5 animals per group, and for miglustat (positive control) n=2 or n=1.

Figures 16, 17:
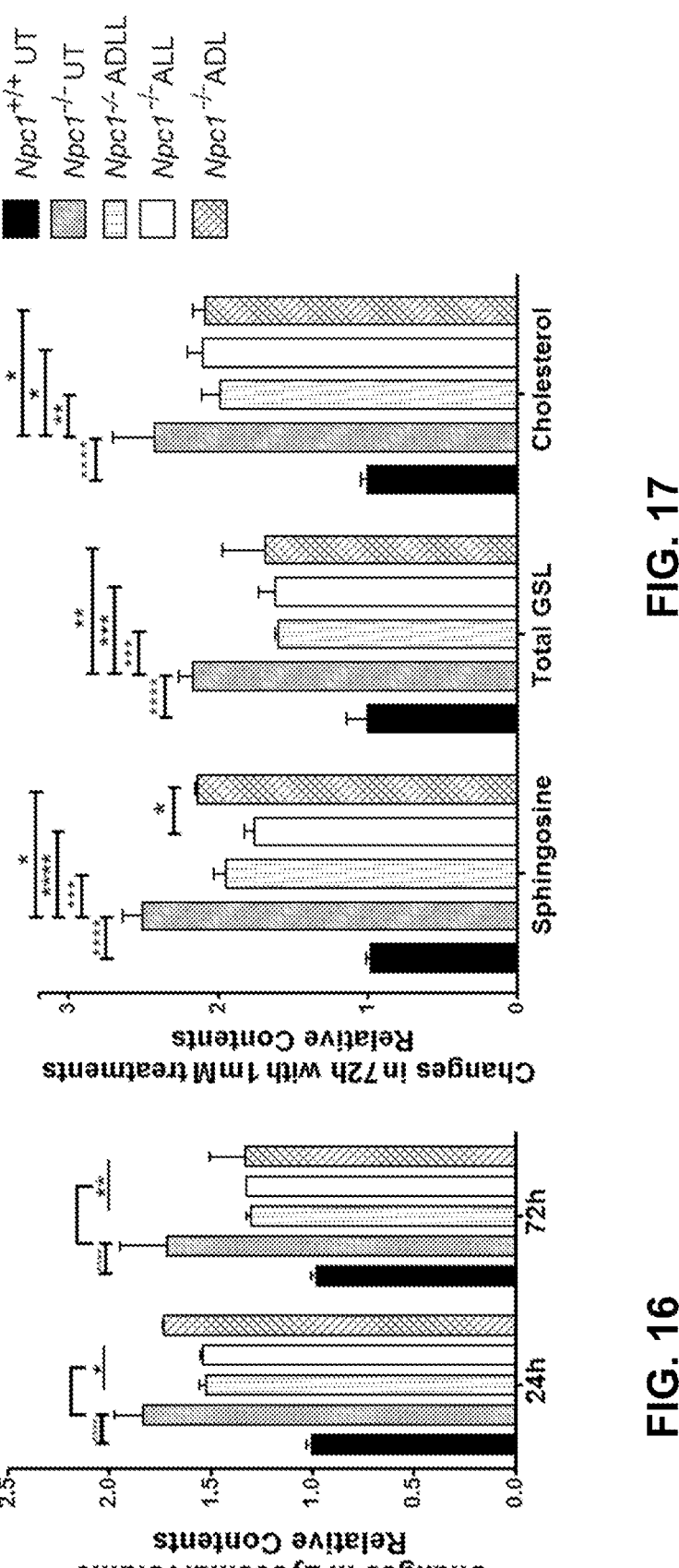

FIG. 16 is a bar graph showing the Lysotracker Green relative to Npc1$^{+/+}$ with 24 and 72 h 1 mM AL treatment (mean±SD, *p<0.018, p<0.005, **p<0.0001 (2-way ANOVA)) in mice at 59 days of age. For all AL treatments n=5 animals per group.

FIG. 17 is a bar graph showing the sphingosine, total GSL and free cholesterol levels (72 h) relative to Npc1$^{+/+}$ with 72 h 1 mM AL treatment (mean±SD, *p<0.027, p<0.0044, *p<0.001 ****p<0.0001 (2-way ANOVA)) in mice at 59 days of age. For all AL treatments n=5 animals per group.

Figure 18:
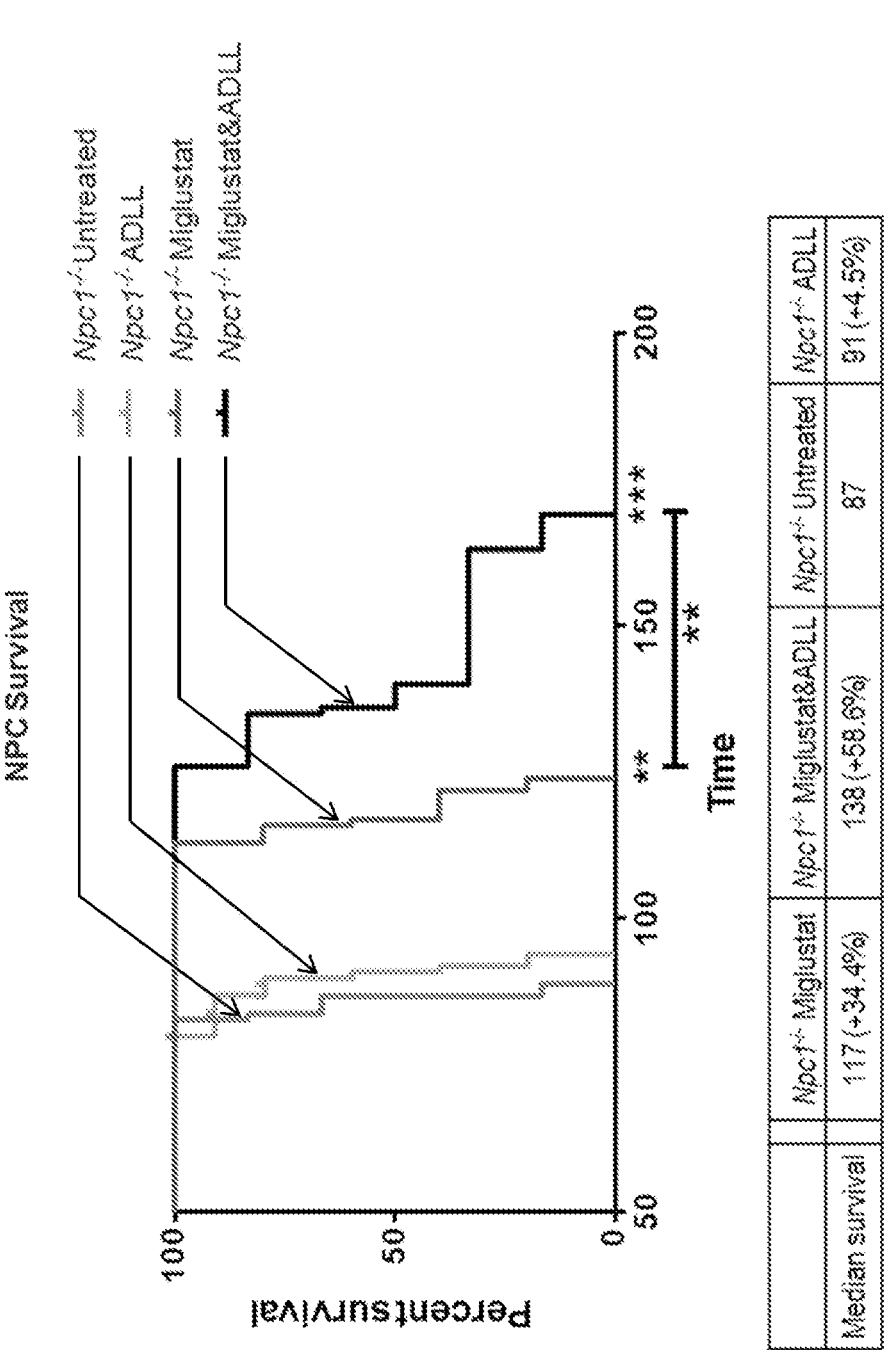

FIG. 18 is a line graph showing the survival curves (mean±SD, *p=0.0270, p <0.0035, *p=0.0007 (Gehan-Breslow-Wilcoxon test)) and an analysis table for NPC1 untreated (Npc1$^{-/-}$ UT), ADLL (Npc1$^{-/-}$ ADLL), miglustat (Npc1$^{-/-}$ MIG), and combination (Npc1$^{-/-}$ miglustat & ADLL) treated mice with a minimum of 5 animals for each group.

Figure 19:
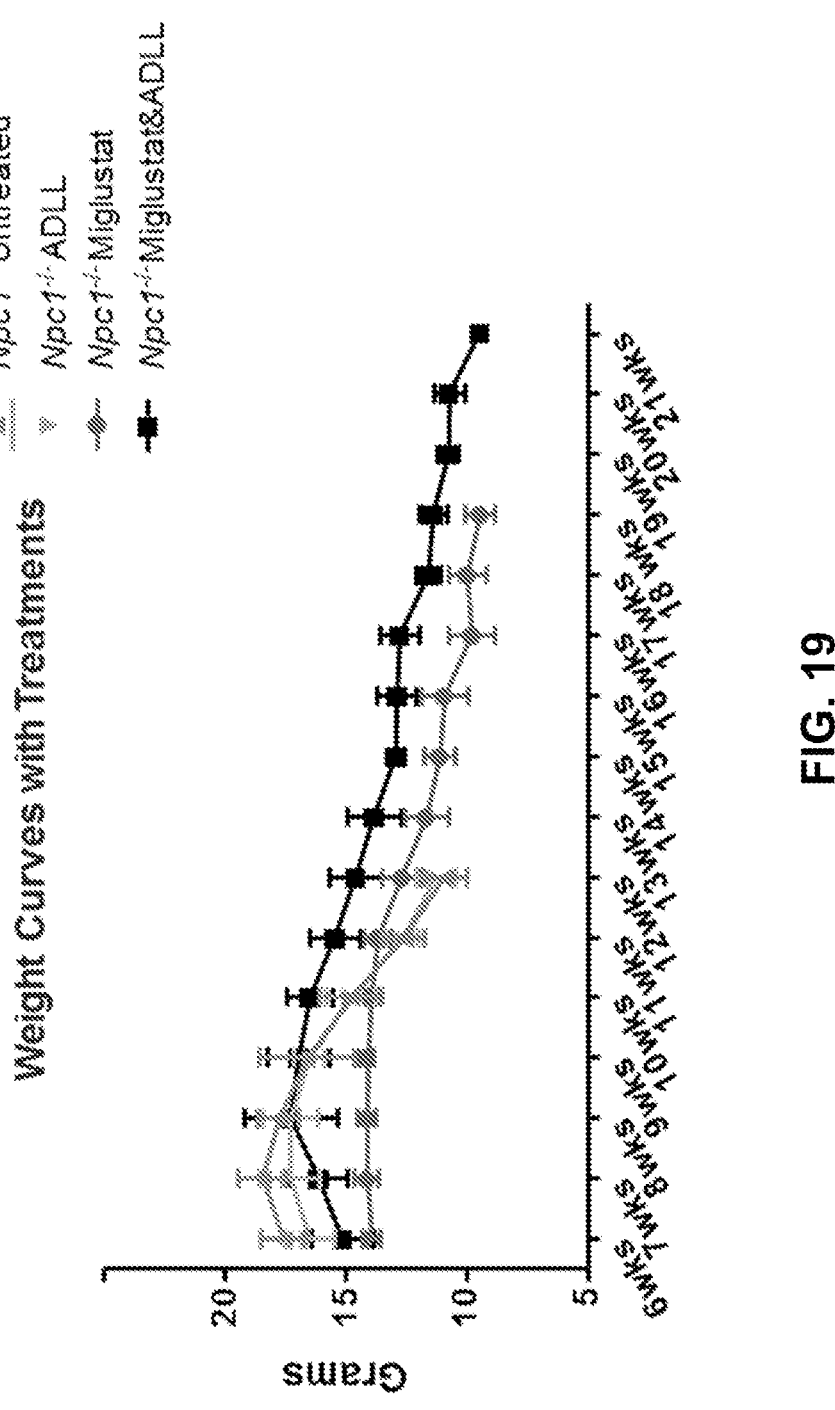

FIG. 19 is a line graph showing the body weight curves over time (mean±SD) for NPC1 untreated (Npc1$^{-/-}$ UT), ADLL (Npc1$^{-/-}$ ADLL), miglustat (Npc1$^{-/-}$ MIG), and combination (Npc1$^{-/-}$ miglustat & ADLL) treated mice with a minimum of 5 animals for each group.

Figure 20:
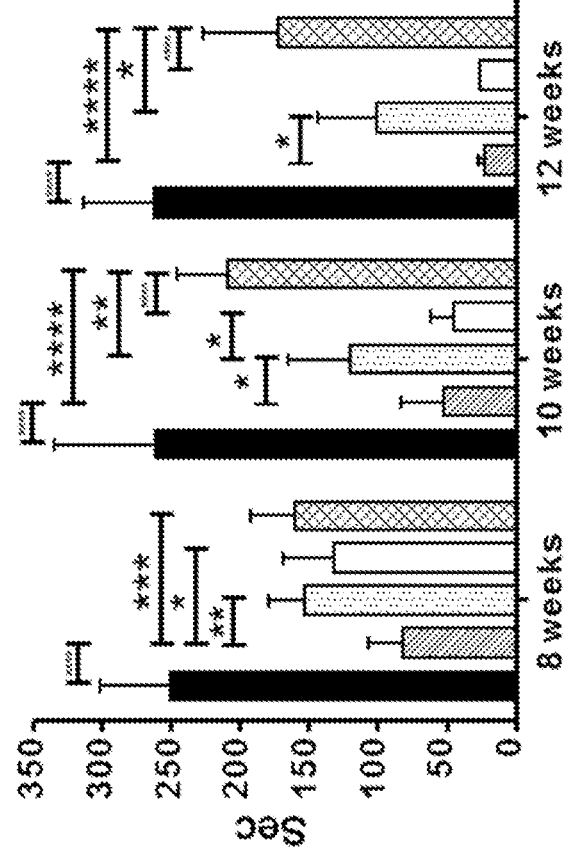

FIG. 20 is a bar graph showing the motor performance measurements at 8, 10, and 12 weeks of age (mean±SD, *p<0.043, p<0.0036, **p<0.0001 (2-way ANOVA)) for untreated wild type (Npc1$^{+/+}$ UT) and NPC1 (Npc1$^{-/-}$ UT) mice, and ADLL (Npc1$^{-/-}$ ADLL), miglustat (Npc1$^{-/-}$ MIG), and combination (Npc1$^{-/-}$ miglustat & ADLL) treated NPC1 mice with a minimum of 5 animals for each group.

Figure 21:
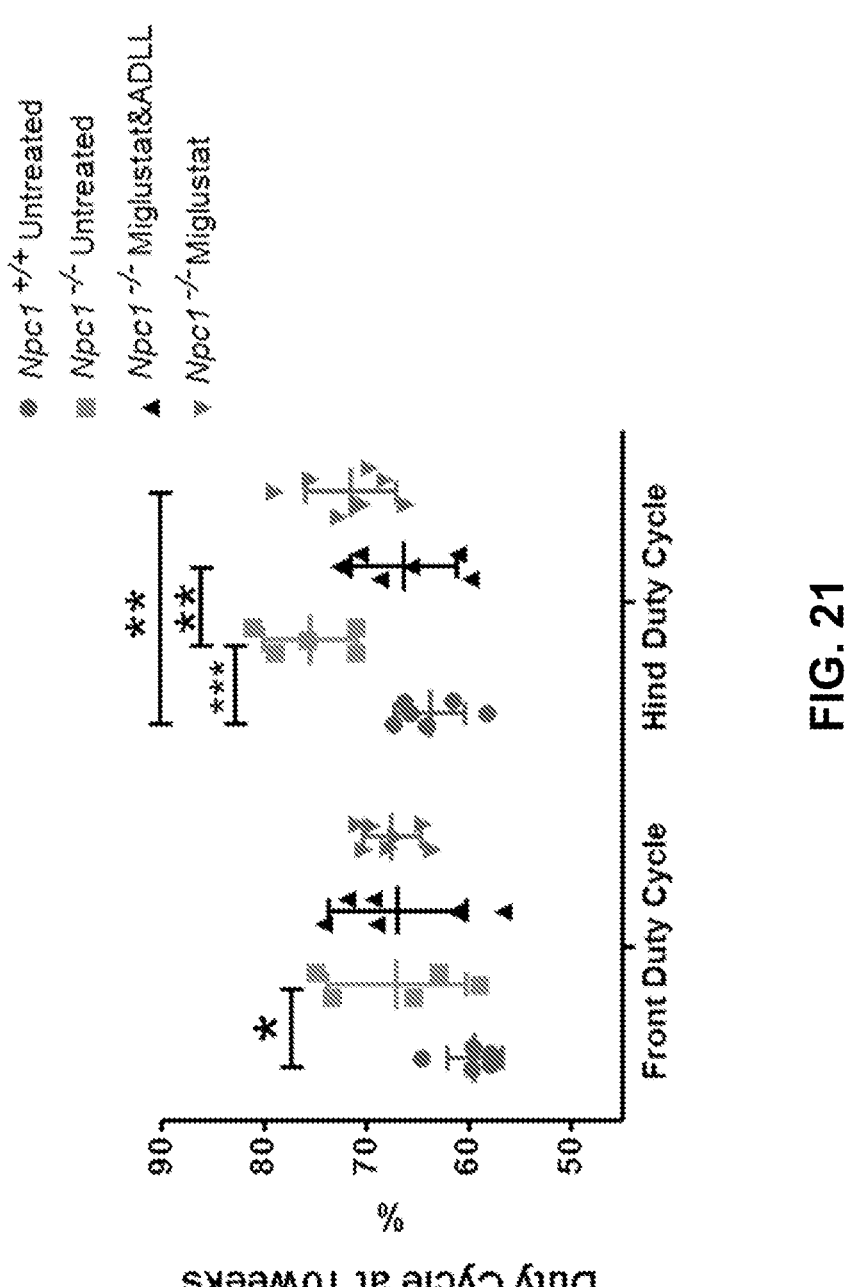

FIG. 21 is a column scatter graph showing the duty cycle measurements of the front and hind paws at 10 weeks of age (mean±SD, *p=0.011, p<0.0053, *p 0.0002 (2-way ANOVA)) for untreated wild type (Npc1$^{+/+}$ UT) and NPC1 (Npc1$^{-/-}$ UT) mice, and miglustat (Npc1$^{-/-}$ MIG) and combination (Npc1$^{-/-}$ miglustat & ADLL) treated NPC1 mice with a minimum of 5 animals for each group.

Figure 22:
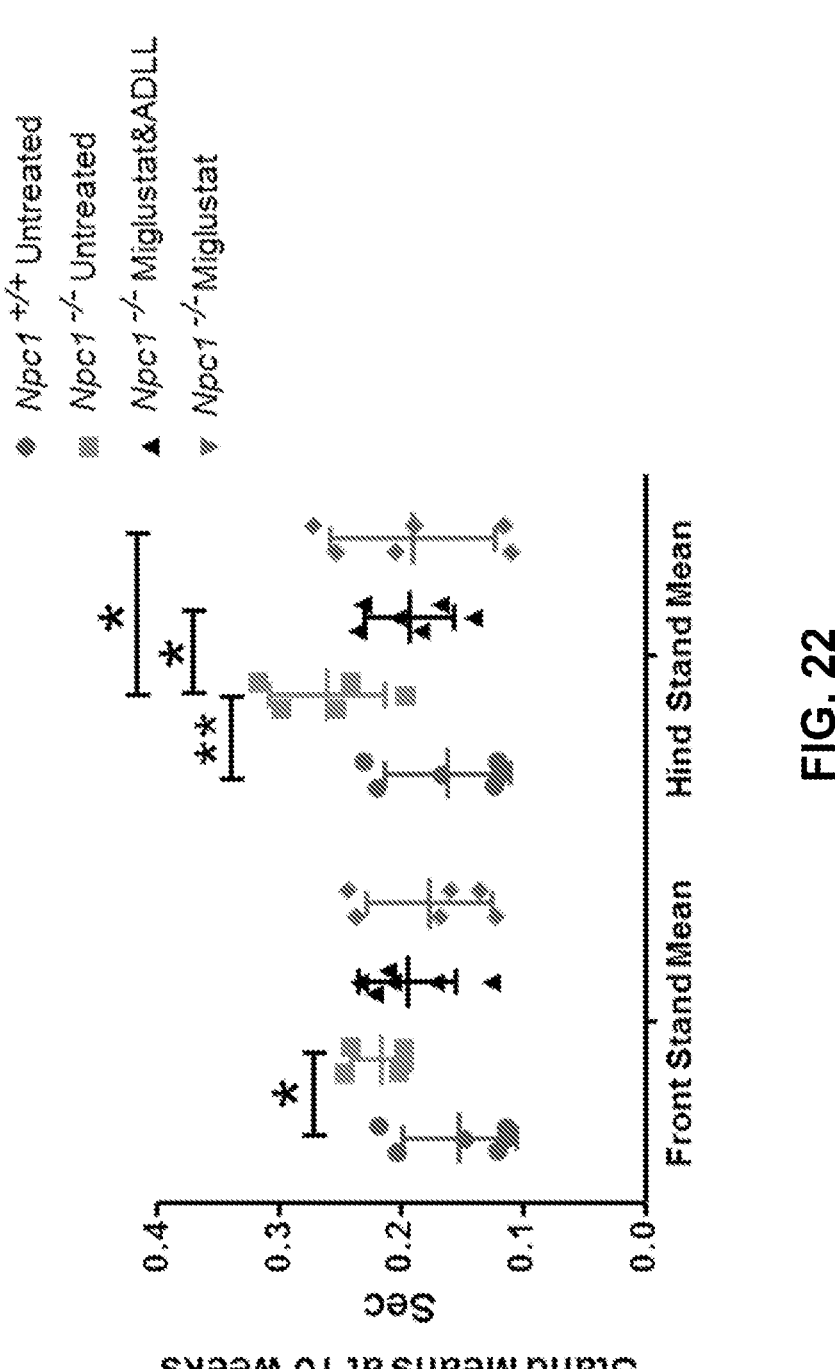

FIG. 22 is a column scatter graph showing the stand mean measurements of the front and hind paws at 10 weeks of age, (mean±SD, *p<0.033, **p<0.0016 (2-way ANOVA)) for untreated wild type (Npc1$^{-/-}$ UT) and NPC1 (Npc1$^{-/-}$ UT) mice, and miglustat (Npc1$^{-/-}$ MIG) and combination (Npc1 miglustat & ADLL) treated NPC1 mice with a minimum of 5 animals for each group.

Figure 23:
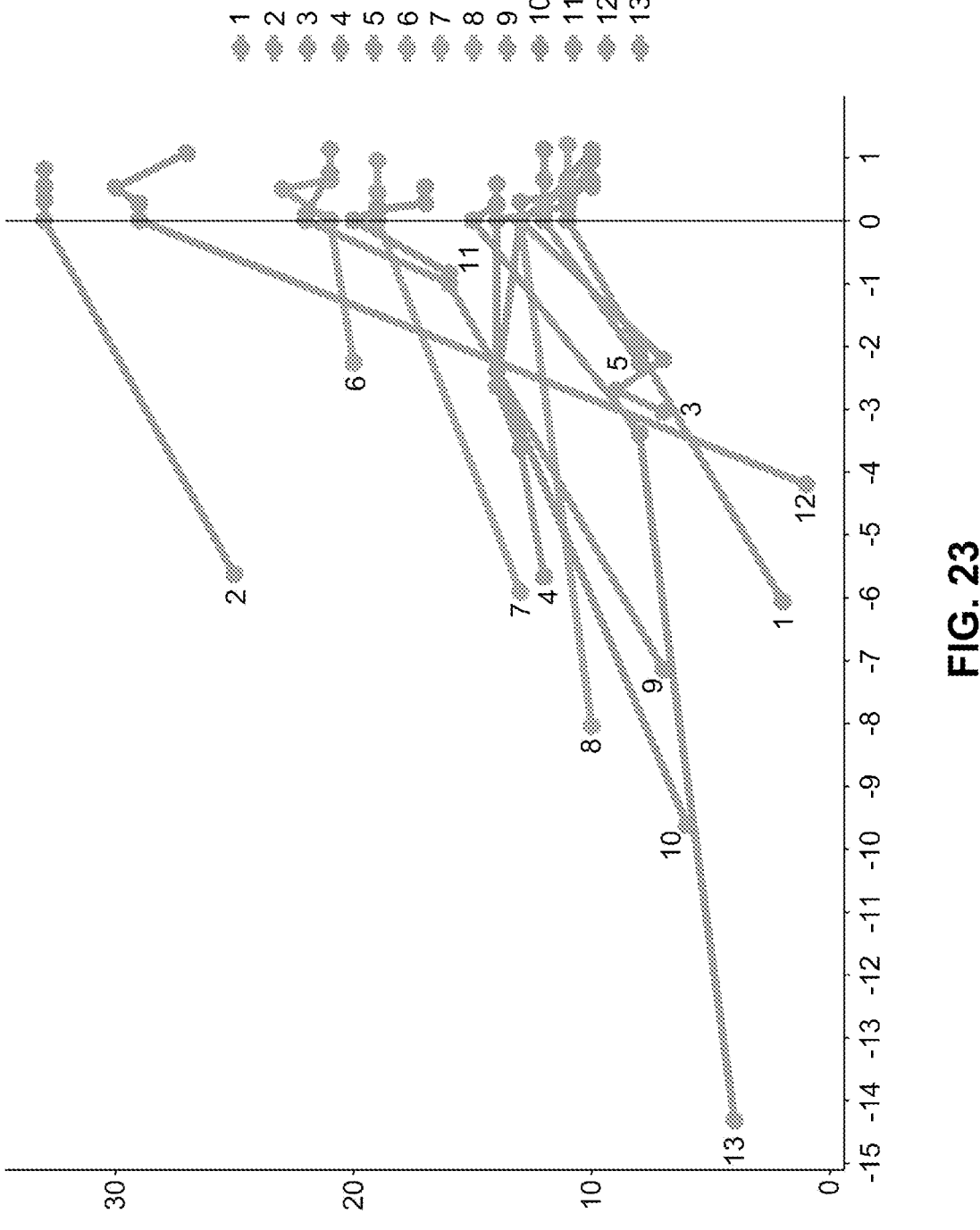

FIG. 23 is a line graph showing the clinical data from 13 adult NPC patients (for demographics see EXAMPLE 13 and General Methods) showing disease progression (clinical severity scale on the Y-axis) over time (Years, X-axis) prior to the initiation of treatment with ADLL (indicated by the vertical line).

Figure 24:
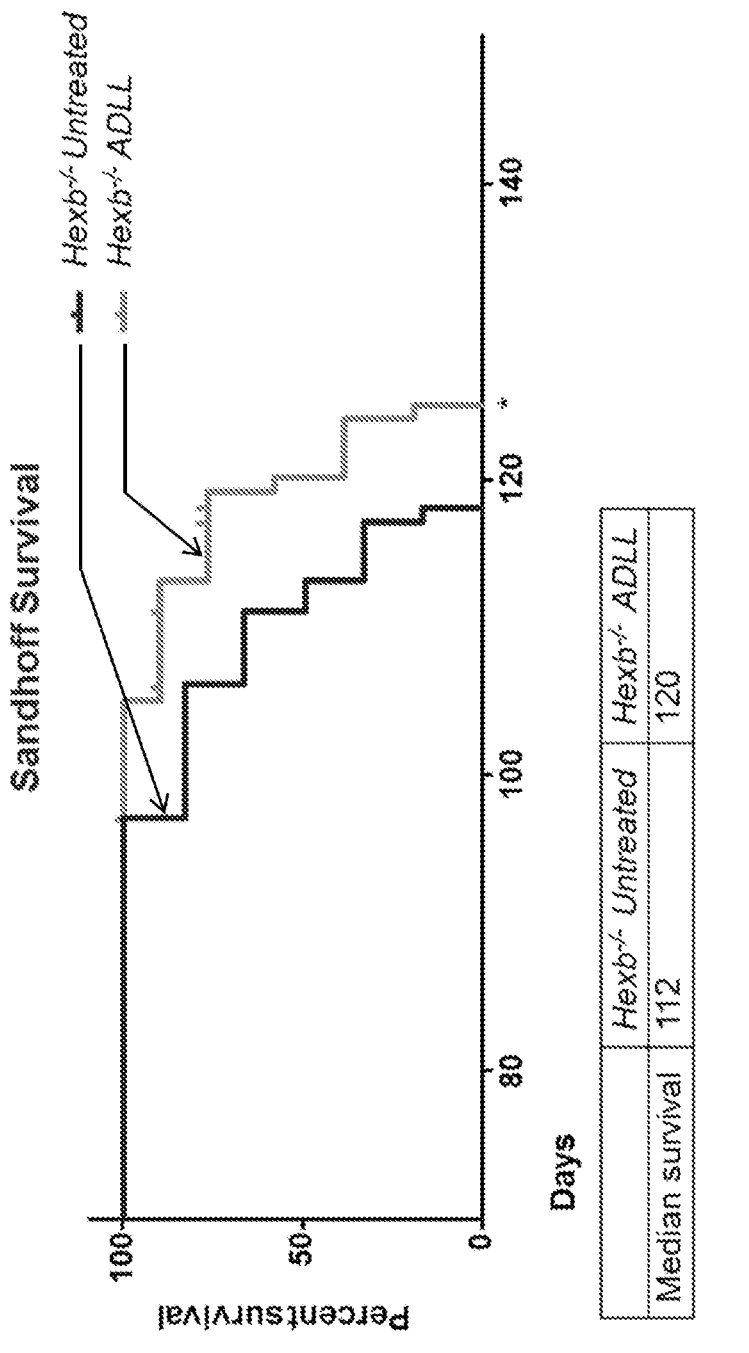

FIG. 24 is a line graph showing the changes in life expectancy ((%), mean±SD, *p=0.0157 (Gehan-Breslow-Wilcoxon test) n=5) and an analysis table in Sandhoff untreated (Hexb$^{-/-}$ UT) and ADLL (Hexb$^{-/-}$ ADLL) treated mice.

Figure 25:
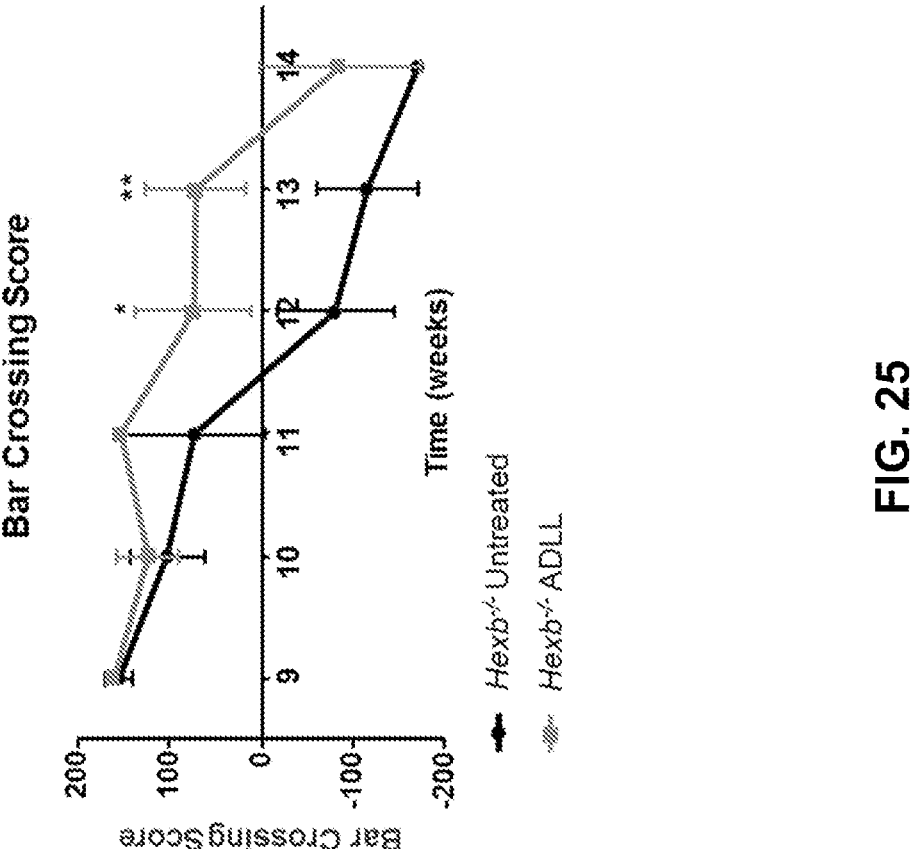

FIG. 25 is a line graph showing the bar crossing score (*p=0.0343, **p=0.0058, Mean±SD, 2-way ANOVA) in Sandhoff untreated (Hexb$^{-/-}$ UT) and ADLL (Hexb$^{-/-}$ ADLL) treated mice.

Figure 26:
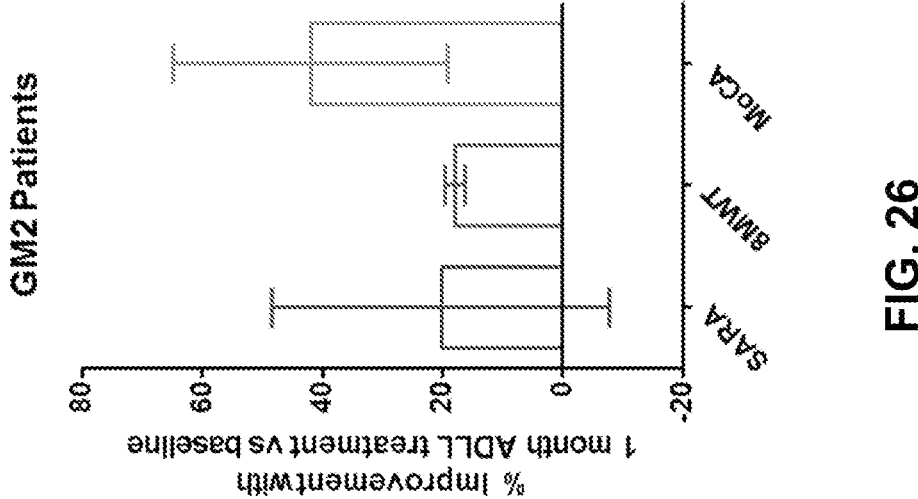

FIG. 26 is a bar graph showing the percent improvement in clinical scores in three patients with GM2 gangliosidosis at baseline and after one month on medication ADLL. The Scale for Assessment and Rating of Ataxia (SARA) changed by 20.3% and the 8-M-Walking-Test (8MWT) changed by 17.8%. Cognitive function, as assessed by Montreal Cognitive Assessment (MoCA) changed by 42.0%.

Figure 27B:
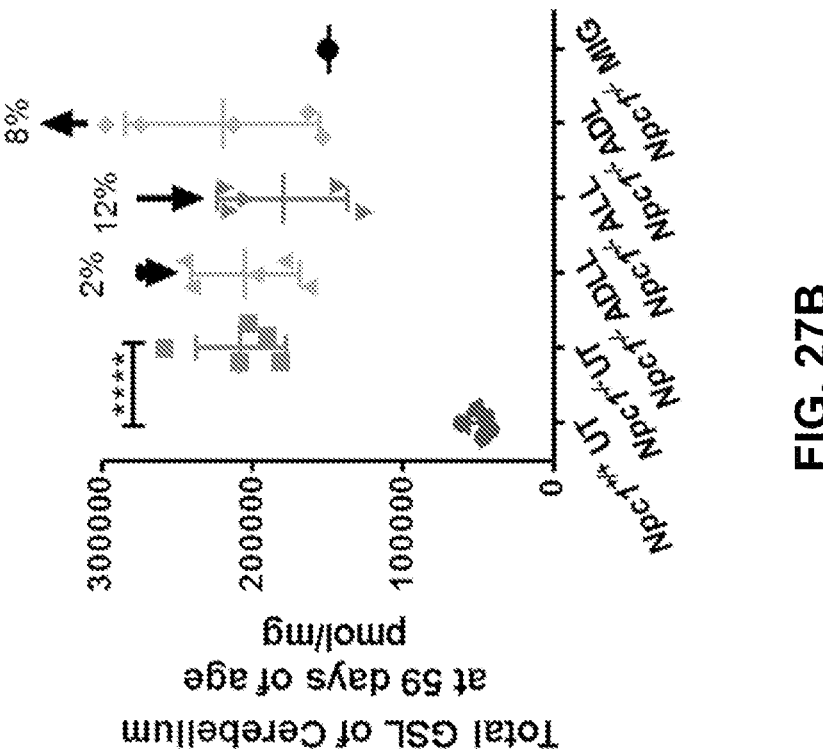
Figure 27A:
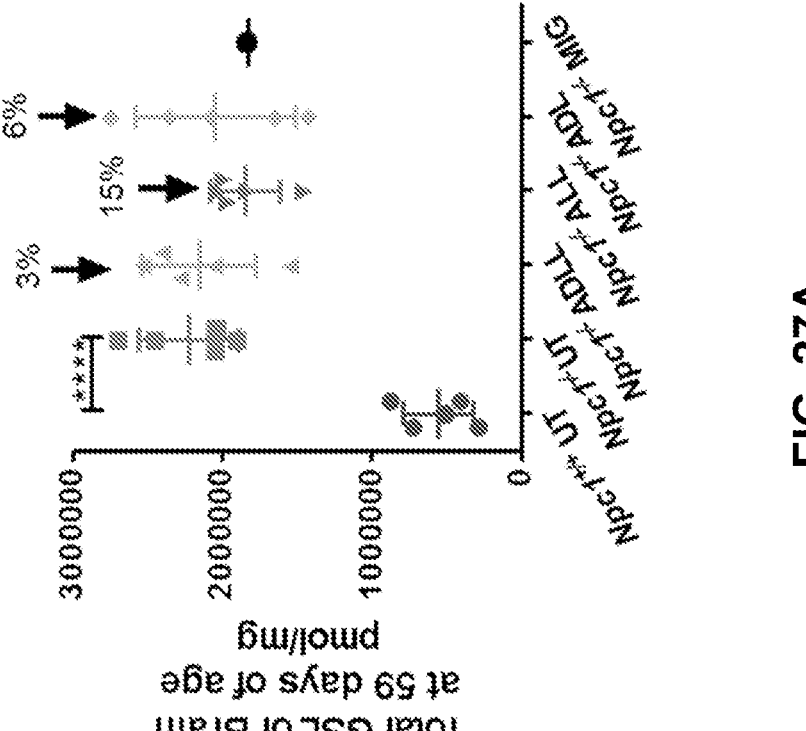

FIG. 27A is a column scatter graph showing the total GSL levels in the brain (mean±SD, *p<0.034, ***p=0.0004, (2-way ANOVA)) of untreated wild type (Npc1$^{-/-}$ UT) and NPC1 (Npc1$^{-/-}$ UT) mice, and ADLL (Npc1$^{-/-}$ ADLL), ALL (Npc1$^{-/-}$ ALL), ADL (Npc1$^{-/-}$ ADL) (5 animals per group), and miglustat (Npc1$^{-/-}$ MIG) (1 or 2 animals per group) treated NPC1 mice at 59 days of age.

FIG. 27B is a column scatter graph showing the total GSL levels in the cerebellum (mean±SD, (2-way ANOVA)) of untreated wild type (Npc1$^{+/+}$ UT) and NPC1 (Npc1$^{-/-}$UT) mice, and ADLL (Npc1$^{-/-}$ ADLL), ALL (Npc1$^{-/-}$ ALL), and ADL (Npc1$^{-/-}$ ADL) (5 animals per group), and miglustat (Npc1$^{-/-}$ MIG) (1 or 2 animals per group) treated NPC1 mice at 59 days of age.

Figure 27C:
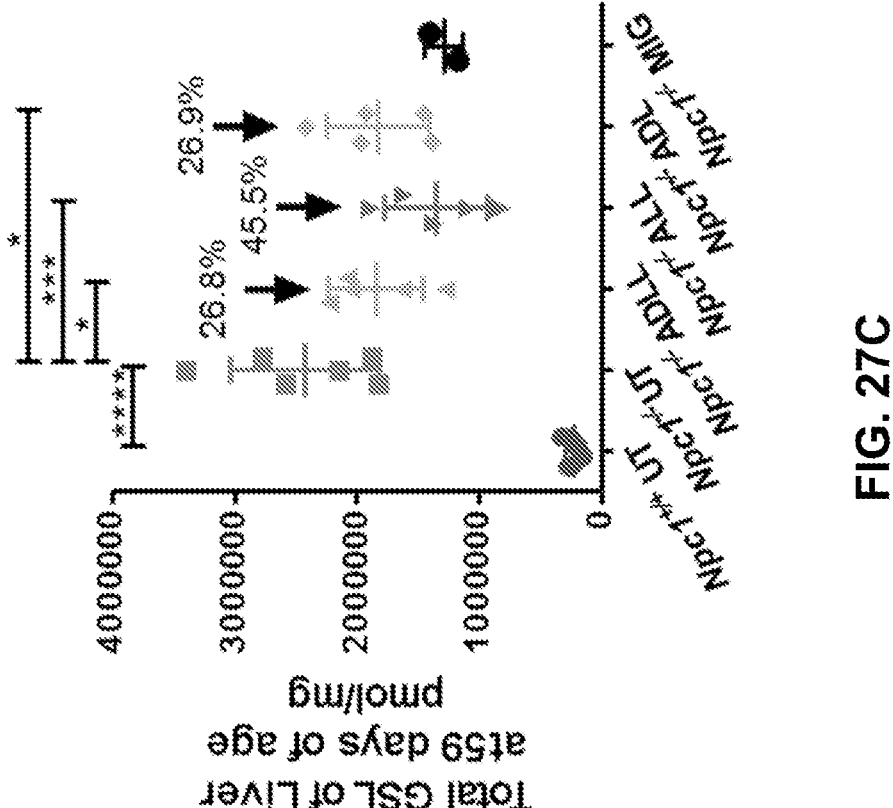

FIG. 27C is a column scatter graph showing the total GSL levels in the liver (mean±SD, (2-way ANOVA)) of untreated wild type (Npc1$^{+/+}$ UT) and NPC1 (Npc1$^{-/-}$ UT) mice, and ADLL (Npc1$^{-/-}$ ADLL), ALL (Npc1$^{-/-}$ ALL), ADL (Npc1$^{-/-}$ ADL) (5 animals per group), and miglustat (Npc1$^{-/-}$ MIG) (1 or 2 animals per group) treated NPC1 mice at 59 days of age.

DETAILED DESCRIPTION OF THE INVENTION

In one embodiment, the present disclosure provides acetyl-leucine in combination with miglustat for use in the treatment of a lysosomal storage disease (LSD) in a subject in need thereof, wherein the subject is naive to treatment with miglustat (referred to as Embodiment 1).

The present disclosure provides particular Embodiments 2-19 as follows.

Embodiment 2. A combination for use according to Embodiment 1, wherein acetyl-leucine and miglustat are administered simultaneously.

Embodiment 3. A combination for use according to Embodiment 2, wherein acetyl-leucine and miglustat are administered as a single pharmaceutical formulation.

Embodiment 4. A combination for use according to Embodiment 2, wherein acetyl-leucine and miglustat are administered as two separate pharmaceutical formulations.

Embodiment 5. A combination for use according to Embodiment 1, wherein acetyl-leucine and miglustat are administered sequentially.

Embodiment 6. A combination for use according to Embodiment 5, wherein acetyl-leucine is administered to the subject before miglustat.

Embodiment 7. A combination for use according to Embodiment 5, wherein acetyl-leucine is administered to the subject after miglustat.

Embodiment 8. A combination for use according to any one of Embodiments 5-7, wherein acetyl-leucine and miglustat are administered about 1 minute to about 6 hours apart.

Embodiment 9. A combination for use according to Embodiment 8, wherein acetyl-leucine and miglustat are administered about 1 minute to 3 hours apart.

Embodiment 10. A combination for use according to Embodiment 9, wherein acetyl-leucine and miglustat are administered about 1 minute to 1 hour apart.

Embodiment 11. A combination for use according to any one of Embodiments 1-10, wherein acetyl-leucine and miglustat are administered orally.

Embodiment 12. A combination for use according to any one of Embodiments 1-11, wherein acetyl-leucine is administered once, twice, or three times per day.

Embodiment 13. A combination for use according to any one of Embodiments 1-12, wherein miglustat is administered once, twice, or three times per day.

Embodiment 14. A combination for use according to any one of Embodiments 1-13, wherein about 3 g to about 15 g of acetyl-leucine is administered per day.

Embodiment 15. A combination for use according to any one of Embodiments 1-14, wherein about 0.05 g to about 2 g of miglustat is administered per day.

Embodiment 16. A combination for use according to any one of Embodiments 1-15, wherein acetyl-leucine and miglustat are administered as the first-line therapy to treat the lysosomal storage disease.

Embodiment 17. A combination for use according to any one of Embodiments 1-16, wherein the lysosomal storage disease is Niemann-Pick Disease Type C.

Embodiment 18. A combination for use according to any one of Embodiments 1-17, wherein the acetyl-leucine is N-acetyl-DL-leucine.

Embodiment 19. The method of any one of Embodiments 1-17, wherein the acetyl-leucine is N-acetyl-L-leucine.

In another embodiment, the present disclosure provides a method of treating a lysosomal storage disease in a subject in need thereof, the method comprising administering a combination of:

(i) a therapeutically effective amount of acetyl-leucine; and (ii) a therapeutically effective amount of miglustat, to the subject, wherein the subject is naive to treatment with miglustat (referred to as Embodiment I).

The present disclosure provides particular Embodiments II-XXI as follows.

Embodiment II. The method of Embodiment I, wherein acetyl-leucine and miglustat are administered simultaneously.

Embodiment III. The method of Embodiment II, wherein acetyl-leucine and miglustat are administered as a single pharmaceutical formulation.

Embodiment IV. The method of Embodiment II, wherein acetyl-leucine and miglustat are administered as two separate pharmaceutical formulations.

Embodiment V. The method of Embodiment I, wherein acetyl-leucine and miglustat are administered sequentially.

Embodiment VI. The method of Embodiment V, wherein acetyl-leucine is administered before miglustat.

Embodiment VII. The method of Embodiment V, wherein acetyl-leucine is administered after miglustat.

Embodiment VIII. The method of any one of Embodiments V-VII, wherein acetyl-leucine and miglustat are administered about 1 minute to about 6 hours apart.

Embodiment IX. The method of Embodiment VIII, wherein acetyl-leucine and miglustat are administered about 1 minute to 3 hours apart.

Embodiment X. The method of Embodiment IX, wherein acetyl-leucine and miglustat are administered about 1 minute to 1 hour apart.

Embodiment XI. The method of any one of Embodiments I-X, wherein acetyl-leucine and miglustat are administered orally.

Embodiment XII. The method of any one of Embodiments I-XI, wherein acetyl-leucine is administered once, twice, or three times per day.

Embodiment XIII. The method of any one of Embodiments I-XII, wherein miglustat is administered once, twice, or three times per day.

Embodiment XIV. The method of any one of Embodiments I-XIII, wherein about 3 g to about 15 g of acetyl-leucine is administered per day.

Embodiment XV. The method of any one of Embodiments I-XIV, wherein about 0.05 g to about 2 g of miglustat is administered per day.

Embodiment XVI. The method of any one of Embodiments I-XV, wherein acetyl-leucine and miglustat are administered as the first-line therapy to treat the lysosomal storage disease.

Embodiment XVII. The method of any one of Embodiments I-XVI, wherein the lysosomal storage disease is Niemann-Pick Disease Type C.

Embodiment XVIII. The method of any one of Embodiments I-XVII, wherein the acetyl-leucine is N-acetyl-DL-leucine.

Embodiment XIX. The method of any one of Embodiments I-XIX, wherein the acetyl-leucine is N-acetyl-L-leucine.

Embodiment XX. A kit comprising acetyl-leucine and miglustat for treating a lysosomal storage disease in a subject.

Embodiment XIX. The kit of Embodiment XX further comprising instructions for administering the acetyl-leucine and miglustat to the subject.

Definitions

As used herein, the singular forms "a," "an," and "the" include plural reference.

As used herein, the terms "approximately" and "about" should be generally understood to encompass±20% of a specified amount, frequency or value. Numerical quantities given herein are approximate unless stated otherwise, meaning that term "about" or "approximately" can be inferred when not expressly stated.

The terms "administer," "administration," or "administering" as used herein refer to (1) providing, giving, dosing and/or prescribing by either a health practitioner or his authorized agent or under his direction, the combination of acetyl-leucine and miglustat, and (2) putting into, taking or consuming by the subject or person himself or herself, acetyl-leucine and miglustat. Any reference to acetyl-leucine and miglustat include pharmaceutically acceptable salts of the same, even if not expressly stated.

A "pharmaceutically acceptable salt" as referred to herein, is any salt preparation that is appropriate for use in a pharmaceutical application. Pharmaceutically acceptable salts include, but are not limited to, amine salts, such as N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chloro-benzyl-2-pyrrolidin-1'-ylmethylbenzimidazole, diethylamine and other alkylamines, piperazine, tris(hydroxymethyl)aminomethane and the like; alkali metal salts, such as lithium, potassium, sodium and the like; alkali earth metal salts, such as barium, calcium, magnesium and the like; transition metal salts, such as zinc, aluminum and the like; other metal salts, such as sodium hydrogen phosphate, disodium phosphate and the like; mineral acids, such as hydrochlorides, sulfates and the like; and salts of organic acids, such as acetates, lactates, malates, tartrates, citrates, ascorbates, succinates, butyrates, valerates, fumarates and the like.

Acetyl-leucine and miglustat may be formulated and administered to a subject in accordance with known teachings in the art. For example, acetyl-leucine and miglustat may be formulated as separate pharmaceutical compositions. These pharmaceutical compositions may comprise the active agent, i.e., acetyl-leucine or miglustat, and one or more pharmaceutically acceptable carriers. Acetyl-leucine and miglustat may also be formulated as single pharmaceutical composition comprising both active agents and one or more pharmaceutically acceptable carriers.

The pharmaceutical compositions comprising acetyl-leucine and miglustat, either separately or together in a single composition, may take any of a number of different forms depending on the manner in which they are to be used. Thus, for example, the pharmaceutical compositions may be in the form of a powder, tablet, capsule, liquid, ointment, cream, gel, hydrogel, aerosol, spray, micellar solution, transdermal patch, liposome suspension, or any other suitable form that may be administered to a subject in need of treatment.

A "pharmaceutically acceptable carrier" as referred to herein, is any known compound or combination of known compounds, e.g., excipients, carriers, etc., that are known to those skilled in the art to be useful in formulating pharmaceutical compositions. It will be appreciated that the carrier of the pharmaceutical composition should be one which is tolerated by the subject to whom it is given.

In one embodiment, the pharmaceutically acceptable carrier may be a solid, and the composition may be in the form of a powder or tablet. A solid pharmaceutically acceptable carrier may include, but is not limited to, one or more substances which may also act as flavouring agents, buffers, lubricants, stabilisers, solubilisers, suspending agents, wetting agents, emulsifiers, dyes, fillers, glidants, compression aids, inert binders, sweeteners, preservatives, dyes, coatings, or tablet-disintegrating agents. The carrier may also be an encapsulating material. In powders, the carrier may be a finely divided solid that is in admixture with the finely divided active agents according to the invention. In tablets, the active agent may be mixed with a carrier having the necessary compression properties in suitable proportions and compacted in the shape and size desired. The powders and tablets may, for example, contain up to 99% of the active agents. Suitable solid carriers include, for example, calcium phosphate, magnesium stearate, talc, sugars, lactose, dextrin, starch, gelatin, cellulose, polyvinylpyrrolidine, low melting waxes and ion exchange resins. In another embodiment, the pharmaceutically acceptable carrier may be a gel and the composition may be in the form of a cream or the like.

The carrier may include, but is not limited to, one or more excipients or diluents.

Examples of such excipients are gelatin, gum arabicum, lactose, microcrystalline cellulose, starch, sodium starch glycolate, calcium hydrogen phosphate, magnesium stearate, talcum, colloidal silicon dioxide, and the like.

In another embodiment, the pharmaceutically acceptable carrier may be a liquid.

In one embodiment, the pharmaceutical composition is in the form of a solution. Liquid carriers are used in preparing solutions, suspensions, emulsions, syrups, elixirs and pressurized compositions. Acetyl-leucine and/or miglustat may be dissolved or suspended in a pharmaceutically acceptable liquid carrier such as water, an organic solvent, a mixture of both or pharmaceutically acceptable oils or fats. The liquid carrier may contain other suitable pharmaceutical additives such as solubilisers, emulsifiers, buffers, preservatives, sweeteners, flavouring agents, suspending agents, thickening agents, colours, viscosity regulators, stabilizers or osmoregulators. Suitable examples of liquid carriers for oral and parenteral administration include water (partially containing additives as above, e.g. cellulose derivatives, such as sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier may also be an oily ester such as ethyl oleate and isopropyl myristate. Sterile liquid carriers are useful in sterile liquid form compositions for parenteral administration. The liquid carrier for pressurised compositions may be a halogenated hydrocarbon or other pharmaceutically acceptable propellant.

Liquid pharmaceutical compositions, which are sterile solutions or suspensions, may be utilised by, for example, intramuscular, intrathecal, epidural, intraperitoneal, intravenous and subcutaneous injection. The active agent may be prepared as a sterile solid composition that may be dissolved or suspended at the time of administration using sterile water, saline, or other appropriate sterile injectable medium.

The compositions may be administered orally in the form of a sterile solution or suspension containing other solutes or suspending agents (for example, enough saline or glucose to make the solution isotonic), bile salts, acacia, gelatin, sorbitan monoleate, polysorbate 80 (oleate esters of sorbitol and its anhydrides copolymerized with ethylene oxide) and the like. The compositions may also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

In one embodiment, the pharmaceutical composition of both acetyl-leucine and miglustat is a solid oral dosage form, such as a tablet. In tablets, the active agent may be mixed with a vehicle, such as a pharmaceutically acceptable carrier, having the necessary compression properties in suitable proportions and compacted in the shape and size desired. The tablets may contain up to 99% by weight of the active agents.

Pharmaceutical compositions in solid oral dosage form, such as tablets, may be prepared by any method known in the art of pharmacy. Pharmaceutical compositions are usually prepared by mixing the active agent with conventional pharmaceutically acceptable carriers.

A tablet may be formulated as is known in the art. Tanganil®, for example, includes wheat starch, pregelatinised maize (corn) starch, calcium carbonate and magnesium stearate as excipients. The same, or similar, excipients, for example, may be employed with the present disclosure.

The composition of each 700 mg Tanganil® tablet is as follows: 500 mg acetyl-DL-leucine, 88 mg wheat starch, 88 mg pregelatinised maize (corn) starch, 13 mg calcium carbonate and 11 mg magnesium stearate. The same tablets, for example, may be employed in the methods of the present disclosure.

As discussed above, acetyl-leucine and miglustat may be formulated and administered as a pharmaceutical composition taking any number of different forms. For example, acetyl-leucine may be formulated as a pharmaceutical composition to facilitate its delivery across the blood-brain barrier. As a further example, acetyl-leucine may be formulated as a pharmaceutical composition for bypassing the blood-brain barrier.

In one embodiment, the pharmaceutical composition, e.g., comprising acetyl-L-leucine, or salt thereof, is formulated for nanodelivery, e.g., colloidal drug-carrier systems. Suitable examples include but are not limited to liposomes, nanoparticles (e.g., polymeric, lipid and inorganic nanoparticles), nanogels, dendrimers, micelles, nanoemulsions, polymersomes, exosomes, and quantum dots. See, e.g., Patel et al., "Crossing the Blood-Brain Barrier: Recent Advances in Drug Delivery to the Brain," CNS Drugs 31:109-133 (2017); Kabanov et al., "New Technologies for Drug Delivery across the Blood Brain Barrier," Curr Pharm Des., 10(12):1355-1363 (2004); Cheng et al., "Highly Stabilized Curcumin Nanoparticles Tested in an In Vitro Blood—Brain Barrier Model and in Alzheimer's Disease Tg2576 Mice," The AAPS Journal, vol. 15, no. 2, pp. 324-336 (2013); Lande et al. "Production of L-Leucine Nanoparticles under Various Conditions Using an Aerosol Flow Reactor Method," Journal of Nanomaterials, vol. 2008, article ID 680897 (2008).

In one embodiment, the pharmaceutical composition, e.g., comprising N-acetyl-L-leucine, or salt thereof, is formulated for direct delivery to the central nervous system (CNS), such as by injection or infusion. Formulations for and methods of direct delivery to the CNS are known in the art. See, e.g., U.S. Pat. No. 9,283,181. Examples of such administration include but are not limited to intranasal, intraventricular, intrathecal, intracranial, and delivery via nasal mucosal grafting. In one embodiment, the pharmaceutical composition is administered by intracerebroventricular infusion.

In one embodiment, the pharmaceutical composition is formulated for (and administered by) intranasal delivery. See, e.g., Hanson et al., "Intranasal delivery bypasses the blood-brain barrier to target therapeutic agents to the central nervous system and treat neurodegenerative disease," BMC Neurosci. 9(Suppl 3): S5 (2008). In one embodiment, the pharmaceutical composition is formulated for (and administered by) delivery via a nasal mucosal graft. In one embodiment, the pharmaceutical composition is formulated for (and administered by) intracerebroventricular injection or infusion. In another embodiment, the pharmaceutical composition is formulated for (and administered by) intrathecal intracisternal injection or infusion. In one embodiment, the pharmaceutical composition is formulated for (and administered by) intrathecal lumbar injection or infusion.

Various techniques may be used including, without limitation, injection through a burrhole or cisternal or lumbar puncture or the like as known in the art. Various devices, whether internal (e.g., implanted) or external, may be used for delivery as known in the art, such as pumps, catheters, reservoirs, etc. In one embodiment, the administration interval is once every two weeks.

"Lysosomal storage disease" or "LSD" refers to any disorder that involves dysfunction or disruption in the late endosomal/lysosomal system and the accumulation of undigested or partially digested macromolecules. The LSD may involve increased storage of lipids or non-lipids. All LSDs are within the scope of the present disclosure.

In one embodiment, the LSD is chosen from any of glycogen storage disease, mucopolysaccaridoses, mucolipidoses, oligosaccharidoses, lipidoses, sphingolipidoses, and lysosomal transport diseases.

The glycogen storage disease may be chosen from Infantile-onset Pompe disease, Lateonset Pompe disease and Danon disease.

The mucopolysaccharidoses may be chosen from any of MPS IH, MPS I H-S, MPS IS, MPS IIA, MPS IIB, MPS IIIA-D, MPS IVA, MPS VI, MPS VII and MPS IX. In one embodiment, the mucopolysaccharidosis is 1VIPS III or 1VIPS VII. In one embodiment, the mucopolysaccharidosis is MPS TIM.

The mucolipidoses may be chosen from any of mucolipidosis I, mucolipidosis II, mucolipidosis III, and mucolipidosis IV. In one embodiment the mucolipidosis is mucolipidosis II or mucolipidosis III.

The oligosaccharidoses may be chosen from any of beta-mannosidosis, alphafucosidosis, and aspartylglucosaminuria. In one embodiment, the oligosaccharidosis is aspartylglucosaminuria.

The lipidoses may be chosen from any of Niemann-Pick disease type C, Niemann-Pick disease type D, neuronal ceroid lipofuscinoses (Type I to X inclusive), and Wolman disease. In one embodiment, the lipidosis is Niemann-Pick disease type C.

The sphingolipidoses may be chosen from any of Niemann-Pick disease type A/B, Gaucher disease types I, II, and III, Krabbe disease, Fabry disease, Schindler Disease, GM1 gangliosidosis, Morquio B disease, GM2 gangliosidoses, metachromatic leukodystrophy, Farber disease, multiple sulfatase deficiency, lysosomal acid lipase deficiency and galactosialidosis. In one embodiment, the sphingolipidoses are chosen from Niemann-Pick disease type A, GM1 gangliosidosis, Tay-Sachs disease, the AB variant of Tay-Sachs disease, and Sandhoff disease.

The lysosomal transport diseases may be chosen from cystinosis, pycnodysostosis, sialic acid storage disease and infantile free sialic acid storage disease.

The LSD may be a primary lysosomal hydrolase defect, a post-translational processing defect of lysosomal enzymes, a trafficking defect for lysosomal enzymes, a defect in lysosomal enzyme protection, a defect in soluble non-enzymatic lysosomal proteins, a transmembrane (non-enzyme) protein defect or an unclassified defect.

In one embodiment, the LSD is chosen from a primary lysosomal hydrolase defect. Primary lysosomal hydrolase defects include, but are not limited to, Tay-Sachs disease (($\beta$-hexosaminidase A defect), Sandhoff disease (($\beta$-hexosaminidase A+B defect), Fabry disease ($\alpha$-galactosidase A defect), Krabbe disease (($\beta$-galactosyl ceramidase defect), Niemann-Pick Type A and B (sphingomyelinase defect), metachromatic leukodystrophy (arylsulphatase A defect), MIPS IH (Hurler syndrome; $\alpha$-iduronidase defect), 1VIPS IS (Scheie syndrome; $\alpha$-iduronidase defect), MPS IH-S (Hurler-Scheie syndrome; $\alpha$-iduronidase defect), MIPS II (Hunter syndrome; iduronate sulphatase defect), MPS IIIA (Sanfilippo A syndrome; heparan sulphamidase defect), MPS IIIB (Sanfilippo B syndrome; acetyl $\alpha$-glucosaminidase defect), MPS IIIC (Sanfilippo C syndrome; acetyl CoA: $\alpha$-glucosaminide N-acetyltransferase defect), MIPS IIID (Sanfilippo D syndrome; N-acetyl glucosamine-6-sulphatase defect), MPS IV A (Morquio A disease; acetyl galactosamine-6-sulphatase defect), MPS IVB (Morquio B disease; ($\beta$-galactosidase defect), MPS V (redesignated MPS IS), MPS VI (Maroteaux Lamy Syndrome; acetyl galactosamine-4-sulphatase (arylsulphatase B) defect), MPS VII (Sly Syndrome; ($\beta$-glucuronidase defect), MPS IX (hyaluronidase defect), Wolman/cholesteryl ester storage disease (WD; acid lipase defect), Pompe disease (Type II; $\alpha$-1,4-glucosidase defect), aspartylglucosaminuria (glycosylasparaginase defect), fucosidosis ($\alpha$-fucosidase defect), $\alpha$-mannosidosis ($\alpha$-mannosidase defect), $\beta$-mannosidosis 5 (($\beta$-mannosidase defect), Schindler disease (N-acetylgalactosaminidase defect), sialidosis/ML I ($\alpha$-neuraminidase defect), infantile neuronal ceroid lipofuscinosis (CLN1; palmitoyl protein thioesterase defect), late infantile neuronal ceroid lipofuscinosis (CLN2; carboxypeptidase defect), early infantile GM1 gangliosidosis, late infantile GM1 gangliosidosis, adult infantile GM1 gangliosidosis, Gaucher Disease Type 1 (Non-Neuronopathic), Gaucher Disease Type 2/3 (Neuronopathic), Neuronal Ceroid Lipofuscinosis Type 4 (CLN4; Kufs disease; Adult NCL; palmotoyl-protein thioesterase-1 deficiency (Type A); Cathepsin F deficiency (Type B)), Neuronal Ceroid Lipofuscinosis Type 10 (CLN10; Congenital Cathepsin D Deficiency), Pycnodysostosis (Cathepsin K defect), Infantile-Onset Pompe Disease, Late-Onset Pompe Disease, Farber Disease (Farber's lipogranulomatosis; ceramidase deficiency; Fibrocytic dysmucopolysaccharidosis; Lipogranulomatosis) and Galactosialidosis (protective protein cathepsin A defect, PPCA defect). In one embodiment, the primary lysosomal hydrolase defect is chosen from Tay-Sachs disease, Sandhoff disease, Niemann-Pick Type A, Niemann-Pick Type B, neuronal ceroid lipofuscinoses, Gaucher disease, Fabry disease, Krabbe disease, GM1 gangliosidosis, GM2 gangliosidosis, metachromatic leukodystrophy, and Farber disease. In one embodiment, the primary lysosomal hydrolase defect is chosen from Tay-Sachs disease, Sandhoff disease, Niemann-Pick Type A, Niemann-Pick Type B, and GM1 gangliosidosis.

In one embodiment, the LSD is NPC.

In one embodiment, the LSD is Gaucher disease.

In one embodiment, the LSD is GM1 gangliosidosis.

In one embodiment, the LSD is GM1 gangliosidosis.

The term "acetyl-leucine" refers collectively to N-acetyl-DL-leucine (ADLL), or a pharmaceutically acceptable salt thereof; N-acetyl-D-leucine (ADL), or a pharmaceutically acceptable salt thereof; and N-acetyl-L-leucine (ALL), or a pharmaceutically acceptable salt thereof. The term acetyl-leucine includes isotopically-labelled analogs of N-acetyl-DL-leucine, N-acetyl-D-leucine, and N-acetyl-L-leucine, wherein one or more atoms are replaced by an atom having a different atomic mass or mass number. Examples of isotopes that can be incorporated include isotopes of hydrogen, carbon, nitrogen, and oxygen, such as $^2H$ (or deuterium (D)), 3H, $^{11}C$, $^{13}C$, $^{14}C$, $^{15}N$, $^{18}O$, and $^{17}O$. In one embodiment, provided is an isotopically-labelled analog of acetyl-leucine, wherein substantially all of the atoms at a position within acetyl-leucine are replaced by an atom having a different atomic mass or mass number. In another embodiment, provided is an isotopically-labelled analog of acetyl-leucine, wherein a portion of the atoms at a position within acetyl-leucine are replaced, e.g., acetyl-leucine is enriched at one or more positions with an atom having a different atomic mass or mass number. Isotopically-labelled acetyl-leucine can be prepared by methods known in the art.

In one embodiment, the N-acetyl-DL-leucine, N-acetyl-D-leucine, or N-acetyl-L-leucine is not isotopically-labelled.

In one embodiment, the isotopically-labelled analog is a deuterated analog of N-acetyl-DL-leucine, N-acetyl-D-leucine, or N-acetyl-L-leucine, wherein one or more hydrogen atoms are replaced with deuterium. In one embodiment, one hydrogen atom of N-acetyl-DL-leucine, N-acetyl-D-leucine, or N-acetyl-L-leucine is replaced with deuterium. In another embodiment, two hydrogen atoms of N-acetyl-DL-leucine, N-acetyl-D-leucine, or N-acetyl-L-leucine are replaced with deuterium. In another embodiment, three hydrogen atoms of N-acetyl-DL-leucine, N-acetyl-D-leucine, or N-acetyl-L-leucine are replaced with deuterium. In another embodiment, four hydrogen atoms of N-acetyl-DL-leucine, N-acetyl-D-leucine, or N-acetyl-L-leucine are replaced with deuterium. In another embodiment, five hydrogen atoms of N-acetyl-DL-leucine, N-acetyl-D-leucine, or N-acetyl-L-leucine are replaced with deuterium. In another embodiment, six hydrogen atoms of N-acetyl-DL-leucine, N-acetyl-D-leucine, or N-acetyl-L-leucine are replaced with deuterium.

In one embodiment, the acetyl-leucine used in the methods of the present disclosure is N-acetyl-DL-leucine, or a deuterated analog thereof. In another embodiment, the acetyl-leucine used in the methods of the present disclosure is N-acetyl-D-leucine, or a deuterated analog thereof. In another embodiment, the acetyl-leucine used in the methods of the present disclosure is N-acetyl-L-leucine, or a deuterated analog thereof.

In another embodiment, the acetyl-leucine used in the methods of the present disclosure is N-acetyl-DL-leucine. In another embodiment, the acetyl-leucine used in the methods of the present disclosure is N-acetyl-D-leucine. In another embodiment, the acetyl-leucine used in the methods of the present disclosure is N-acetyl-L-leucine.

"Miglustat" refers to 1,5-(butylimino)-1,5-dideoxy-D-glucitol (also known as N-butyl-deoxynojirimycin).

"Administered in combination" and similar phrases mean that two agents, e.g., (1) acetyl-DL-leucine, acetyl-D-leucine, or acetyl-L-leucine; and (2) miglustat, are administered concurrently to the subject being treated. In one embodiment, acetyl-DL-leucine, acetyl-D-leucine, or acetyl-L-leucine and miglustat are administered in combination as a first line therapy to treat a LSD.

"First line therapy" means a treatment regimen generally accepted or recommended by the medical establishment or a regulatory authority, e.g., the U.S. Food and Drug Administration or the European Medicines Agency, for the initial treatment of a condition, disease, or disorder.

"Concurrently" means that each active agent is administered either (i) simultaneously; or (ii) sequentially in any order at different points in time. A combination of two agents is considered to be administered simultaneously if each agent is administered to the subject less than 1 minute apart. If not administered simultaneously, it is meant that both agents are administered to a subject in a sequence and sufficiently close in time so as to provide the desired therapeutic effect and can act in concert to treat a LSD.

In one embodiment, acetyl-leucine and miglustat are administered separately, in any appropriate form and by any suitable route. In one embodiment, both acetyl-leucine and miglustat are orally administered to the subject as tablets.

In one embodiment, acetyl-leucine is administered to the subject 1 minute to 24 hours before the administration of miglustat to the subject. For example, acetyl-leucine is administered 5 minutes, 10 minutes, 15 minutes, 30 minutes, 45 minutes, 1 hour, 2 hours, 4 hours, 6 hours, or 12 hours before the administration of miglustat to a subject.

In another embodiment, acetyl-leucine is administered simultaneously with miglustat to the subject.

In another embodiment, acetyl-leucine is administered to the subject 1 minute to 24 hours after the administration of miglustat to the subject. For example, acetyl-leucine is administered 5 minutes, 10 minutes, 15 minutes, 30 minutes, 45 minutes, 1 hour, 2 hours, 4 hours, 6 hours, or 12 hours after, the administration of miglustat to a subject.

In another embodiment, acetyl-leucine and miglustat are administered to the subject about 1 minute to about 24 hours apart. For example, acetyl-leucine and miglustat are administered about 1 minute apart, 5 minutes apart, 10 minutes apart, 30 minutes apart, 45 minutes apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, or 11 hours to 12 hours apart.

"Naive to treatment with miglustat" and similar phrases means that miglustat has not previously been administered to the subject to treat a LSD.

"Subject" means a human.

"Subject in need thereof" means a human who has a LSD and is need of treatment.

The subject may or may not have been diagnosed a LSD. For example, the subject may not yet have a diagnosis (clinical or otherwise) of a LSD, but may have one or more symptoms of a LSD. The subject may also have a biochemical or other similar identifiable marker of a LSD.

A "therapeutically effective amount" of acetyl-leucine or miglustat is any amount of either active agent which, when administered to a subject, is the amount that is needed to produce the desired effect, which, for the present disclosure, can be therapeutic and/or prophylactic. The dose may be determined according to various parameters, such as the specific active agent used; the age, weight and condition of the patient to be treated; the route of administration; and the required regimen. A physician will be able to determine the required route of administration and dosage for any particular patient. For example, a daily dose of either active agent may be from about 10 to about 225 mg per kg, from about 10 to about 150 mg per kg, or from about 10 to about 100 mg per kg of body weight.

As used herein, "treating" or "treatment" refers to any indicia of success in preventing, arresting, or ameliorating a disease, disorder, condition, or syndrome, e.g., a LSD, in a subject, and/or preventing, arresting, or ameliorating any one or more symptoms a disease, disorder, condition, or syndrome, e.g., a LSD, in a subject, including any objective or subjective parameter such as abatement; remission; preventing, diminishing, inhibiting, or eliminating one or more symptoms; making the disease, disorder, condition, or syndrome more tolerable to the subject; slowing in the worsening of the disease, disorder, condition, or syndrome; or improving the physical or mental well-being of the subject in need thereof.

The terms "treating" or "treatment" also encompasses inducing inhibition, regression, or stasis of the disease, disorder, condition, or syndrome, e.g., a LSD. For example, treatment of a patient or subject in need of treatment for a LSD includes reducing a symptom of the LSD in the subject, inducing clinical response, inhibiting or reducing progression of the LSD, or inhibiting or reducing a complication of the LSD.

Preventing, arresting, or ameliorating an injury or pathology of a disease, disorder, condition, or syndrome, e.g., a LSD, e.g., NPC, such as preventing, diminishing, inhibiting, or eliminating one or more symptoms of disease, disorder, condition, or syndrome can be based on objective and/or subjective parameters, including, e.g., the results of physical examination(s), neurological examination(s), and/or psychiatric evaluation(s). The success of treatment for certain diseases e.g., a LSD, may be measured or evaluated by, for example, comparing the severity of the disease, e.g., objective and/or subjective parameters of the LSD, e.g., NPC, before treatment with acetyl-leucine and miglustat is initiated, with the severity of the disease following the initiation of treatment with acetyl-leucine and miglustat. For example, the severity of NPC may be assessed using a scale, index, rating, or score. In one embodiment, the treatment described herein improves such an assessment from a value or degree characteristic of a symptomatic subject to a value or degree characteristic of a non-symptomatic subject. In one embodiment, the treatment described herein improves such an assessment compared to a baseline. The baseline may be, for example, the subject's condition before initiating any treatment for the disease, e.g., NPC, or before initiating treatment for the disease with a acetyl-leucine and miglustat. Alternatively, the baseline may be, for example, the subject's condition after a certain time period on treatment for the disease. In one embodiment, treatment with acetyl-leucine and miglustat as described herein improves the subject's assessment (e.g., scale, index, rating, or score of objective and/or subjective parameters) compared to a baseline by at least 10%, at least 20%, at least 30%, at least 40%, or at least 50%. In one embodiment, assessment is improved by at least 60%, at least 70%, at least 80%, at least 90%, or 100%.

In one embodiment, acetyl-leucine is administered at a dose ranging from about 500 mg to about 30 g per day. For example acetyl-leucine is administered at a dose ranging from about 500 mg to about 15 g per day, a dose ranging from about 1.5 g to about 10 g per day, optionally by solid oral or liquid oral route. N-Acetyl-DL-leucine, may be administered, for example, in a dose according to that of Tanganil®, which is prescribed to adults in a dose of 1.5 g to 2 g per day, 3-4 tablets in two doses, morning and evening.

If a single enantiomer of acetyl-leucine, i.e., N-acetyl-D-leucine or N-acetyl-L-leucine, is administered the doses may be reduced accordingly. For instance, if only N-acetyl-L-leucine or if only N-acetyl-D-leucine is administered, the dose may range from about 250 mg to about 15 g per day, range from about 250 mg to about 10 g per day, or range from about 250 mg to about 5 g per day, such as from about 0.75 g to about 5 g per day.

In one embodiment, the administered dose ranges of acetyl-leucine are from about 1 g to about 30 g per day. For example, the administered dose ranges of acetyl-leucine are from about 1 g to about 15 g per day, from about 1 g to about 10 g per day, or from about 1.5 g to about 7 g per day, from 15.1 g to about 30 g per day, 16 g to about 30 g per day, 17 g to about 30 g per day, 18 g to about 30 g per day, 19 g to about 30 g per day, or 20 g to about 30 g per day. It may be from about 2, 3, 4, 5, 6, 7, 8, 9, 10, 11, 12, 13, or 14 g to about 15 g per day. It may be from about 2, 3, 4, 5, 6, 7, 8 or 9 g to about 10 g per day. It may be from 15.1, 16, 17, 18, 19, 20, 21, 22, 23, 24, 25, 25, 27, 28, or 29 g to about 30 g per day. It may be more than about 1.5 g per day, but less than about 15, 14, 13, 12, 11, 10, 9, 8, 7, 6 or 5 g per day. In one embodiment, the dose ranges from about 4 g to about 6 g per day. In one embodiment, the dose ranges from about 4 g to about 5 g per day. In one embodiment, the dose is about 4.5 g per day. In one embodiment, the dose is about 5 g per day. In one embodiment, the dose is about 1 g per day, about 2 g per day, about 3 g per day, about 4 g per day, about 5 g per day, about 6 g per day, about 7 g per day, about 8 g per day, about 9 g per day, about 10 g per day, about 11 g per day, about 12 g per day, about 13 g per day, about 14 g per day, or about 15 g per day. In another embodiment, the dose is about 16 g per day, about 17 g per day, about 18 g per day, about 19 g per day, or about 20 g per day. In another embodiment, the dose is about 21 g per day, about 22 g per day, about 23 g per day, about 24 g per day, about 25 g per day, about 26 g per day, about 27 g per day, about 28 g per day, about 29 g per day, or about 30 g per day. In one embodiment, these doses are administered in a solid oral dosage form, notably tablets. In another embodiment, these doses are for acetyl-leucine when in its racemic form. Doses for acetyl-leucine when an enantiomeric excess is present may be lower, for example, around 50% lower. The above recited dose-ranges when halved are thus also explicitly encompassed by the present disclosure.

In one embodiment, miglustat is administered at a dose ranging from about 0.01 g to about 5 g per day. In another embodiment, miglustat is administered at a dose of about 0.1 g per day. In another embodiment, miglustat is administered at a dose of about 0.2 g per day. In another embodiment, miglustat is administered at a dose of about 0.3 g per day. In another embodiment, miglustat is administered at a dose of about 0.4 g per day. In another embodiment, miglustat is administered at a dose of about 0.5 g per day. In another embodiment, miglustat is administered at a dose of about 0.6 g per day. In another embodiment, miglustat is administered at a dose of about 0.7 g per day. In another embodiment, miglustat is administered at a dose of about 0.8 g per day. In another embodiment, miglustat is administered at a dose of about 0.9 g per day. In another embodiment, miglustat is administered at a dose of about 1 g per day.

In one embodiment, the total daily dose of acetyl-leucine may be spread across multiple administrations, i.e., administration may occur two or more times a day to achieve the total daily dose. As an example, the required number of tablets to provide the total daily dose of a acetyl-leucine may be split across two administrations (for example, in the morning and evening) or three administrations (for example, in the morning, noon and evening). Each dose may be suitably administered with or without food. For example, N-acetyl-L-leucine or N-acetyl-DL-leucine may be dosed by about 1 or about 2 hours before meals, such as at least about 20 minutes, at least about 30 minutes, at least about 40 minutes, or at least about 1 hour before meals, or may be dosed by about 1, about 2, or about 3 hours after meals, such as waiting at least about 20 minutes, at least about 30 minutes, at least about 1 hour, at least about 1.5 hours, at least about 2 hours, or at least about 2.5 hours after meals. For example, a total daily dose of 4.5 g acetyl-DL-leucine may be administered as three Tanganil® (or equivalent) tablets before, with, or after breakfast, three further tablets before, with, or after lunch and three further tablets before, with, or after dinner.

The treatment duration for the combination of acetyl-leucine and miglustat may be about seven days or more. For example, the treatment duration may be about two weeks or more, about three weeks or more, about one month or more, about six weeks or more, about seven weeks or more, or about two months or more. In one embodiment, the treatment duration is about three months or more, e.g., about four months or more, about five months or more or about six months or more. The treatment duration may also be about 1 year or more, about 2 years or more, about 4 years or more, about 5 years or more, or about 10 years or more. The treatment duration may also be the life-time of the subject.

Any and all combinations of dosage form, dose amount, dosing schedule, and treatment duration for the combination of acetyl-leucine and miglustat are envisaged and encompassed by the disclosure. In one embodiment, the dose of acetyl-leucine is from about 4 g to about 10 g per day, taken across one, two, or three administrations per day, for a treatment duration of about two months or more. In another embodiment, the dose of acetyl-leucine is more than 4 g but no more than 5 g per day, taken across one, two, or three administrations per day, for a treatment duration of about six months or more. The dosage form may be a solid oral dosage form, notably tablets.

In one embodiment, the combination of acetyl-leucine and miglustat is used for treating a LSD or one or more symptoms of a LSD. As used herein, "treating a LSD or one or more symptoms of a LSD" and the like refer to delaying onset of a LSD or one or more symptoms of a LSD that would otherwise be expected to manifest according to typical disease progression, reducing the severity of a LSD or reducing the severity of or eliminating one or more existing symptoms associated with a LSD, delaying progression of a LSD or one or more symptoms of a LSD over time as compared to typical disease progression, and/or reversing progression of a LSD or one or more symptoms of a LSD over time. "Treating a LSD or one or more symptoms of a LSD" may also refer to improving a biochemical marker of a LSD.

As used herein, "typical disease progression," "disease progression that would typically be expected" and the like refer to the typical or expected progression of a LSD, one or more symptoms associated with a LSD, or a biochemical marker of a LSD if the subject were untreated. Typical or expected disease progression may be based, for example, on a known scale, index, rating, or score, or other suitable test, for assessing the progression of a LSD, one or more symptoms associated with a LSD, or a biochemical marker of a LSD, such as those described herein. The scale, index, rating, score, or other suitable test may correspond to the progression of the LSD overall or to the progression of one or more symptoms associated with the LSD. For instance, typical or expected disease progression may be based on the typical or expected onset or severity of the LSD or a symptom or collection of symptoms associated with the LSD. The typical or expected disease progression may be determined on a subject-by-subject basis or may be based on what is typically observed for or experienced by a collection of subjects afflicted with the LSD, such as a population or subpopulation of subjects. Subpopulations may include, for example, subpopulations of the same gender, of the same or similar age, of the same or similar timing for the onset of one or more symptoms, etc.

In another embodiment, "treating a LSD or one or more symptoms of a LSD" refers to delaying onset of a LSD or one or more symptoms of a LSD that would otherwise be expected to manifest according to typical disease progression. As used herein, "delaying onset of a LSD or one or more symptoms of a LSD" and the like refer to increasing the time to, or preventing, onset of the LSD or one or more symptoms of the LSD. For example, onset can be said to be delayed when the time to manifestation of a LSD or one or more symptoms of a LSD takes at least 5% longer than that observed according to typical disease progression. Further for example, an increase in time of at least 10%, at least 15%, at least 20%, at least 25%, at least 30%, at least 40%, at least 50%, at least 60%, at least 70%, at least 80%, at least 90% or at least 100% is observed. In one embodiment, the subject is asymptomatic. The administration of acetyl-leucine and miglustat may be initiated at the time the subject is asymptomatic to delay onset of a LSD or one or more symptoms of a LSD that would otherwise be expected to manifest according to typical disease progression. In another embodiment, the subject is symptomatic. The administration of acetyl-leucine and miglustat may be initiated at the time the subject has some symptoms in order to delay onset of one or more additional symptoms of a LSD that would otherwise be expected to manifest according to typical disease progression. The subject in need thereof may continue to receive treatment with acetyl-leucine and miglustat in accordance with the durations described herein. In one embodiment, the treatment prevents onset of one or more symptoms of the LSD that would otherwise be expected to manifest according to typical disease progression.

In another embodiment, "treating a LSD or one or more symptoms of a LSD" refers to reducing the severity of a LSD or reducing the severity of or eliminating one or more existing symptoms associated with a LSD. The severity of a LSD or of the existing symptom(s) may be assessed using a known scale, index, rating, or score, such as those described as examples herein, or another suitable test for assessing severity. For example, the scale, index, rating, score, or other suitable test may correspond to the severity of the LSD overall or to the severity of one or more symptoms associated with the LSD. In one embodiment, the treatment improves such an assessment from a value or degree characteristic of a symptomatic patient to a value or degree characteristic of a non-symptomatic patient.

In another embodiment, "treating a LSD or one or more symptoms of a LSD" refers to delaying progression of a LSD or one or more symptoms associated with a LSD over time as compared to typical disease progression, or reversing progression of a LSD or one or more symptoms associated with a LSD over time. The time over which the treatment delays or reverses progression may coincide with the duration of treatment as described herein. The treatment may delay or reverse progression over a duration of, for example, about seven days or more, about two weeks or more, about three weeks or more, about one month or more, about six weeks or more, about seven weeks or more or about two months or more. For example, the treatment delays or reverses progression over a duration of about three months or more, about four months or more, about five months or more or about six months or more. Further for example, it delays or reverses progression over a duration of about 1 year or more, about 2 years or more, about 3 years or more, about 4 years or more, about 5 years or more, or about 10 years or more. The treatment may delay or reverse progression of the LSD or one or more symptoms associated with the LSD over the lifetime of the patient.

In another embodiment, "treating a LSD or one or more symptoms of a LSD" refers to delaying progression of a LSD or one or more symptoms of a LSD over time as compared to typical disease progression. As used herein, "delaying progression of a LSD or one or more symptoms associated with a LSD over time" and the like refer to slowing and/or stopping progression of the LSD or one or more symptoms of the LSD (e.g., slowing and/or stopping the worsening or increasing severity of the LSD or one or more symptoms of the LSD) over time. Disease progression may be determined, for example, using a known scale, index, rating, or score, such as those described as examples herein, or other suitable tests for assessing progression. For example, the scale, index, rating, score, or other suitable test may correspond to the progression of the LSD overall or to the progression of one or more symptoms associated with the LSD. In one embodiment, "delaying progression of a LSD or one or more symptoms associated with a LSD" means that a subject's disease severity value (e.g., overall severity or severity of one or more symptoms) determined by a known scale, index, rating, score, etc., or another suitable test for evaluating severity, does not meaningfully increase (e.g., at least remains substantially constant). In one embodiment, "delaying progression of a LSD or one or more symptoms of a LSD" means preventing the subject from reaching, or increasing the time taken for a subject to reach (e.g., decreasing the rate of change of increasing severity), a severity value according to a known scale, index, rating, score, etc., or other suitable test, for assessing progression compared to a value corresponding to typical disease progression. For example, progression can be said to be delayed when the time to reach a severity value takes at least 5% longer than that observed according to typical disease progression. Further for example, an increase in time of at least 10%, at least 15%, at least 20%, at least 25%, at least 30%, at least 40%, at least 50%, at least 60%, at least 70%, at least 80%, at least 90% or at least 100% is observed. The time over which the treatment delays progression of a LSD or one or more symptoms of a LSD may coincide with the duration of treatment as described herein. In one embodiment, the treatment delays progression for at least about three months, at least about four months, at least about five months, or at least about six months. In another embodiment, the treatment delays progression for at least about 1 year, at least about 2 years, at least about 3 years, at least about 4 years, at least about 5 years, or at least about 10 years. The treatment may delay progression over the lifetime of the patient.

In another embodiment, "treating a LSD or one or more symptoms of a LSD" refers to reversing progression of a LSD or one or more symptoms of a LSD over time. As used herein, "reversing progression of a LSD or one or more symptoms of a LSD over time" and the like refer to stopping progression and reducing the severity of the LSD or one or more symptoms of the LSD over time. Disease progression and severity may be determined, for example, using a known scale, index, rating, or score, such as those described as examples herein, or another suitable test for assessing progression and severity. For example, the scale, index, rating, score, or other suitable test may correspond to the progression and severity of the LSD overall or to the progression and severity of one or more symptoms associated with the LSD. In one embodiment, "reversing progression of a LSD or one or more symptoms of a LSD over time" means that a subject's disease severity value (e.g., overall severity or severity of one or more symptoms) determined by a known scale, index, rating, score, etc., or another suitable test, for evaluating severity, improves over time (i.e., shows a reduction in severity over time). The time over which the treatment reverses progression of a LSD or one or more symptoms of a LSD may coincide with the duration of treatment as described herein. In one embodiment, the treatment reverses progression for at least about three months, at least about four months, at least about five months, or at least about six months. In another embodiment, the treatment reverses progression for at least about 1 year, at least about 2 years, at least about 3 years, at least about 4 years, at least about 5 years, or at least about 10 years. The treatment may reverse progression over the lifetime of the patient.

In another embodiment, "treating a LSD or one or more symptoms of a LSD" refers to improving in the subject a biochemical marker of a LSD (e.g., increased levels of the storage metabolite(s) or secondary biochemical changes resulting from the primary storage). A biochemical marker is a signal of disease activity and may provide ongoing indications of disease severity and progression over time. In one embodiment, the biochemical marker is improved in view of a control value. In one embodiment, the biochemical marker is chosen from increased lysosomal volume and increased glycosphingolipid (GSL) levels. In one embodiment, the biochemical marker is increased lysosomal volume and the treatment reduces lysosomal volume in the subject. In one embodiment, the biochemical marker is increased glycosphingolipid (GSL) levels and the treatment reduces GSL levels in the subject. In one embodiment, the treatment improves a biochemical marker over time. For example, in one embodiment, improving a biochemical marker over time means that the treatment improves a biochemical marker over time toward a control value, prevents the progression of a biochemical marker over time, and/or delays the progression of the biochemical marker over time as compared to typical disease progression. The time over which the treatment improves a biochemical marker may coincide with the duration of treatment as described herein. In one embodiment, the treatment improves a biochemical marker for at least about three months, at least about four months, at least about five months, or at least about six months. In a further embodiment, the treatment improves a biochemical marker for at least about 1 year, at least about 2 years, at least about 3 years, at least about 4 years, at least about 5 years, or at least about 10 years. The treatment may improve the biochemical marker over the lifetime of the patient.

A "symptom" of a LSD includes any clinical or laboratory manifestation associated with a LSD and is not limited to what the subject can feel or observe. Symptoms as described herein include, but are not limited to, neurological symptoms and psychiatric symptoms. Examples of neurological symptoms include ataxia, other movement disorders such as hypokinesia, rigor, tremor or dystonia, central ocular motor disorders such as vertical and horizontal supranuclear saccade/gaze palsy and neuropsychological deficits such as dementia. Examples of psychiatric symptoms include depression, behavioural disorders or psychosis. Onset of symptoms may range from birth to adulthood.

Progression of a LSD or one or more symptoms of a LSD over time or through treatment can be monitored, for example, using one or more known tests at two or more time points and comparing the results. Disease progression and/or severity can be assessed, for example, using the Scale for the Assessment and Rating of Ataxia (SARA), Spinocerebellar Ataxia Functional Index (SCAFI), the International Cooperative Ataxia Rating Scale (ICARS), the brief ataxia rating scale (BARS), the modified Disability Rating Scale (mDRS), EuroQol 5Q-5D-5L (EQ-5D-5L), the visual analogue scale (VAS), Wechsler Adult Intelligence Scale-Revised (WAIS-R), Wechsler Intelligence Scale for Children-IV (WISC-IV), Montreal Cognitive Assessment (MoCA) or other suitable tests. For certain LSDs, such as NPC, particular scores have been developed and validated over the last decades, for instance the clinical severity score (CSS) and annual severity increment score (ASIS) (see Yanjanin et al., "Linear Clinical Progression, Independent of Age of Onset, in Niemann—Pick Disease, Type C," *Am J Med Genet Part B* 153B:132-140) and the modified 6-Domain NP-C disability Scale (mDRS score). For example, an NPC patient's severity can be quantified by assigning a CSS, which assesses various parameters of the disease (ambulation, seizures, eye movement, etc.) and gives each parameter a score out of 5. A higher score equals a greater severity. The ASIS quantifies the annual rate of change in the CSS, calculated by dividing the CSS by the patient's age. In this regard, certain scores in these tests are characteristic of symptomatic LSD patients and evidence disease progression and/or severity.

Thus, "treating a LSD or one or more symptoms of a LSD," for example, may be equated to achieving an improved assessment, such as those described herein, of a SARA, SCAFI, ICARS, BARS, mDRS, EQ-5D-5L, VAS, WAIS-R, WISC-IV, CSS and/or MoCA score, or result of another test suitable for characterising a LSD subject. For example, in one embodiment, "reducing the severity of a LSD or reducing the severity of or eliminating one or more existing symptoms of a LSD" means improving a SARA, SCAFI, ICARS, BARS, mDRS, EQ-5D-5L, VAS, WAIS-R, WISC-IV, CSS and/or MoCA score, or a result of another suitable test for evaluating severity, such as improving the score or result from a severity value characteristic of a symptomatic subject to a value characteristic of a non-symptomatic subject. In another embodiment, "delaying progression of a LSD or one or more symptoms of a LSD" means that a subject's SARA, SCAFI, ICARS, BARS, mDRS, EQ-5D-5L, VAS, WAIS-R, WISC-IV, CSS and/or MoCA score, or a result of another suitable test for evaluating progression, does not meaningfully increase (e.g., at least remains substantially constant). In a further embodiment, "delaying progression of a LSD or one or more symptoms of a LSD" means preventing a subject's SARA, SCAFI, ICARS, BARS, mDRS, EQ-5D-5L, VAS, WAIS-R, WISC-IV, CSS and/or MoCA score, or a result of another suitable test for evaluating progression, from reaching, or increasing the time taken to reach, a value compared to that of typical disease progression. In another embodiment, "reversing progression of a LSD or one or more symptoms of a LSD over time" means that a subject's SARA, SCAFI, ICARS, BARS, mDRS, EQ-5D-5L, VAS, WAIS-R, WISC-IV, CSS and/or MoCA score, or result of another suitable test for evaluating progression, improves over time (i.e., shows a reduction in severity over time).

For example, to evaluate overall neurological status, mDRS, a four-domain scale (ambulation, manipulation, language and swallowing), may be applied. Cerebellar function may be evaluated using SARA, an eight-item clinical rating scale (gait, stance, sitting, speech, fine motor function and taxis; range 0-40, where 0 is the best neurological status and 40 the worst), and SCAFI, comprising the 8-m-Walking-Time (BMW; performed by having patients walking twice as quickly as possible from one line to another excluding turning), 9-Hole-Peg-Test (SHPT) and the number of "PATA" repetitions over 10 s. Subjective impairment and quality of life may be evaluated using the EQ-5D-5L questionnaire and VAS. To assess ocular motor function, 3-dimensional videooculography (EyeSeeCam) may be used to measure the peak velocity of saccades, gain of smooth pursuit, peak slow phase velocity of gaze-evoked nystagmus (gaze-holding function), peak slow phase velocity of optokinetic nystagmus, and gain of horizontal vestibulo-ocular reflex. To evaluate the cognitive state, WAIS-R or WISC-IV, and MoCA, assessing different cognitive domains, including attention and concentration, executive functions, memory, language, visuoconstructional skills, conceptual thinking, calculations, and orientation with a maximum of 30 points and a cut-off score of 26, may be used. The skilled person will know how to perform these and other such tests.

EXAMPLES

General Methods

Animals and Treatments

BALBc/NPC $^h$ and Sandhoff mice were bred as heterozygotes to generate affected mice (Npc1$^{-/-}$, Hexb$^{-/-}$) and controls (Npc$^{+/+}$, Hexb$^{+/+}$). The mice were housed under non-sterile conditions, with food and water available ad libitum. All experiments were conducted using protocols approved by the UK Home Office Animal Scientific Procedures Act, 1986.

Cells

Wild type and NPC1 null Chinese Hamster Ovary (CHO) cells were kindly provided by Chris Wassif (NIH).

Antibodies

The antibodies used in this study are summarised in Table 2.

TABLE 2

| Abv/acronym | Antibody type | Host | Source | Catalogue code | Dilution |
| --- | --- | --- | --- | --- | --- |
| Calbindin-D28K | Mab | Rabbit | Swant | CB38a | 1:2000 |
| CD68 | Mab | Rat | Bio-Rad | MCA1957 | 1:500 |
| Alexa Fluor 594 anti rabbit | Secondary Ab | Goat | abcam | ab150080 | 1:1000 |
| Alexa Fluor 488 anti rat | Secondary Ab | Goat | abcam | ab150157 | 1:2000 |
| LC3B | Polyclonal | Rabit | abcam | ab51520 | 1:2000 |
| P62 | Mab | Mouse | abcam | ab56416 | 1:2000 |
| GDH | Mab | Rabit | CellSignalling | D9F7P | 1:1000 |
| pMTOR (ser 2448) | Polyclonal | Rabit | CellSignalling | 2971 | 1:500 |
| mTOR | Polyclonal | Rabit | CellSignalling | 2972 | 1:500 |

TABLE 2-continued

| Abv/acronym | Antibody type | Host | Source | Catalogue code | Dilution |
|---|---|---|---|---|---|
| PDH Complex | Polyclonal | Mouse | abcam | ab110416 | 1:1000 |
| pPDH (s293) | Polyclonal | Rabit | abcam | ab92696 | 1:500 |
| SOD1 | Polyclonal | Rabit | abcam | ab13498 | 1:1500 |
| SOD2 | Polyclonal | Rabit | abcam | ab56416 | 1:1500 |
| PDP1 | Polyclonal | Rabit | abcam | ab228578 | 1:1000 |
| PDK1 | Mab | Mouse | abcam | ab110025 | 1:1000 |
| PDK2 | Mab | Rabit | abcam | ab68164 | 1:1000 |
| PDK4 | Mab | Rabbit | abcam | ab214938 | 1:1000 |
| BCKADH-A | Polyclonal | Rabbit | abcam | ab90691 | 1:1000 |
| pBCKADH-A | Polyclonal | Rabbit | abcam | ab200577 | 1:1000 |
| LDHB | Mab | Mouse | abcam | ab85319 | 1:1500 |
| PGC-1 alpha | Mab | Mouse | Merck Millipore | ST1202 | 1:1500 |
| Anti-Mouse 800CW IgG (H + L) | Secondary Ab | Goat | Licor-IRDye | 925-32210 | 1:10,000 |
| Anti-Rabbit 680RD IgG (H + L) | Secondary Ab | Goat | Licor-IRDye | 925-68071 | 1:10,000 |
| HRP conjugated beta actin | Mab | Mouse | Invitrogen | MA5-15739-HRP | 1:15,000 |
| Pierce ECL Substrate Kit | — | — | Thermo Fisher | 32106 | — |

Acetyl-Leucine

ADLL and enantiomers (ADLL: Molekula #73891210, ALL: Sigma Aldrich #441511, ADL: Sigma #A0876) were administered as dry admix in powdered mouse diet (PicoLab Rodent Diet 20/5053, LabDiet) at a dose of 0.1 g/kg/day for in vivo studies. Treatment groups for in vivo study consisted of at least 5 mice per group. In vitro studies were conducted with each compound dissolved in PBS to generate a 50 mM stock solution and diluted to a 1 mM working concentration in media (DMEM High Glucose-Gibco #10566016).

Miglustat

Miglustat (Monsanto/Oxford GlycoSciences) was administered as a dry solid mixed with powdered chow (600 mg/kg/day) (see above) alone or in combination with ADLL.

Mouse Behavioural Analysis

The weight and activity of each mouse was recorded weekly until reaching the humane endpoint (defined as a loss of 1 g body weight within 24 h). Gait analysis was performed using CatWalk 10.5 system (Noldus) according to the manufacturer's instructions and five runs were recorded per animal at each time point. The camera was set to 40 cm below the walkway, the walkway was approximately 4 cm wide, and detection settings set to camera gain 14.05 and green intensity 0.12. Motor function was measured using an accelerating NG Rota Rod for mice (Ugo Basile) starting from 1 rpm to 10 rpm, accelerating every 30 seconds by one rpm. Bar crossing experiments on Sandhoff animals were conducted to measure motor strength and coordination. The apparatus used was modified from published studies. Briefly, a metal bar (1.2 mm width and 26 cm in length) was suspended horizontally between two wooden supports 30 cm high over a cushioned surface and animals were allowed to grasp the center of the bar with forepaws only, the tail was released, and the clock was started. Latency to cross or fall from the bar was scored, with 120 sec, maximum, to termination of each trial. A score was given to each animal between +120 and −120. If crossing time was greater than 0, then score=120−CT; if falling time was greater than 0, the score=FT−120.e

Sample Preparation

Biochemical and immunohistochemical analyses. Mice were saline perfused under terminal anaesthesia. Tissues for biochemical analysis were snap-frozen on ice-cold isopentane. For immunofluorescent staining, tissues were perfused with 4% PFA followed by PBS and kept in 4% PFA for 24h and stored in PBS containing 20% sucrose longer term. Brains were cut parasagitally (20 micron sections) and stored in 30% ethylene glycol, 30% glycerol 0.1 M sodium phosphate buffer (pH 7.4) at −20° C. Biochemical analysis was performed on water-homogenised tissues (50 mg/ml) and protein content was determined using a BCA protein assay (Thermo Fisher #23227) according to the manufacturer's instructions.

Western blot analyses. Western blot analysis was carried out by homogenising half cerebellums (ranging from 15 to 30 mg wet weight) in RIPA buffer (Pierce RIPA Buffer, Thermo Fischer Scientific-89900) with protease/phosphatase inhibitor cocktail (Halt™ Protease and Phosphatase Inhibitor Cocktail-100×, Cat No: 78440) to achieve 50 mg/ml w/v. Samples then incubated for 30 minutes on ice. They were centrifuged at 13,000 g at 4° C. and supernatants were retained for BCA protein assay and western blotting.

ADP and ATP extraction. ADP and ATP were extracted with Phenol-TE from tissues according to published methods. Briefly, freshly prepared tissues were homogenized with 3.0 mL of ice-cold phenol—TE (Sigma-77607) and processed with three cycles of 30-s homogenization and 30-s cooling. One mL of homogenate was transferred into tubes containing 200 uL of chloroform and 150 uL of de-ionized water. The homogenate was thoroughly shaken for 20s and centrifuged at 10,000×g for 5 min at 4° C. (standardise all temps to this format). The supernatant was diluted 1000-fold with deionized water, the diluted extract was used for ADP/ATP analyses.

NAD and NADH extraction. NAD and NADH extractions were performed with 20 mg fresh tissue that was PBS washed on wet ice. Tissues were homogenised with a Dounce homogeniser with 400 uL of NADH/NAD extraction buffer (Abcam NAD/NADH Assay kit-ab65348), followed by centrifugation for 5 min at 4° C. at 13.000 g.

Supernatants were collected into a new tube and filtered through 10 kD Spin column (Abcam, #ab93349) at 10,000 g at 4° C. until the majority of the liquid had passed through (approximately 20 min).

Sample Analysis

Sphingoid Base Measurements: Sphingoid bases (sphingosine and sphinganine) were extracted from 100 uL tissue homogenates in 500 uL of chloroform:methanol (1:2v/v) followed by sonication for 10 minutes at room temperature. Subsequently, 1 M 500-uL sodium chloride, 500 uL chloroform, and 3 M 100 uL sodium hydroxide were added to the samples, and vortexed every five minutes for 15 minutes at room temperature. Homogenates were centrifuged (13,000 g for 10 minutes) and the lower organic phase retained. Sphingoid bases were purified from the samples by pre-equilibrating SPA-NH2 columns with 2×1 mL chloroform followed by sample elution with 3×300 ul acetone. The samples were dried under nitrogen. Lipids were resuspended in 50 uL pre-warmed ethanol (37° C.) and 50 uL OPA labelling solution (1 mg OPA/20 uL Ethanol/1 uL 2-mercaptoethanol; dilution 1:2000 in 3% boric acid pH 10.5) was added. Samples were kept at room temperature in the dark for 20 minutes and vortexed every 10 minutes. Samples were buffered with 100 uL methanol: 5 mM Tris pH 7 (9:1) and centrifuged at 5,000 g for 2 minutes. Supernatants (150 uL) were loaded onto a reverse phase HPLC. Chromatography was carried out using a mobile phase of 85% acetonitrile/15% $H_2O$ at a flow rate of 1.0 ml/min. The orthophthaldehyde-labelled derivatives were monitored at an excitation wavelength of 340 nm and an emission wavelength of 450 nm. Quantification of trace peak area was carried out using EZChrom Elite software v3.2.1.

Glycosphingolipid measurements: Glycosphingolipids were extracted and measured by NP-HPLC according to published methods. Tissue homogenates in chloroform/methanol (C:M) (1:2 v/v) overnight at 4° C. The mixture was centrifuged (3000 rpm/10 min) and 1 mL chloroform and 1 mL PBS were added to the supernatant and centrifuged (3000 rpm/10 min). The lower phase was dried under $N_2$, resuspended in 50 uL C:M 1:3 v/v and combined with the upper phase. Subsequently, GSLs were recovered using C18 Isolute columns (100 mg) (Biotage) pre-equilibrated with 4×1 mL MeOH and 2×1 mL $H_2O$. Samples were washed 3×1 mL $H_2O$ and eluted with 1 mL C:M 98:2, 2×1 mL C:M 1:3, 1 mL MeOH. The column eluate was dried under $N_2$, resuspended in 100 uL C:M 2:1, dried again under N2 and resuspended in ceramide glycanase (CGase) buffer (50 mM sodium acetate pH 5.5, 1 mg/mL sodium taurodeoxycholate). 50 mU CGase was added, and samples incubated at 37° C. overnight. Released oligosaccharides were anthranilic acid (2-AA) labelled and purified by mixing with 1 mL Acetonitrile: $H_2O$ 97:3 and added to Discovery DPA-6S columns (SUPELCO, # 52625-U) pre-equilibrated with 1 mL acetonitrile, 2×1 mL $H_2O$, and 2×1 mL acetonitrile. Columns were washed with 2×1 mL Acetonitrile: $H_2O$ 95:5 v/v, and eluted in 2×0.75 mL $H_2O$. Samples were loaded 30:70 $H_2O$: MeCN (v/v) for normal phase HPLC. Solvent A was acetonitrile, solvent B was $H_2O$, and solvent C was 100 mM $NH_4OH$ (pH 3.85) in $H_2O$. Separation was carried out at 30° C. using Waters Alliance 2695 separation module, excitation 360, emission 425 using Waters 2475 Fluorescence detector.

Cholesterol measurements: Cholesterol was measured with the Amplex Red kit (Molecular Probes) according to the manufacturer's instructions. Briefly, cell and tissue homogenates in 100 uL mQ water were Folch extracted and dried down under nitrogen. The pellets containing cholesterol were resuspended in 1×Reaction Buffer, and 50 uL was loaded for each sample in a flat bottom 96-well plate. The reaction was initiated by adding Working Solution per sample (25% Amplex® Red, 2U/mL HRP stock solution, 2 U/mL cholesterol oxidase stock solution, 0.2 U/mL cholesterol esterase stock solution in 1×Reaction Buffer). Samples were incubated at 37° C. for 30 minutes and the fluorescence was measured in a microplate reader (Optima, BMG Labtech) using excitation in the range of 530-560 nm and emission detection at ~590 nm.

Lysotracker Green and Propidium Iodide Staining of CHO cells: In vitro FACS experiments were performed in order to measure relative acidic compartment volume staining live cells with LysoTracker™ Green DND-26 (Thermo Fisher-L7526) at 250 nM for 10 minutes in PBS at RT, centrifuged at 1200 rpm for 10 min and cells resuspended in FACS buffer (PBS, 1% BSA, 0.1% NaN3 sodium azide). Cells were stained with propidium iodide (20 nM) (Invitrogen-P3566) immediately prior to analysis on the FACS for dead cell discrimination. FACS analysis was performed on 10,000 recorded cells using FACS Canto (Becton Dickinson, (BD)) with BD software.

Filipin Staining: Free cellular cholesterol in CHO cells was visualized with Filipin (from Streptomyces fihpinensis (Sigma)). Cells were fixed with 4% paraformaldehyde, washed 3×PBS and incubated with 1.5 mg/mL glycine for 10 min to quench auto-fluorescence. Cells were incubated with filipin (0.05 mg/mL in PBS/10% FBS/0.2% Triton×100) for 2 hours, washed 3×PBS and visualized by Leica-SP8 confocal microscope.

Immunohistochemistry: Free-floating brain sections in glycerol/ethylene were rinsed 3 times with PBS and blocked with 2% goat serum in 0.3% PBS Triton at room temperature. Sections were stained with primary antibodies; rabbit Calbindin (1:2000) and rat CD68 (1:500) in 2% goat serum in 0.3% PBS for 16 hours at 4° C., followed by washing with 0.3% PBS Triton, then 3 times with PBS. Secondary antibody staining (Alexa Fluor 597 Goat anti rabbit Far Red, Alexa Fluor 488 Goat anti rat) was conducted at room temperature for 2 hours. The antibodies used are summarised in Table 2. Samples were washed once with 0.3% PBS Triton, 3 times with PBS and manually mounted on slides. Slides left on the bench overnight to dry the sections followed by application of ProLong Gold (Invitrogen, #P36930).

Western Blotting: Homogenates of cerebellum (50 mg/ml) were stored with 1% Igepal CA, 0.5% sodium deoxycholate, 0.1% SDS, and 1% protease-phosphatase inhibitor cocktail. Samples were resolved using 4-12% SDS Tris-Glycine (Biorad) gel electrophoresis and transferred to low fluorescent PVDF membrane (Biorad Immunblot Low Fluorescence PVDF paper-#1620262) using a semidry transfer apparatus (Trans-Blot Turbo Transfer System (Biorad #1704150)). The antibodies used are summarised in Table 2.

Image Acquisition and Quantification: Brain sections and CHO cells imaging was performed with a Leica-SP8 confocal microscope in tile imaging mode. Western blot data acquisition was conducted with LiCOR Odyssey Infrared Imaging system model no 9120. Mean fluorescence values, cerebellum diameters and areas, cell quantifications were calculated with Fuji Version 1.0 software.

ADP/ATP measurements: ADP/ATP measurements were made using a kit (Sigma Aldrich, MAK135) according to the manufacturer's instructions. The ADP/ATP ratio was calculated with the equation: (RLU-C-RLUB)/RLU-A.

NAD and NADH measurements: NAD, NADH and total NAD (NADt) (NAD+NADH=NADt) were measured with the NAD/NADH assay kit (Abcam-ab65348). Fresh samples were processed for ADP ATP extraction. Each sample was divided into 2:1) Normal samples 2) Decomposed samples. Decomposition of each sample was achieved by heating samples at 60° C. for 30 minutes on a heating block. 30 uL extracts were loaded into flat bottom clear 96 well plates, each sample comprising 3 wells: 1) Background 2) NADt 3) Decomposed samples (contains only NADH). Background reaction mix (60 uL) was loaded into "background wells", and Reaction Mix was loaded into "NADt" and "Decomposed sample" wells. The plate was incubated at room temperature for 5 minutes, and 6 uL NADH developer solution was added to the "Decomposed sample" wells. Absorbance readings were taken at 30 min intervals over 3h at 450 nm.

Demographics and statistical analysis of a clinical observational study of adult NPC patients treated with ADLL: The cohort comprised 3 females and 10 males. Consent from all participants was obtained. Twelve of the NPC patients were on miglustat therapy (minimum exposure 2.65, $1t^{st}$ quartile 3.44, median 4.92, mean 4.87, $3^{rd}$ quartile 5.80 and maximum 7.98 years). The thirteen NPC1 patients participated in an observational study treated with 5 g/day acetyl-DL-leucine (Tanganil™). Three patients had four prospective clinical severity score measurements and ten patients had five measurements taken during this observational study (NIH, CSS). Retrospective data were used to calculate rates of disease progression prior to recruitment to this study. The mean age at the start of acetyl-DL-leucine (Tanganil™) treatment was 26.59 years. The minimum age was 15.44, $1s^t$ quartile 20.97, median 26.98 and third quartile 30.79 with maximum age 37.37 years. The time in the observational treatment study was a mean of 0.53, $1^{st}$ quartile 0.81, median 1, mean 0.95, third quartile 1.13 and maximum 1.21 years.

Observational studies in GM2 gangliosidosis Patients: In a prospective observational case series in three patients with genetically proven GM2 gangliosidoses (2 patients with Tay-Sachs disease, 1 patient with Sandhoff disease) the symptomatic effects of ADLL was evaluated. Patients were treated with 0.1 g per kg body weight per day, for at least four weeks and the clinical effects determined using the Scale for the Assessment and Severity of Ataxia (SARA), the 8-meter walk test (8MWT) and the Montreal Cognitive Assessment (MoCA). Consent from all participants was obtained.

Patient 1:

A 28-yearsold male patient with a genetically confirmed diagnosis of Tay-Sachs disease presented with dysarthrophonia, tremor, ataxia of stance and gait, paraparesis, and muscular atrophy. Prior to treatment, the patient required the support of both a caregiver on one side and a wall on the other in order to walk down a corridor. The patient was receiving sodium-valproate (500 mg/d), lithium (450 mg/d), and risperidone (3 mg/d) (medications for clinically diagnosed bipolar disorder), and continued to do so during treatment with N-Acetyl-DL-Leucine. The patient was also receiving physiotherapy, ergotherapy, and logotherapy twice a week.

Patient 2:

A 32-year-old female patient with a genetically confirmed diagnosis of Tay-Sachs disease presented with ataxia of stance and gait, fine motor impairment, paraparesis of lower extremities and muscular atrophy. She was receiving physiotherapy, ergotherapy and logotherapy and continued to do so during treatment with N-Acetyl-DL-Leucine.

Patient 3:

An 8-year-old male patient suffering from Sandhoff disease, with muscle hypotrophy, epileptic cramps (tonic-clonic, about 10 seconds, self-limiting), disordered ocular movement and anarthria. His daily activities were very limited, being unable to eat, wash, or dress himself. He was receiving levetiracetam (1 g/d), lamotrigine (100 mg/d), omeprazole (20 mg/d), and miglustat (300 mg/d), in addition to physiotherapy, ergotherapy and logotherapy, and continued to do so during treatment with N-Acetyl-DL-Leucine.

Statistical Analyses: Murine Studies

Differences between groups were identified either by 1-way or 2-way analyses of variances (ANOVA); comparisons of groups were made after 2-way ANOVAs with Fisher's LSD test. Statistical tests were performed using GraphPad Prism 6 software (La Jolla, CA).

Example 1

Figure 1:
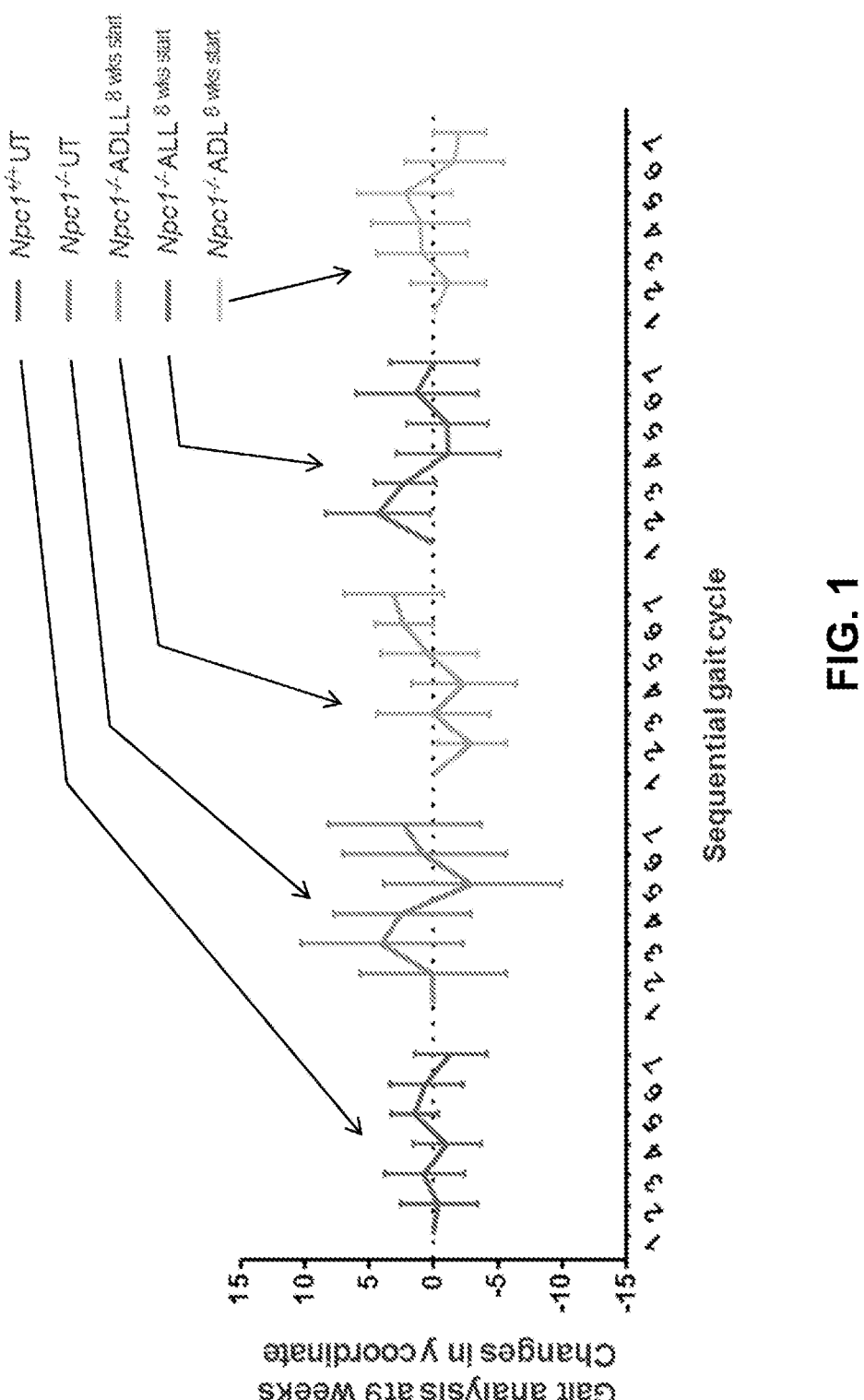
FIG. 1 is a line graph showing the late stage Y coordinate displacement of each consecutive foot from a straight-line trajectory (Mean±SD, n=6) for untreated wild type ($Npc1^{+/+}$ UT) and NPC1 ($Npc1^{-/-}$ UT) mice, and ADLL ($Npc1^{-/-}$ ADLL), ALL ($Npc1^{-/-}$ ALL), and ADL ($Npc1^{-/-}$ ADL) treated NPC1 mice (minimum 5 animals, maximum 7 animals for each group).
Figure 2:
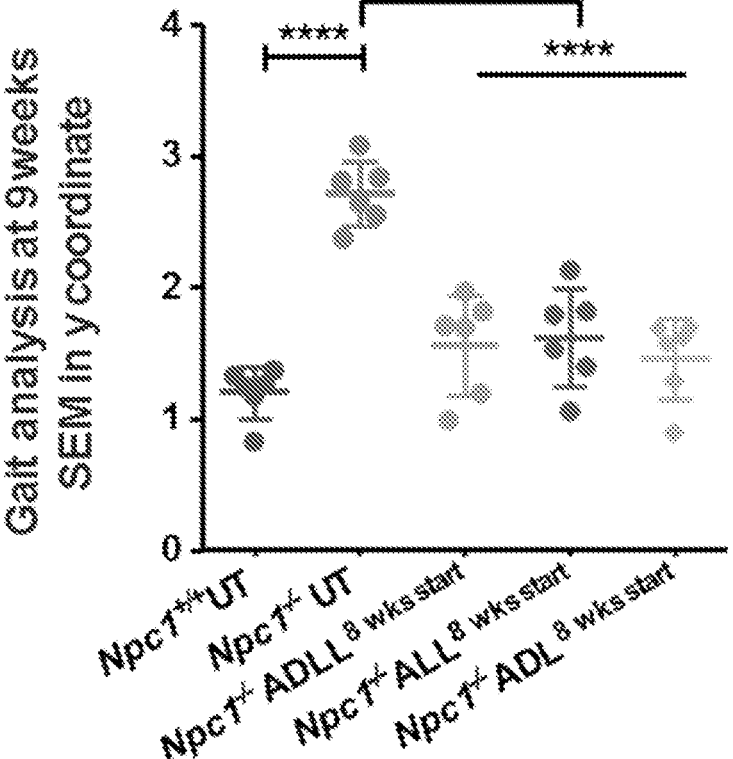
FIG. 2 is a column scatter graph showing the late stage SEMs of the Y coordinate changes (mean±SD, n=6; p<0.0001, One-way ANOVA)) for untreated wild type ($Npc1^{+/+}$ UT) and NPC1 ($Npc1^{-/-}$ UT) mice, and ADLL ($Npc1^{-/-}$ ADLL), ALL ($Npc1^{-/-}$ ALL), and ADL ($Npc1^{-/-}$ ADL) treated NPC1 mice.

ADLL, ALL and ADL Administered During the Symptomatic Phase of Disease Improves Ataxia in Npc1$^{-/-}$ Mice Npc1$^{-/-}$ mice have a 10-12-week life span, with onset of symptoms (gait abnormalities, tremor and weight loss) beginning at 6-7 weeks of age. Williams et al., *Neurobiol. Dis.* 67:9-17 (2014). ADLL, ALL, and ADL were administered to Npc1$^{-/-}$ mice in the diet (0.1 g/kg/day), a dose similar to that used in observational clinical studies. Bremova, T. et al, *Neurology* 85:1368-1375 (2015). Untreated 9-week-old Npc1$^{-/-}$ mice exhibit statistically significant (p<0.0001) ataxia that presents as a sigmoidal gait, relative to wild-type mice, whereas 9-week-old Npc1$^{-/-}$ mice treated with ADLL, ALL or ADL from 8-weeks of age (1 week of treatment) all displayed significantly reduced ataxia as determined by measuring lateral displacement from a straight trajectory in an automated gait analysis system (FIG. 1 and FIG. 2) (p<0.0001, all treatments).

Example 2

Figure 3:
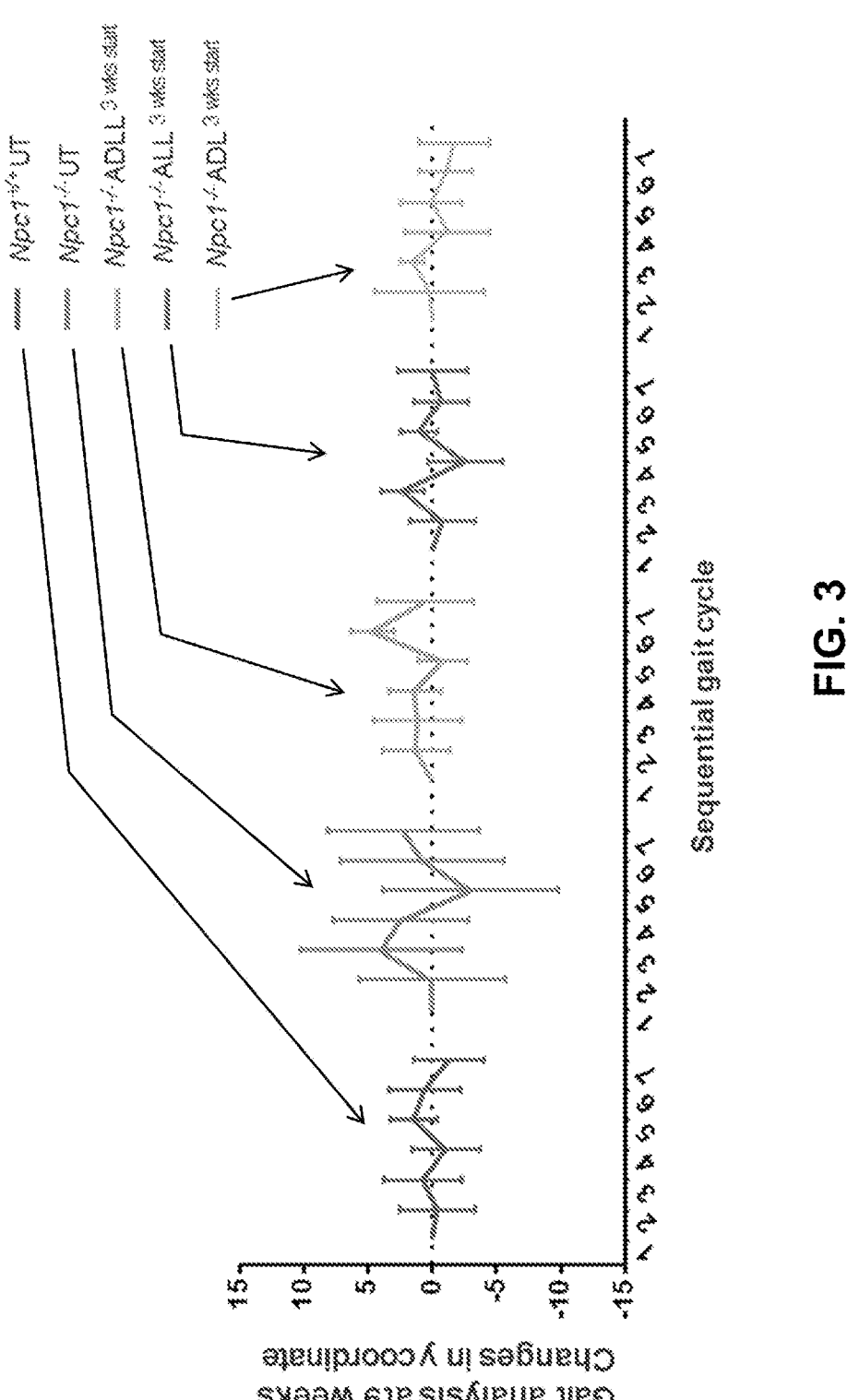
FIG. 3 is a line graph showing the early stage Y coordinate displacement of each consecutive foot from a straight-line trajectory (mean±SD, n=6)) for untreated wild type ($Npc1^{+/+}$ UT) and NPC1 ($Npc1^{-/-}$ UT) mice, and ADLL ($Npc1^{-/-}$ ADLL), ALL ($Npc1^{-/-}$ ALL), and ADL ($Npc1^{-/-}$ ADL) treated NPC1 mice.
Figure 4:
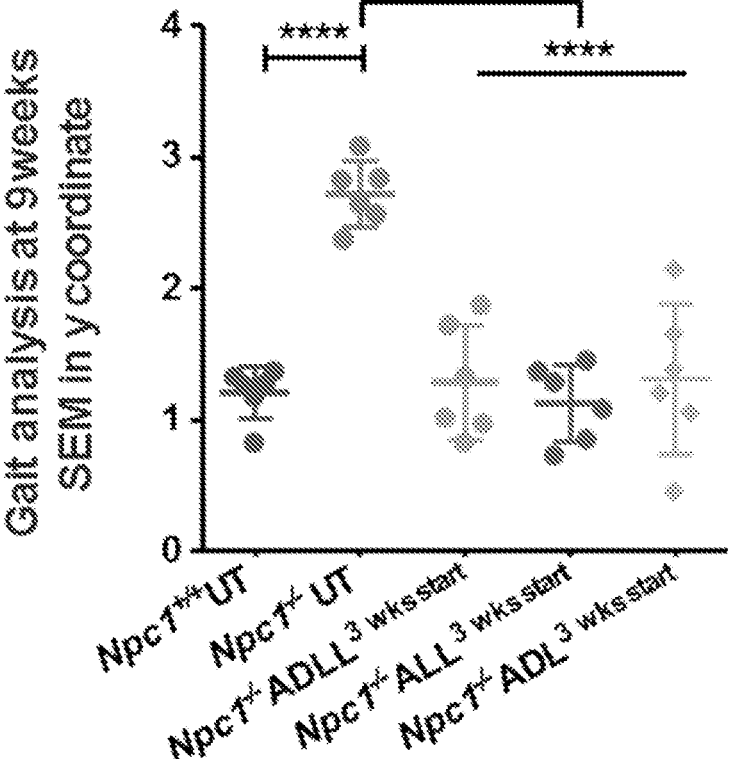
FIG. 4 is a column scatter graph showing the early stage SEMs of the Y coordinate changes (mean±SD, n=6; p<0.0001, One-way ANOVA)) for untreated wild type ($Npc1^{+/+}$ UT) and NPC1 ($Npc1^{-/-}$ UT) mice, and ADLL ($Npc1^{-/-}$ ADLL), ALL ($Npc1^{-/-}$ ALL), and ADL ($Npc1^{-/-}$ ADL) treated NPC1 mice.

Pre-Symptomatic Treatment with ADLL, ALL and ADL Improves Ataxia in Npc1$^{-/-}$ Mice Npc1$^{-/-}$ mice were treated pre-symptomatically from weaning (3 weeks of age) and assessed at 9 weeks of age (6 weeks of treatment). ADLL, ALL, and ADL significantly reduced the magnitude of ataxia (FIG. 3 and FIG. 4) with the magnitude comparable to the effects observed with one week of treatment.

Example 3

Figures 5, 6:
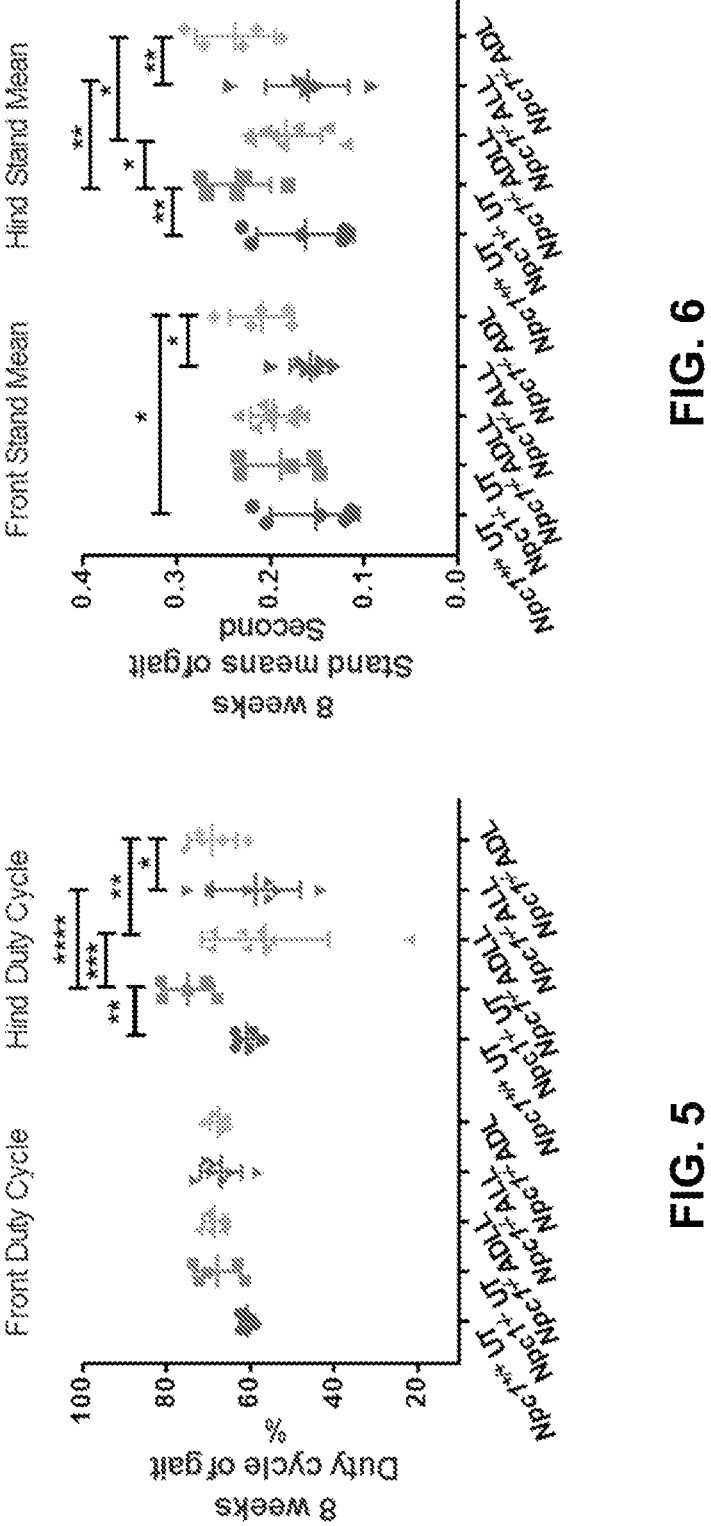
FIG. 5 is a column scatter graph showing the early stage duty cycle with front and hind duty cycle measurements (mean±SD, p<0.032, *p<0.0005, ****p<0.0001 (2-way ANOVA)) for untreated wild type ($Npc1^{+/+}$ UT) and NPC1 ($Npc1^{-/-}$ UT) mice, and ADLL ($Npc1^{-/-}$ ADLL), ALL ($Npc1^{-/-}$ ALL), and ADL ($Npc1^{-/-}$ ADL) treated NPC1 mice (minimum 5 animals, maximum 7 animals for each group).
FIG. 6 is a column scatter graph showing the early stage front and hind stand mean measurements (mean±SD, *p<0.026, **p<0.003 (2-way ANOVA)) for untreated wild type ($Npc1^{+/+}$ UT) and NPC1 ($Npc1^{-/-}$ UT) mice, and ADLL ($Npc1^{-/-}$ ADLL), ALL ($Npc1^{-/-}$ ALL), and ADL ($Npc1^{-/-}$ ADL) treated NPC1 mice (minimum 5 animals, maximum 7 animals for each group).
Figures 7, 8:
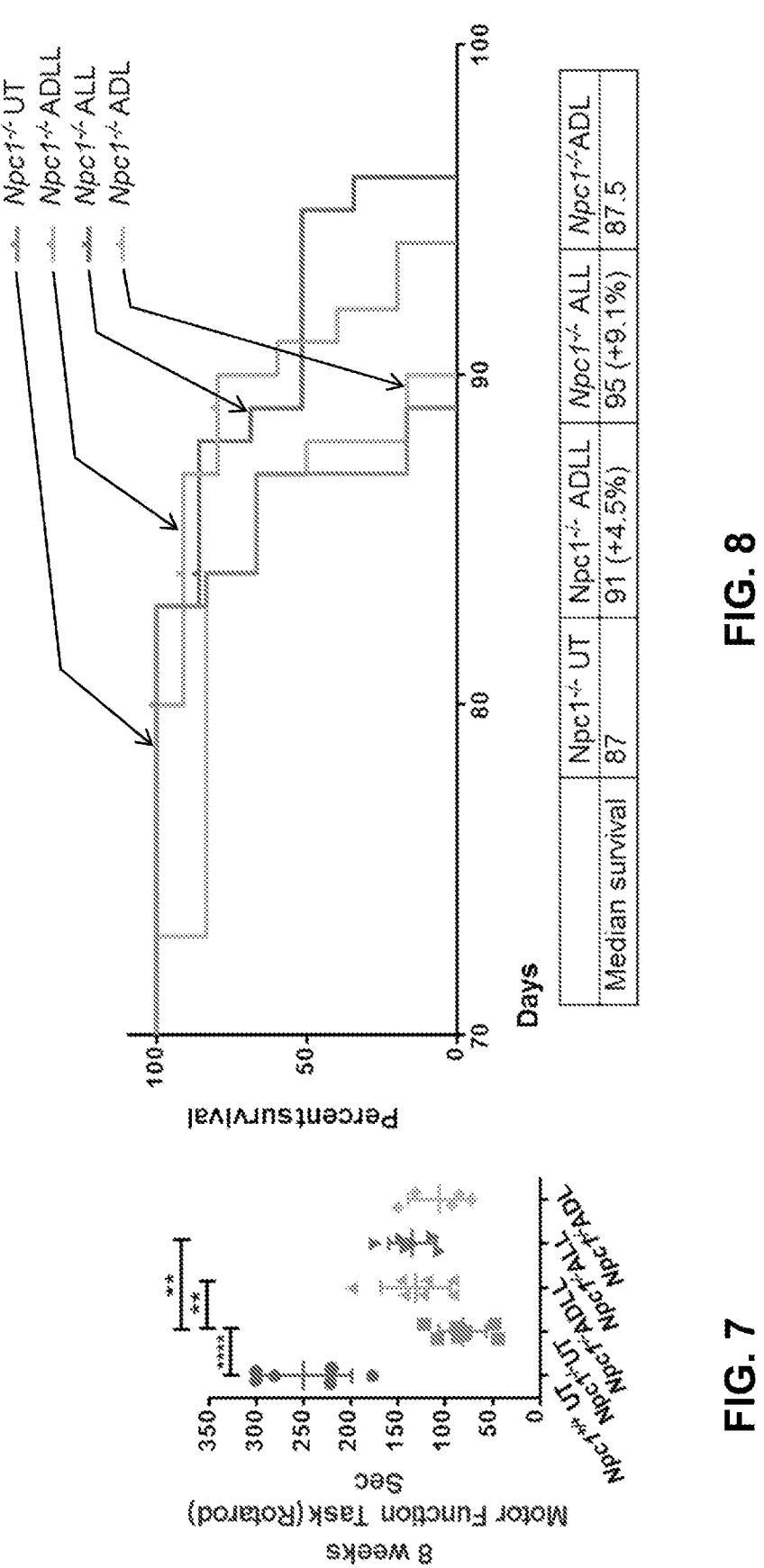
FIG. 7 is a column scatter graph showing the early stage motor performance measurements (mean±SD, p<0.009, **p<0.0001 (One-way ANOVA)) for untreated wild type ($Npc1^{+/+}$ UT) and NPC1 ($Npc1^{-/-}$ UT) mice, and ADLL ($Npc1^{-/-}$ ADLL), ALL ($Npc1^{-/-}$ ALL), and ADL ($Npc1^{-/-}$ ADL) treated NPC1 mice (minimum 5 animals, maximum 7 animals for each group).
FIG. 8 is a line graph showing the life expectancy percentages (mean±SD, *p<0.046 (Gehan-Breslow-Wilcoxon test) n=6) for untreated wild type (Npc1$^{+/+}$ UT) and NPC1 (Npc1$^{-/-}$ UT) mice, and ADLL (Npc1$^{-/-}$ ADLL), ALL (Npc1$^{-/-}$ ALL), and ADL (Npc1$^{-/-}$ ADL) treated NPC1 mice.

Pre-Symptomatic Treatment with ADLL and ALL Improves Gait Abnormalities, Motor Function, and Modestly Extends Survival in Npc1$^{-/-}$ Mice Npc1$^{-/-}$ mice develop motor dysfunction (measured by Rotarod) and paw placement abnormalities when ambulatory (measured with CatWalk). Npc1$^{-/-}$ mice were treated pre-symptomatically from weaning (3 weeks of age) and assessed the mice at 8 weeks of age. Untreated Npc1$^{-/-}$ mice had a significantly increased hind paw duty cycle (FIG. 5) (percentage of hind paws in contact with the platform relative to the elapsed time between two consecutive contacts of the same paw) and a reduced hind paw stand mean (average duration of paw in contact with the platform) relative to wild-type mice. (FIG. 6). Pre-symptomatic ADLL and ALL treatment of Npc1$^{-/-}$ mice resulted in a significantly reduced (functional improvement) duty cycle of hind paws (ADLL: p=0.0005, ALL: p <0.0001) (FIG. 5) and hind paw stand mean (indicative of functional improvement) (ADLL: p=0.0179, ALL: p=0.0014) relative to untreated Npc1$^{-/-}$ mice (FIG. 6). Rotarod performance was significantly impaired in untreated Npc1$^{-/-}$ mice relative to wild-type littermates (p<0.0001). Treatment with ADLL (p=0.0088) and ALL (p=0.0070) resulted in a significant improvement in Rotarod performance by Npc1$^{-/-}$ mice (FIG. 7). ADL treatment had no significant benefit on Npc1$^{-/-}$ mouse motor function, as assessed using Catwalk (p<0.95) or Rotarod (p=0.2218), suggesting that the D enantiomer has no benefit on these specific functional parameters. Relative to untreated Npc1$^{-/-}$ mice, the life span of animals treated from weaning was significantly increased by 8 days (9.1%) with ALL treatment (p=0.0334), 4 days with ADLL (p=0.0305) (4.5%) and was not changed with ADL (p=0.6908) (FIG. 8).

Example 4

Improved Neuropathology and Lipid Storage in Npc1$^{-/-}$ Mouse Brain in a Stereo-Selective Manner In light of the benefits of ADLL and ALL on gait, motor function and survival when treatment was initiated in the pre-symptomatic period, the impact of ALs on lipid storage in Npc1$^{-/-}$ mice was evaluated. Since NPC1 disease is characterized by the accumulation of sphingoid bases (sphingosine and sphinganine), cholesterol, sphingomyelin, free fatty acids and glycosphingolipids (GSLs), the impact of ALs administered to Npc1$^{-/-}$ mice from 3 weeks of age measuring lipid storage in brain was measured. At 59 days of age Npc1$^{-/-}$ mice exhibited increased lipid levels relative to wild-type (FIGS. 9, 10A, 10B, 11, 12A, and 12b). In order to evaluate the differential impact of the AL analogues in the CNS, the cerebellum and the forebrain (referred to as brain in the figures) were measured separately. Total GSLs in the forebrain were not significantly altered by any of the AL treatments (FIG. 27A), whilst ALL selectively reduced GM1a (20.1%; p=0.0018) and GM2 (19.6%; p=0.0222) (FIG. 9). Interestingly, although sphingosine levels were not significantly affected, ADLL and ADL reduced sphinganine levels by 13.5% (p=0.0456) and 18.2% (p=0.0111) respectively (FIGS. 10A and 10B). Analysis of the cerebellum confirmed there was no significant difference in total GSLs relative to untreated Npc1$^{-/-}$ mice with any of the AL analogues tested (FIG. 27B). However, ADLL and ALL treatment significantly lowered levels of specific GSLs including GA2 (ADLL: 21.3%, p=0.0102; ALL: 23.8%, p=0.0042), whereas a significant reduction in GA1 was only observed with ALL treatment (23.5%, p=0.0254) (FIG. 11). Comparable to the results for the forebrain, sphingosine was unchanged in the cerebellum, but sphinganine was significantly reduced following ADL treatment (42.3%, p=0.0074) (FIG. 12A and FIG. 12B).

Example 5

ADLL Ameliorates Neurodegeneration and ALL Reduces Neuroinflammation in the Cerebellum Npc1$^{-/-}$ mice exhibit progressive neurodegeneration, with cerebellar Purkinje cell loss progressing from anterior to posterior lobes, accompanied by microglial activation. ADLL treatment increased Purkinje cell survival at 59 days of age relative to untreated Npc1$^{-/-}$ littermates: 133% more Purkinje cells were present in lobules I and II (p=0.0027), and 402% more Purkinje cells in lobule III (p=0.0108) (FIG. 13). Other treatments did not significantly improve Purkinje cell survival in any cerebellar lobules (Npc1$^{-/-}$ ALL Lobule I-IIp=0.107, Lobule IIIp=0.157, Lobule IV-Vp=0.533; Npc1$^{-/-}$ ADL Lobule I-IIp=0.60, Lobule IIIp=0.11, Lobule IV-Vp=0.766, compared to Npc1$^{-/-}$ UT) (FIG. 13). In addition, only ALL treatment significantly reduced (by 20%, p=0.0177) the frequency of CD68 positive activated microglia (FIG. 14) while other treatments did not have a significant impact (p=0.1353 for Npa1$^{-/-}$ ADLL, p=0.0553 for Npc1$^{-/-}$ ADL compared to Npc1$^{-/-}$ UT). ADL did not mediate any long term, neuroprotective effects.

Example 6

AL Treatments Alleviate Lipid Storage in Non-Neuronal Tissues and Cells

Liver GSL levels in the Npc1$^{-/-}$ mice were significantly reduced in Npc1$^{-/-}$ mice treated with ADLL (26.9%, p=0.03), ADL (26.9%, p=0.0253) and 45.6% for ALL (p=0.0003) (FIG. 27C). Quantification of the major GSL species confirmed that levels of GM2Gc (the most abundant GSL in the mouse liver) was decreased significantly with all AL analogues tested (26.7% ADLL: p=0.0002, 45% ALL: p<0.0001, 29% ADL: p <0.0001), while GM3Gc levels were only reduced significantly by ALL (54.8%: p=0.0314) relative to untreated Npc1$^{-/-}$ mice (FIG. 15A). All analogues tested caused significant and comparable levels of reduction of sphingosine (the catabolic break down product of ceramide) (ADLL 29.5%, p=0.0233; ALL 33.2%, p=0.0148; ADL 33.6% p=0.0103) and its de novo precursor sphinganine (ADLL 32.5% p=0.0365; ALL 37.4% p=0.0189; ADL 38.5% p=0.0163) (FIG. 15B and FIG. 15C). Total free cholesterol in Npc1$^{-/-}$ liver was also significantly decreased after treatment with ADLL, ALL or ADL (ADLL 18.2% p=0.0346; ALL 23.4% p=0.0091; ADL 16.2% p=0.0210) (FIG. 15D). To explore whether other non-neuronal cell types were corrected by ALs the lysosomal volume as a surrogate for storage in Npc1$^{-/-}$ Chinese Hamster Ovary (CHO) cells was evaluated. Treatment with 1 mM ADLL and ALL reduced relative lysosomal volume after 24 h (ADLL 16.9%, p=0.0137; ALL 16%, p=0.0177); however, this beneficial effect was seen with all three acetyl leucine treatments after 72 h of treatment (ADLL 24% p=0.0026; ALL 22.8% p=0.0036; ADL 22.3% p=0.0042) (FIG. 16). After 72 hours AL treatment sphingosine levels were significantly reduced by 22% with ADLL (p=0.0009), 29% with ALL (p<0.0001) and 14% with ADL (p=0.0149) (FIG. 17). Total GSL levels were significantly reduced with all treatments to a comparable extent (26% with ADLL p=0.0007; 25% with ALL p=0.0010; and 22% with ADL p=0.0024) (FIG. 17). Likewise, cholesterol content was significantly reduced (18% with ADLL p=0.0043; 13% with ALL p=0.0263; and 14% with ADL p=0.0212) (FIG. 17).

Example 7

ADLL Synergises with Miglustat in Npc1$^{-/-}$ Mice

Npc1$^{-/-}$ mice were treated with ADLL in combination with the standard of care drug miglustat, resulting in a statistically significant longer life span than animals on monotherapy (Npc1$^{-/-}$ miglustat vs Npc1$^{-/-}$ miglustat & ADLLp=0.0016; Npc1$^{-/-}$ ADLL vs Npc1$^{-/-}$ miglustat &

ADLLp=0.0063; median survival; Npc1$^{-/-}$ UT: 87 days, Npc1$^{-/-}$ ADLL: 91 days; Npc1$^{-/-}$ miglustat: 117 days, Npc1$^{-/-}$ miglustat & ADLL: 138 days) (FIG. 18). Miglustat is known to cause weight loss through appetite suppression. When ADLL was used in combination with miglustat it prevented the weight loss associated with miglustat treatment (FIG. 19) but not the weight loss resulting from progression of the disease. Combination therapy significantly increased Rotarod test performance (8 weeks: p=0.0007; 10,12 weeks p<0.0001 versus untreated Npc1$^{-/-}$), with combination therapy associated with increased benefit relative to mice receiving either miglustat (10 weeks: p=0.0299; 12 weeks: p=0.0232) or ADLL monotherapy (10, 12 weeks: p<0.0001) (FIG. 20). Gait analysis at 10 weeks of age demonstrated that hind Duty Cycle percentages were significantly improved with combination therapy (p=0.0028) whereas miglustat monotherapy showed no benefit (FIG. 21). Stand mean significantly improved in mice treated either with combination therapy (p=0.0250) or miglustat monotherapy (p=0.0196) (FIG. 22).

Example 8

Neuroprotective Effects of ADLL in Observational Clinical Studies in NPC Patients Unexpected beneficial effects of ALs in Npc1$^{-/-}$ mice were discovered. Whether neuroprotective effects also occur in NPC patients treated with ADLL enrolled in an observational clinical study was investigated. Total clinical severity scores (maximum score 50, with higher values equating to increasing levels of disability) were plotted prior to initiation of treatment with Tanganil™, including available retrospective data (FIG. 23). All 13 patients had positive slopes of disease progression before ADLL treatment (1.8 severity units/year was the average slope). Following initiation of ADLL treatment the average slope was −1.78 (3 patients had no slope, 10 had negative slopes) equating to a significant reduction in disease progression and improvement in the majority of patients (One-sided sign testp=0.0002). The data were also computed as Annual Severity Increment Scores that measures the rate of disease progression and a mean of −9.1%/year (p<0.001) in ASIS scores was observed. When the treated patient data were analysed by neurological subdomain the majority of patients improved or stabilised on treatment, irrespective of the neurological subdomain measured (Table 1).

TABLE 1

| Neurological Domains | Improved | Stable | Deteriorated |
| --- | --- | --- | --- |
| Eye movement | 8 | 4 | 1 |
| Ambulation | 8 | 4 | 1 |
| Speech | 3 | 7 | 3 |
| Swallow | 10 | 2 | 1 |
| Fine motor skills | 8 | 3 | 2 |
| Cognition | 6 | 6 | 1 |
| Memory | 10 | 2 | 1 |

Example 9

ADLL Shows Benefit in Sandhoff Mice and GM2 Gangliosidosis Patients

The Sandhoff (Hexb−/−) mouse model is pre-symptomatic up to 6-8 weeks of age. Subsequently, these mice develop tremor and their motor function begins to decline. By the later stages of the disease (12-15 weeks) they are inactive and are unable to complete motor function tests such as bar crossing. Hexb$^{-/-}$ animals were treated from weaning with ADLL (0.1 mg/kg/day, the same dose used for treatment of Npc1$^{-/-}$ mice). Extended survival, with a median increase in lifespan of 8 days (p=0.0157) (FIG. 24) was observed. Bar-crossing test performance also significantly improved (12 weeks: p=0.0343; 13 weeks: p=0.0058), which is indicative of delayed deterioration in motor function (FIG. 25).

These findings in Sandhoff mice were extended to observational clinical studies in three patients with a confirmed GM2 gangliosidosis diagnosis (2 Tay-Sachs and 1 Sandhoff disease) treated with ADLL. A mean improvement of the Scale for Assessment and Rating of Ataxia (SARA) by 20.3%, the 8-M-Walking-Test (8MWT) by 17.8% and the Montreal Cognitive Assessment (MoCA) by 42% was found as shown in the FIG. 26. All patients and caregivers also reported a subjective improvement and are still on treatment at the same dosage.

REFERENCES

Neuzil, E., Ravaine, S. & Cousse, H. La N-acetyl-DL-leucine, medicament symptomatique des etats vertigineux. *Bull. Soc. Pharm. Bordeaux* 141, 15-38 (2002).

Vibert, N. & Vidal, P.-P. In vitro effects of acetyl-dl-leucine (Tanganil®) on central vestibular neurons and vestibulo-ocular networks of the guinea-pig. *Eur. J. Neurosci.* 13, 735-748 (2001).

Strupp, M. et al. Effects of acetyl-dl-leucine in patients with cerebellar ataxia: A case series. *J. Neurol.* 260, 2556-2561 (2013).

Schniepp, R. et al. Acetyl-DL-leucine improves gait variability in patients with cerebellar ataxia-a case series. *Cerebellum & ataxias* 3, 8 (2016).

Bremova, T. et al. Acetyl-DL-leucine in Niemann-Pick type C: A case series. *Neurology* 85, 1368-1375 (2015).

Platt, F. & Strupp, M. An anecdotal report by an Oxford basic neuroscientist: effects of acetyl-dl-leucine on cognitive function and mobility in the elderly. *Journal of Neurology* 263, 1239-1240 (2016).

Günther, L. et al. N-Acetyl-L-Leucine accelerates vestibular compensation after unilateral labyrinthectomy by action in the cerebellum and thalamus. *PLoS One* 10, 1-18 (2015).

Tighilet, B., Leonard, J., Bernard-Demanze, L. & Lacour, M. Comparative analysis of pharmacological treatments with N-acetyl-dl-leucine (Tanganil) and its two isomers (N-acetyl-L-leucine and N-acetyl-D-leucine) on vestibular compensation: Behavioral investigation in the cat. *Eur. J. Pharmacol.* 769, 342-349 (2015).

Platt, F. M. Emptying the stores: Lysosomal diseases and therapeutic strategies. *Nature Reviews Drug Discovery* (2018). doi:10.1038/nrd.2017.214

Cortina-Borj a, M. et al. Annual severity increment score as a tool for stratifying patients with Niemann-Pick disease type C and for recruitment to clinical trials. *Orphanet J. Rare Dis.* 13, 1-16 (2018).

Williams, I. M. et al. Neurobiology of Disease Improved neuroprotection using miglustat , curcumin and ibuprofen as a triple combination therapy in Niemann—Pick disease type C1 mice. *Neurobiol. Dis.* 67, 9-17 (2014).

Kirkegaard, T. et al. Heat shock protein-based therapy as a potential candidate for treating the sphingolipidoses. *Sci. Transl. Med.* 8, (2016).

Lloyd-Evans, E. & Platt, F. M. Lipids on trial: The search for the offending metabolite in Niemann-Pick type C disease. *Traffic* 11, 419-428 (2010).

Te Vruchte, D. et al. Relative acidic compartment volume as a lysosomal storage disorder-associated biomarker. *J. Clin. Invest.* 124, 1320-1328 (2014).

Priestman, D. A., Van Der Spoel, A. C., Butters, T. D., Dwek, R. A. & Platt, F. M. N-butyldeoxynojirimycin causes weight loss as a result of appetite suppression in lean and obese mice. *Diabetes, Obes. Metab.* (2008). doi:10.1111/j.1463-1326.2006.00701.x Kimball, S. R., Shantz, L. M., Horetsky, R. L. & Jefferson, L. S. Leucine regulates translation of specific mRNAs in L6 myoblasts through mTOR-mediated changes in availability of eIF4E and phosphorylation of ribosomal protein S6. *J. Biol. Chem.* (1999). doi:10.1074/jbc.274.17.11647

Klionsky, D. J. & Emr, S. D. Autophagy as a regulated pathway of cellular degradation. *Science* 290, 1717-1721 (2000).

Yanagisawa, H. et al. L-leucine and SPNS1 coordinately ameliorate dysfunction of autophagy in mouse and human Niemann-Pick type C disease. *Sci. Rep.* 7, 1-9 (2017).

Boland, B. et al. Macroautophagy is not directly involved in the metabolism of amyloid precursor protein. *J. Biol. Chem.* 285, 37415-37426 (2010).

Pankiv, S. et al. p62/SQSTM1 binds directly to Atg8/LC3 to facilitate degradation of ubiquitinated protein aggregates by autophagy*[S]. *J. Biol. Chem.* (2007). doi:10.1074/jbc.M702824200

Harris, R. a, Joshi, M., Jeoung, N. H. & Obayashi, M. Overview of the molecular and biochemical basis of branched-chain amino acid catabolism. *J. Nutr.* 135, 1527S-30S (2005).

Yudkoff, M. Brain metabolism of branched-chain amino acids. *Glia* 21, 92-8 (1997).

Kennedy, B. E., Hundert, A. S., Goguen, D., Weaver, I. C. G. & Karten, B. Presymptomatic Alterations in Amino Acid Metabolism and DNA Methylation in the Cerebellum of a Murine Model of Niemann-Pick Type C Disease. *Am. J. Pathol.* 1-18 (2016). doi:10.1016/j.ajpath.2016.02.012

Kato, M. et al. Structural Basis for Inactivation of the Human Pyruvate Dehydrogenase Complex by Phosphorylation: Role of Disordered Phosphorylation Loops. *Structure* 16, 1849-1859 (2008).

Huiyun, L. & Walter, W. F. PGC-1alpha: a key regulator of energy metabolism. *Adv. Physiol. Educ.* 30, 145-151 (2006).

Jha, M. K., Jeon, S. & Suk, K. Pyruvate Dehydrogenase Kinases in the Nervous System: Their Principal Functions in Neuronal-glial Metabolic Interaction and Neuro-metabolic Disorders. *Curr Neuropharmacol* 10, 393-403 (2012).

Yanj anin, N. M. et al. Linear clinical progression, independent of age of onset, in Niemann-Pick disease, type C. *Am. J. Med. Genet. Part B Neuropsychiatr. Genet.* (2010). doi:10.1002/ajmg.b.30969

Jeyakumar, M. et al. Delayed symptom onset and increased life expectancy in Sandhoff disease mice treated with N-butyldeoxynojirimycin. *Proc. Natl. Acad. Sci. U.S.A.* 96, 6388-93 (1999).

Nagamori, S. et al. Structure-activity relations of leucine derivatives reveal critical moieties for cellular uptake and activation of mTORC1-mediated signaling. *Amino Acids* 48, 1045-1058 (2016).

Harris, A., Paxton, R., Powell, S. M. & Gillim, S. E. Physiological Covalent Regulation of Rat Liver

34

Branched-Chain a-Ketoacid Dehydrogenase. *Arch. Biochem. Biophys.* 243, 542-555 (1985).

Son, S. M. et al. Leucine Signals to mTORC1 via Its Metabolite Acetyl-Coenzyme A. *Cell Metab.* 0, 1-10 (2018).

Kennedy, B. E. et al. Pre-symptomatic activation of anti-oxidant responses and alterations in glucose and pyruvate metabolism in niemann-pick type C1-deficient murine brain. *PLoS One* 8, (2013).

Ruiz-Rodado, V. et al. 1H NMR-Linked Metabolomics Analysis of Liver from a Mouse Model of NP-C1 Disease. *J. Proteome Res.* 15, 3511-3527 (2016).

Liana Roberts Stein & Imai, S. The dynamic regulation of NAD metabolism in mitochondria. *Trends Endocrinol Metab.* 23, 420-428 (2012).

Murphy, M. P. & Hartley, R. C. Mitochondria as a therapeutic target for common pathologies. *Nat. Rev. Drug Discov.* 1, (2018).

Pliss, L. et al. Cerebral Developmental Abnormalities in a Mouse with Systemic Pyruvate Dehydrogenase Deficiency. *PLoS One* 8, 1-14 (2013).

Platt, F. M., Boland, B. & van der Spoel, A. C. The cell biology of disease: lysosomal storage disorders: the cellular impact of lysosomal dysfunction. *J. Cell Biol.* 199, 723-34 (2012).

Wiederschain, G. Y. The metabolic and molecular bases of inherited disease. *Biochemistry (Moscow)* 67, 611 (2002).

Sandhoff, K. & Harzer, K. Gangliosides and Gangliosidoses: Principles of Molecular and Metabolic Pathogenesis. *J. Neurosci.* 33, 10195-10208 (2013).

Pentchev, P. G. et al. A lysosomal storage disorder in mice characterized by a dual deficiency of sphingomyelinase and glucocerebrosidase. *Biochim. Biophys. Acta—Lipids Lipid Metab.* (1980). doi:10.1016/0005-2760(80)90116-2

Sango, K. et al. Mouse models of Tay—Sachs and Sandhoff diseases differ in neurologic phenotype and ganglioside metabolism. *Nat. Genet.* (1995). doi:10.1038/ng1095-170

Barclay, L. L., Gibson, G. E. & Blass, J. P. The string test: An early behavioral change in thiamine deficiency. *Pharmacol. Biochem. Behay.* (1981). doi:10.1016/0091-3057(81)90236-7

Chida, J., Yamane, K., Takei, T. & Kido, H. An efficient extraction method for quantitation of adenosine triphosphate in mammalian tissues and cells. *Anal. Chim. Acta* 727, 8-12 (2012).

Neville, D. C. A. et al. Analysis of fluorescently labeled glycosphingolipid-derived oligosaccharides following ceramide glycanase digestion and anthranilic acid labeling. *Anal. Biochem.* (2004).doi :10.1016/j.ab.2004.03.051

All of the features described herein (including any accompanying claims, abstract and drawings), and/or all of the steps of any method so disclosed, may be combined with any of the above aspects in any combination, except combinations where at least some of such features and/or steps are mutually exclusive.

It is to be understood that the foregoing embodiments and exemplifications are not intended to be limiting in any respect to the scope of the disclosure, and that the claims presented herein are intended to encompass all embodiments and exemplifications whether or not explicitly presented herein.

All patents, patent applications, and publications cited herein are fully incorporated by reference in their entirety.

35

What is claimed is:

1. A method of reducing, or ameliorating Niemann-Pick Disease Type C, or a symptom thereof, in a subject in need thereof, the method comprising administering a combination of:
   (i) a therapeutically effective amount of acetyl-leucine; and
   (ii) a therapeutically effective amount of miglustat,
   to the subject, wherein the subject is naive to treatment with miglustat, and the combination of acetyl-leucine and miglustat reduces weight loss associated with the administration of miglustat.

2. The method of claim 1, wherein acetyl-leucine and miglustat are administered simultaneously.

3. The method of claim 2, wherein acetyl-leucine and miglustat are administered as a single pharmaceutical formulation.

4. The method of claim 2, wherein acetyl-leucine and miglustat are administered as two separate pharmaceutical formulations.

5. The method of claim 1, wherein acetyl-leucine and miglustat are administered sequentially.

6. The method of claim 5, wherein acetyl-leucine is administered before miglustat.

7. The method of claim 5, wherein acetyl-leucine is administered after miglustat.

8. The method of claim 5, wherein acetyl-leucine and miglustat are administered about 1 minute to about 6 hours apart.

9. The method of claim 8, wherein acetyl-leucine and miglustat are administered about 1 minute to 3 hours apart.

10. The method of claim 9, wherein acetyl-leucine and miglustat are administered about 1 minute to 1 hour apart.

11. The method of claim 1, wherein acetyl-leucine and miglustat are administered orally.

12. The method of claim 1, wherein acetyl-leucine is administered once, twice, or three times per day.

13. The method of claim 1, wherein miglustat is administered once, twice, or three times per day.

14. The method of claim 1, wherein about 3 g to about 15 g of acetyl-leucine is administered per day.

15. The method of claim 1, wherein about 0.05 g to about 2 g of miglustat is administered per day.

16. The method of claim 1, wherein acetyl-leucine and miglustat are administered as a first-line therapy to treat Niemann-Pick Disease Type C, or a symptom thereof.

17. The method of claim 1, wherein the acetyl-leucine is N-acetyl-DL-leucine.

18. The method of claim 1, wherein the acetyl-leucine is N-acetyl-L-leucine.

19. The method of claim 1, wherein the combination of acetyl-leucine and miglustat reduces appetite suppression associated with the administration of miglustat.

20. A kit for carrying out the method of claim 1, the kit comprising acetyl-leucine and miglustat for treating Niemann-Pick Disease Type C, or a symptom thereof, in a subject.

21. The kit of claim 20 further comprising instructions for administering the acetyl-leucine and miglustat to the subject.

* * * * *